United States Patent
Fujita et al.

(10) Patent No.: US 12,171,365 B2
(45) Date of Patent: Dec. 24, 2024

(54) COOKING ROBOT, COOKING ROBOT CONTROL DEVICE, AND CONTROL METHOD

(71) Applicant: SONY GROUP CORPORATION, Tokyo (JP)

(72) Inventors: Masahiro Fujita, Saitama (JP); Kaoru Yoshida, Kanagawa (JP); Michael Siegfried Spranger, Tokyo (JP); Tatsushi Nashida, Kanagawa (JP)

(73) Assignee: SONY GROUP CORPORATION, Tokyo (JP)

( * ) Notice: Subject to any disclaimer, the term of this patent is extended or adjusted under 35 U.S.C. 154(b) by 309 days.

(21) Appl. No.: 17/433,848

(22) PCT Filed: Feb. 14, 2020

(86) PCT No.: PCT/JP2020/005705
§ 371 (c)(1),
(2) Date: Aug. 25, 2021

(87) PCT Pub. No.: WO2020/179402
PCT Pub. Date: Sep. 10, 2020

(65) Prior Publication Data
US 2022/0142398 A1  May 12, 2022

(30) Foreign Application Priority Data
Mar. 1, 2019 (JP) .................. 2019-038072

(51) Int. Cl.
*A23L 5/10* (2016.01)
*A47J 36/32* (2006.01)
(Continued)

(52) U.S. Cl.
CPC .............. *A47J 36/32* (2013.01); *A23L 5/10* (2016.08); *A61B 5/165* (2013.01);
(Continued)

(58) Field of Classification Search
CPC ...... B25J 11/008; B25J 11/0005; B25J 13/00; B25J 9/0084; A47J 44/00; A47J 36/321; A47J 36/32
See application file for complete search history.

(56) References Cited

U.S. PATENT DOCUMENTS

| 7,174,830 B1 | 2/2007 | Dong |
| 2008/0040344 A1 | 2/2008 | Hayama |
(Continued)

FOREIGN PATENT DOCUMENTS

| CN | 1409212 A | 4/2003 |
| CN | 101013535 A | 8/2007 |
(Continued)

*Primary Examiner* — Thien S Tran
(74) *Attorney, Agent, or Firm* — Paratus Law Group, PLLC

(57) ABSTRACT

There is provided a cooking robot, a cooking robot control device, and a control method that enable a cooking robot to customize a dish prepared according to a preference of an eater. The cooking robot (1) according to one aspect of the present technology controls a cooking operation performed by a cooking arm (321), using recipe data including a data set in which cooking operation data and cook biological data are linked, the cooking operation data describing information regarding an ingredient of a dish and information regarding an operation of a cook in a cooking process using the ingredient, and the cook biological data indicating a biological reaction of the cook measured in conjunction with a progress of the cooking process. The present technology can be applied to a cooking robot that operates an arm to cook.

18 Claims, 44 Drawing Sheets

(51) Int. Cl.
  *A61B 5/024* (2006.01)
  *A61B 5/16* (2006.01)
  *A61B 5/372* (2021.01)
  *B25J 11/00* (2006.01)
(52) U.S. Cl.
  CPC ........ *B25J 11/0005* (2013.01); *B25J 11/0045* (2013.01); *A23V 2002/00* (2013.01); *A61B 5/02405* (2013.01); *A61B 5/163* (2017.08); *A61B 5/372* (2021.01); *A61B 2503/20* (2013.01)

(56) References Cited

U.S. PATENT DOCUMENTS

| | | |
|---|---|---|
| 2013/0171304 A1 | 7/2013 | Huntley |
| 2015/0064314 A1 | 3/2015 | Manuel |
| 2015/0290795 A1* | 10/2015 | Oleynik ................ A47J 36/321 700/257 |
| 2018/0242772 A1 | 8/2018 | Jenkins |

FOREIGN PATENT DOCUMENTS

| | | |
|---|---|---|
| CN | 102657482 A | 9/2012 |
| CN | 104698881 A | 6/2015 |
| CN | 107343382 A | 11/2017 |
| CN | 107705219 A | 2/2018 |
| CN | 107908670 A | 4/2018 |
| JP | 2005504259 A | 2/2005 |
| JP | 2005144093 A | 6/2005 |
| JP | 2007155825 A | 6/2007 |
| JP | 2010061381 A * | 3/2010 |
| JP | 2011-108156 A | 6/2011 |
| JP | 2016-103042 A | 6/2016 |
| JP | 2016148997 A | 8/2016 |
| JP | 2017-506169 A | 3/2017 |
| JP | 2017-536247 A | 12/2017 |
| JP | 2017220701 A | 12/2017 |
| JP | 2020131339 A | 8/2020 |
| WO | WO-2014199584 A1 | 12/2014 |

* cited by examiner

FIG. 6

FLAVOR(flavor)=TASTE( taste )+AROMA( aroma )+TEXTURE( texture )

COOKING ROBOT, COOKING ROBOT CONTROL DEVICE, AND CONTROL METHOD

CROSS REFERENCE TO PRIOR APPLICATION

This application is a National Stage Patent Application of PCT International Patent Application No. PCT/JP2020/005705 (filed on Feb. 14, 2020) under 35 U.S.C. § 371, which claims priority to Japanese Patent Application No. 2019-038072 (filed on Mar. 1, 2019), which are all hereby incorporated by reference in their entirety.

TECHNICAL FIELD

The present technology relates to a cooking robot, a cooking robot control device, and a control method, and in particular to a cooking robot, a cooking robot control device, and a control method for enabling customization of a dish made by a cooking robot according to preference of a person who eats the dish.

BACKGROUND ART

A technique for reproducing a dish made by a cook on the cooking robot side by sensing the movement of the cook during cooking and saving/transmitting data of a sensing result data is being studied. A cooking operation by the cooking robot is implemented on the basis of the sensing result of the same movement as the movement of hands of the cook, for example.

CITATION LIST

Patent Document

Patent Document 1: PCT Japanese Translation Patent Publication No. 2017-506169
Patent Document 2: PCT Japanese Translation Patent Publication No. 2017-536247

SUMMARY OF THE INVENTION

Problems to be Solved by the Invention

Cooking by a conventional cooking robot proceeds according to a recipe prepared in advance as control data. Therefore, a finished dish may not suit preference of an eater.

The present technology has been made in view of such a situation, and enables customization of a dish made by a cooking robot according to the preference of the eater.

Solutions to Problems

A cooking robot according to one aspect of the present technology includes a cooking arm configured to perform a cooking operation for making a dish, and a control unit configured to control the cooking operation performed by the cooking arm using recipe data including a data set in which cooking operation data and cook biological data are linked, the cooking operation data describing information regarding an ingredient of the dish and information regarding an operation of a cook in a cooking process using the ingredient, and the cook biological data indicating a biological reaction of the cook measured in conjunction with a progress of the cooking process.

In the one aspect of the present technology, the cooking operation performed by the cooking arm is controlled using the recipe data including a data set in which cooking operation data and cook biological data are linked, the cooking operation data describing information regarding an ingredient of a dish and information regarding an operation of a cook in a cooking process using the ingredient, and the cook biological data indicating a biological reaction of the cook measured in conjunction with a progress of the cooking process.

BRIEF DESCRIPTION OF DRAWINGS

FIG. 6 is a diagram illustrating an example of configuration elements of flavor.

MODE FOR CARRYING OUT THE INVENTION

Outline of Present Technology

Figure 1:
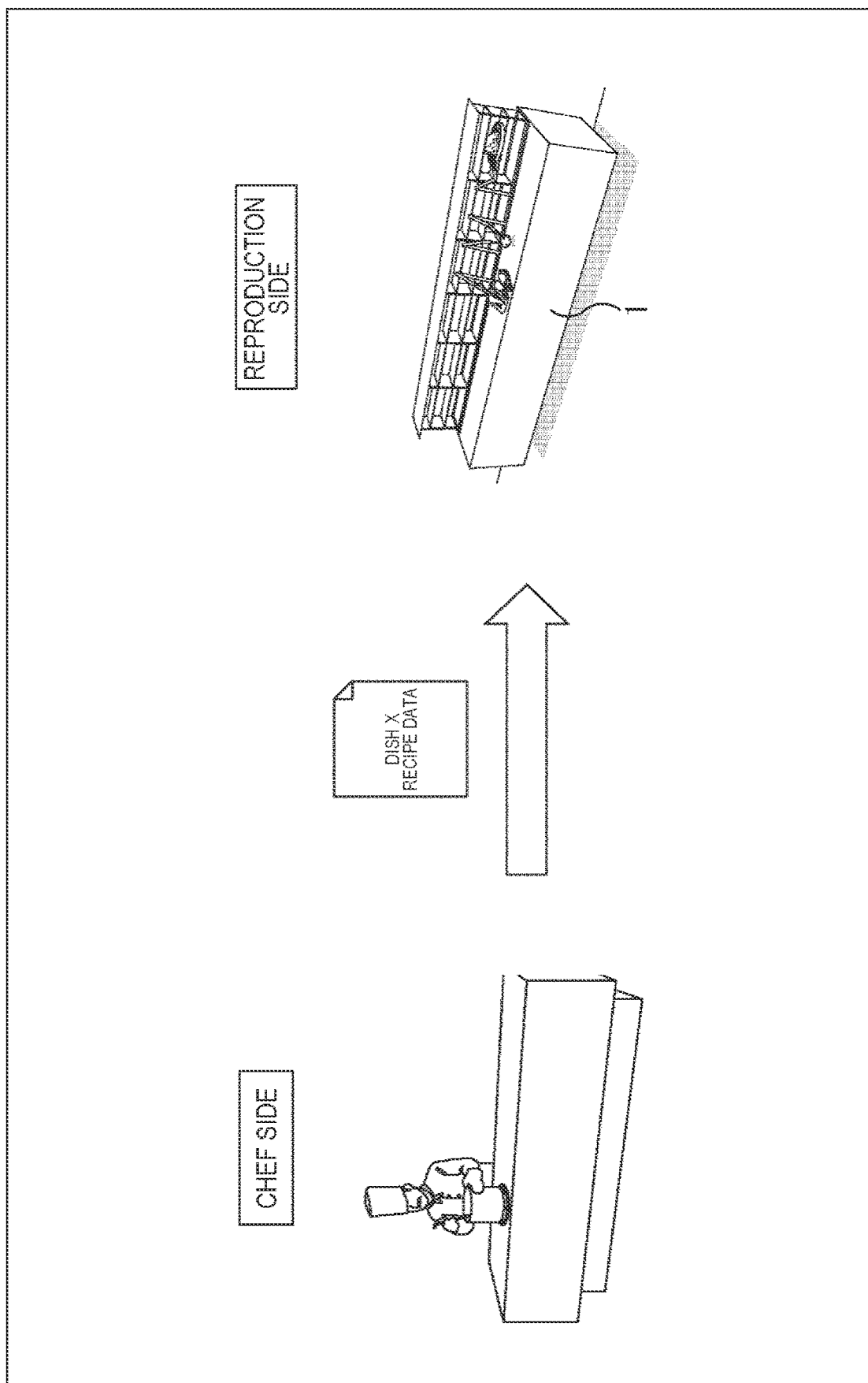
FIG. 1 is a diagram illustrating an example of overall processing in a cooking system according to an embodiment of the present technology.

The present technology senses a biological reaction of when a cook makes a dish, includes the sensed biological data in recipe data, and provides the recipe data to a cooking robot side that reproduces the dish.

Furthermore, the present technology updates a cooking process, using the biological data included in the recipe data on the cooking robot side at the time of reproducing the dish made by the cook, thereby reproducing a dish with finely adjusted flavor according to the preference of the eater.

Moreover, the present technology focuses on a difference between a sensation when a cook makes a dish and a sensation when cooking is performed on the basis of a recipe created by the cook, and links sensation data obtained by converting the sensation of the cook when making the dish into data to data describing ingredients and cooking processes to manage the linked data as recipe data.

Hereinafter, modes for carrying out the present technology will be described. Description will be given in the following order.

1. Generation of recipe data and reproduction of dish in cooking system
2. Description of recipe data
3. Generation example of recipe data
4. Example of flow of generation of recipe data and reproduction of dish
5. Modification of description of recipe data
6. Configuration example of cooking system
7. Operation of cooking system
8. Recipe data including flavor information
9. Modification <Generation of Recipe Data and Reproduction of Dish in Cooking System>

FIG. 1 is a diagram illustrating an example of overall processing in a cooking system according to an embodiment of the present technology.

As illustrated in FIG. 1, the cooking system includes a chef-side configuration for cooking and a reproduction-side configuration for reproducing a dish made by a chef.

The chef-side configuration is, for example, a configuration provided in a restaurant, and the reproduction-side configuration is, for example, a configuration provided in a general household. A cooking robot 1 is prepared as the reproduction-side configuration.

The cooking system of FIG. 1 is a system in which a dish same as the dish made by the chef is reproduced on the cooking robot 1 as the reproduction-side configuration. The cooking robot 1 is a robot including a drive system device such as cooking arms and various sensors and having a cooking function.

Recipe data indicated by the arrow is provided from the chef-side configuration to the reproduction-side configuration including the cooking robot 1. As will be described below in detail, information regarding the dish made by the chef, including the ingredients of the dish, is described in the recipe data.

In the reproduction-side configuration, the dish is reproduced by controlling cooking operations of the cooking robot 1 on the basis of the recipe data. For example, the dish is reproduced by causing the cooking robot 1 to perform the cooking operations for implementing processes same as cooking processes of the chef.

Although a chef is illustrated as a cook who performs cooking, the cooking system of FIG. 1 is applicable to a case where any person cooks as long as the person performs cooking regardless of a name such as a chef or a cook, or a role in a kitchen.

Furthermore, although one chef-side configuration is illustrated in FIG. 1, the cooking system includes a plurality of chef-side configurations respectively provided in a plurality of restaurants. The recipe data of a predetermined dish made by a predetermined chef selected by a person eats the dish reproduced by the cooking robot 1 is provided to the reproduction-side configuration, for example.

Note that the dish means a work product finished after cooking. The cooking means a process of making the dish or an act (work) of making the dish.

Figure 2:
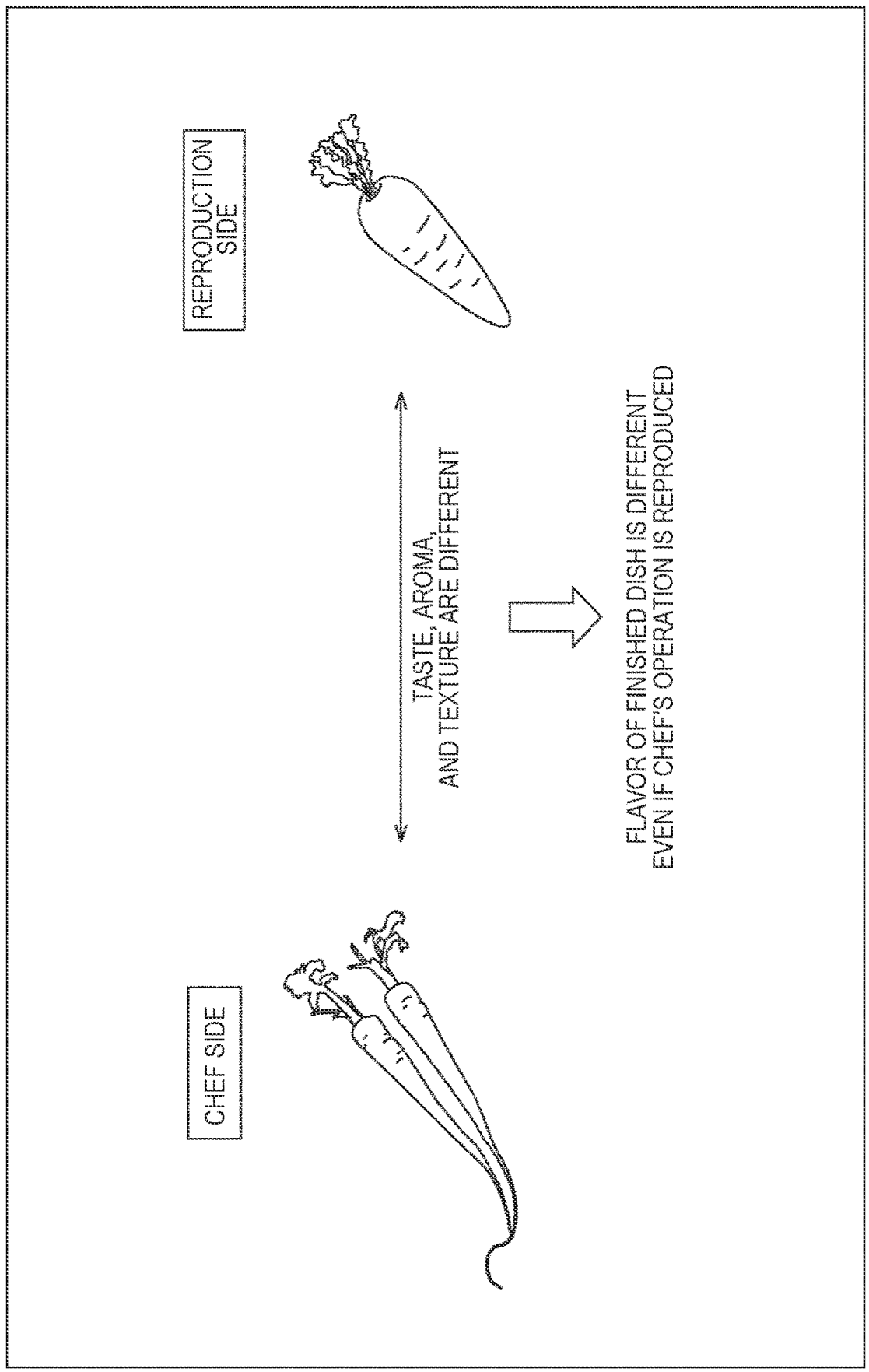
FIG. 2 is a diagram for describing a difference in ingredients used on a chef side and a reproduction side.

FIG. 2 is a diagram for describing a difference in ingredients used on the chef side and the reproduction side.

In a case where carrots are used in the chef's cooking, for example, information representing use of carrots as ingredients is described in the recipe data. Furthermore, information regarding a cooking process using carrots is described.

A cooking operation using carrots is similarly performed on the reproduction side on the basis of the recipe data.

Here, even if the ingredient is classified as the same "carrot", the carrot prepared by the chef side and the carrot prepared by the reproduction side are different in taste, aroma, and texture due to different types, production areas, harvest times, growing situations, and environments after harvesting. There are no exact same ingredients that are natural products.

Therefore, even if the cooking robot 1 performs exactly the same cooking operation as the chef's operation, the flavor of the dish prepared using carrots will be different.

A plurality of cooking processes is undergone to complete one dish, but even if looking at half-made dishes made by going through one cooking process using carrots, the flavors thereof are different between the chef side and the reproduction side.

Even if the chef feels that the dish is delicious, it may not be always the same depending on a person who eats the dish reproduced by the cooking robot 1.

Therefore, in the cooking system of FIG. 1, a biological reaction of the chef who is cooking is measured. In the recipe data provided to the reproduction side, biological information obtained by converting the biological reaction of the chef into data is described linked with information regarding ingredients and operations.

The reproduction side requires a person around the cooking robot 1 to perform tasting, such as the person who eats the dish reproduced by the cooking robot 1, by the time all the cooking processes are completed. For example, timing of tasting in which the biological reaction that the chef feels delicious is specified on the basis of the biological information included in the recipe data, and tasting is required at corresponding timing.

In addition, the biological reaction of the person who is tasting is measured, and the cooking process of the cooking robot 1 is updated as appropriate according to a measurement result.

It can be said that the biological reaction when a person puts food in its mouth expresses how the person feels the flavor. Cooking by the cooking robot 1 is controlled on the basis of the biological information representing how the chef feels the flavor, and the cooking process described in the recipe data is updated according to how the person who has performed the tasting during cooking by the cooking robot 1 feels the flavor.

Hereinafter, the biological information representing the chef's biological reaction is appropriately referred to as cook biological information.

In addition, a person who eats cooked ingredients cooked by the cooking robot 1 or a dish prepared (reproduced) using the cooked ingredients is called eater. The biological information representing the biological reaction of the eater who has tasted the dish in response to the request by the cooking robot 1 is eater biological information.

<Description of Recipe Data>

Figure 3:
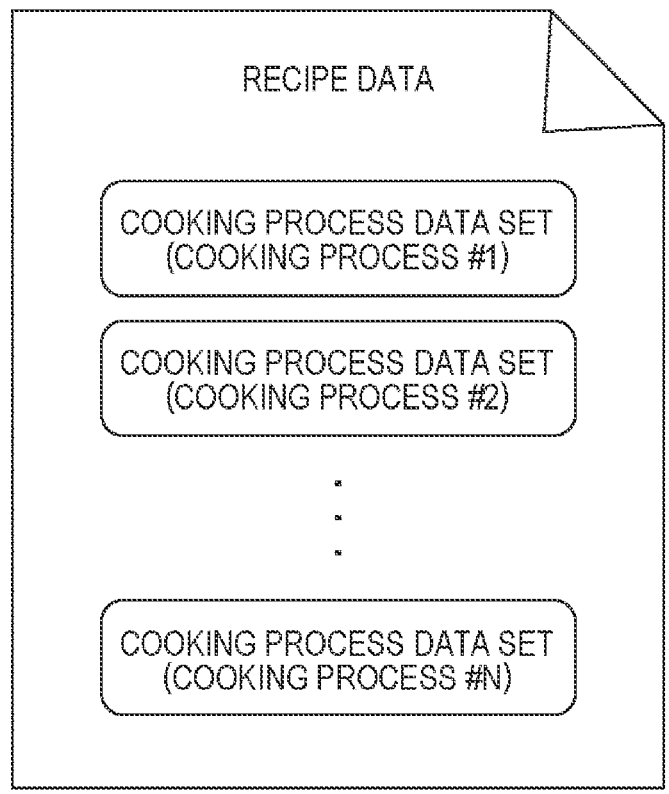
FIG. 3 is a diagram illustrating an example of description content of recipe data.

FIG. 3 is a diagram illustrating an example of description content of recipe data.

As illustrated in FIG. 3, one recipe data includes a plurality of cooking process data sets. In the example of FIG. 3, a cooking process data set related to a cooking process #1, a cooking process data set related to a cooking process #2, . . . , and a cooking process data set related to a cooking process #N are included.

Thus, in the recipe data, information regarding one cooking process is described as one cooking process data set.

Figure 4:
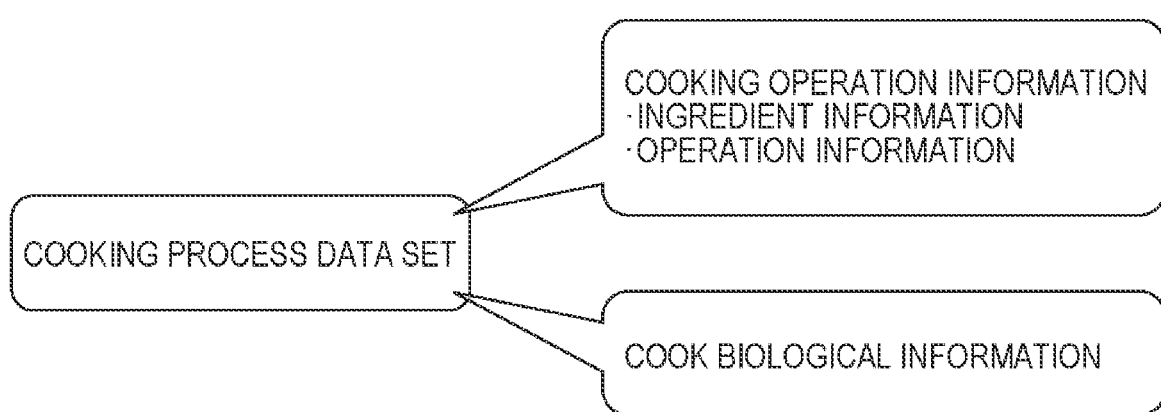
FIG. 4 is a diagram illustrating an example of information contained in a cooking process data set.

FIG. 4 is a diagram illustrating an example of the information included in the cooking process data set.

As illustrated in the balloons of FIG. 4, the cooking process data set includes cooking operation information that is information regarding cooking operations for realizing the cooking process and the cook biological information representing the biological reaction of the chef.

1. Cooking Operation Information

The cooking operation information includes ingredient information and operation information.

1-1. Ingredient Information

The ingredient information is information regarding an ingredient used by the chef in the cooking process. The information regarding an ingredient includes information representing a type, an amount, and a size of the ingredient.

For example, in a case where the chef cooks with a carrot in a certain cooking process, information representing that a carrot is used is included in the ingredient information. Information representing various foods used by the chef as ingredients for the dish, such as water and seasonings, is also included in the ingredient information. The food is a variety of stuff that a person can eat.

The ingredients include not only ingredients that have not been cooked at all but also ingredients that have been cooked (prepared) obtained by applying certain cooking. The ingredient information included in the cooking operation information of a certain cooking process includes information of cooked ingredients that have undergone a previous cooking process.

The ingredients used by the chef are recognized by, for example, analyzing an image of the chef who is cooking captured by a camera. The ingredient information is generated on the basis of a recognition result of the ingredients. The image captured by the camera may be a still image or a moving image.

The ingredient information may be registered by the chef or another person such as a staff who supports the chef at the time of generating the recipe data.

1-2. Operation Information

The operation information is information regarding a movement of the chef in the cooking process. The information regarding a movement of the chef includes information representing a movement of the chef's body at each time, including a type of a cooking tool used by the chef and a hand movement, a standing position of the chef at each time, and the like.

For example, in a case where the chef has cut a certain ingredient with a kitchen knife, the operation information includes information representing that the kitchen knife has been used as a cooking tool, information representing a cutting position, the number of cuttings, a strength of cutting, an angle, a speed, and the like.

Furthermore, in a case where the chef has stirred a pot containing a liquid as an ingredient with a ladle, the operation information includes information representing that the ladle has been used as a cooking tool, information representing a strength of a stirring method, an angle, a speed, a time, and the like.

In a case where the chef has baked a certain ingredient in an oven, the operation information includes information representing that the oven has been used as a cooking tool, heating power of the oven, a baking time, and the like.

In a case where the chef has served the ingredients on dish, the operation information includes information of tableware used for serving the ingredients, a method of arranging the ingredients, the color of the ingredients, and the like.

The movement of the chef is recognized by analyzing an image of the chef who is cooking captured by a camera, or analyzing sensor data measured by a sensor attached to the chef, for example. The operation information is generated on the basis of the recognition result of the movement of the chef.

2. Cook Biological Information

Figure 5:
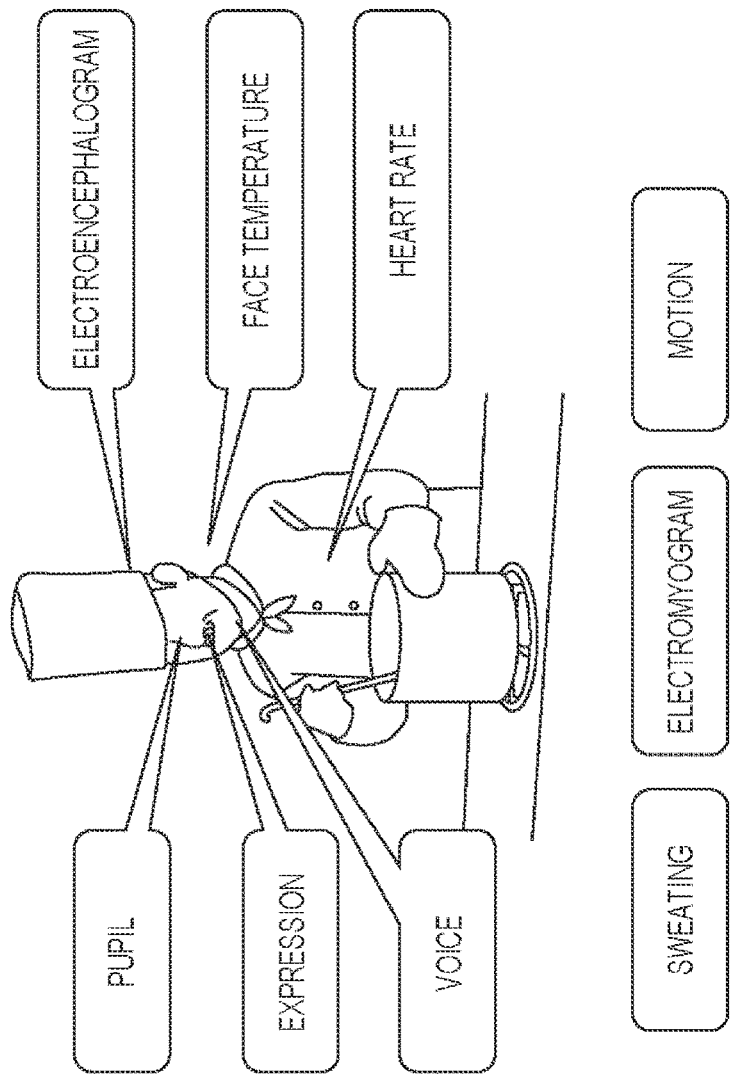
FIG. 5 is a diagram illustrating an example of a biological reaction to be measured.

FIG. 5 is a diagram illustrating an example of a biological reaction to be measured.

As illustrated in FIG. 5, for example, as the biological reaction of the chef, electroencephalogram, pupil, sweating, electromyogram of limbs, the temperature of the whole face, facial expression, motion of the whole body, heart rate, and voice are measured, for example.

(1) Electroencephalogram (EEG)

The electroencephalogram of the chef is measured using an electroencephalograph. The electroencephalogram when the chef performs tasting includes signals from gustatory receptors and olfactory receptors. By analyzing the electroencephalogram, how the chef feels the taste and aroma can be specified.

(2) Pupil

A change in a pupil of the chef is measured by analyzing an image captured by a camera. It is possible to identify emotions from the degree of opening and closing of the pupil, such as the pupil opening when a person is pleased or surprised. For example, in a case where the degree of opening and closing of the pupil of the chef who has performed tasting is higher than a threshold value, it can be presumed that the chef feels delicious.

(3) Sweating

A change in the amount of sweating of the chef is measured by analyzing the image captured by the camera or by analyzing a measurement result by a skin sensor that measures the water content in the skin. For example, eating warm or spicy foods may increase blood flow and increase sweating.

(4) Electromyogram of Limbs

A change in electromyogram of the chef is measured using an electromyograph. It is possible to identify emotions from a change in electromyogram, such as when there is a gratifying thing, the limbs are momentarily stressed and can be observed as a change in electromyogram. For example, if the electromyogram significantly changes when the chef has a taste, it can be presumed that the chef feels delicious.

(5) Temperature of the Whole Face

The temperature of the whole face of the chef is measured using an infrared sensor. For example, eating warm or spicy foods may increase blood flow and increase the temperature of the whole face.

(6) Facial Expression

A facial expression of the chef is measured by analyzing the image captured by the camera. For example, in a case of the facial expression with joy when the chef has a taste, it can be presumed that the chef feels delicious, whereas in a case of sad facial expression, it can be presumed that the chef feels not delicious.

(7) Motion of the Whole Body

A motion of the whole body is measured by analyzing the image captured by the camera and sensor data representing a measurement result of a motion sensor attached to the chef's body. Since not many people get stuck when they eat delicious food, it can be said that the motion of the whole body expresses how the people feel the flavor.

(8) Heart Rate

A heart rate of the chef is measured using a wearable activity meter. For example, in a case where the heart rate rises when the chef has a taste, it can be presumed that the chef feels delicious.

(9) Voice

A voice of the chef is measured by analyzing voice sound collected by a microphone. For example, in a case where a frequency of the chef's voice uttered during tasting is higher than a frequency of the voice uttered before tasting, it can be presumed that the chef feels delicious.

The meaning of the chef's utterance may be analyzed, and whether or not the chef feels delicious may be presumed on the basis of a result of semantic analysis. For example, in a case where utterances that affirm the flavor, such as "delicious", "good", "OK", and "yes", are made, it can be presumed that the chef feels delicious.

The cook biological information is generated on the basis of the measurement results of the biological reaction as described above, and is included in the recipe data. The cook biological information includes, as data representing how the chef feels the flavor, data representing a state of the electroencephalogram of the chef, data representing a state of the pupil, data representing a state of the sweating, data representing a state of the electromyogram of limbs, data representing a state of the temperature of the whole face, data representing a state of the facial expression, data representing a state of the motion of the whole body, data representing a state of the heart rate, and data representing a state of the voice.

Information representing at least one of the electroencephalogram, pupil, sweating, electromyogram of limbs, temperature of the whole face, facial expression, motion of the whole body, heart rate, or voice, instead of all the above biological reactions being measured, may be generated as the cook biological information.

Here, the flavor will be described.

FIG. 6 is a diagram illustrating an example of configuration elements of flavor.

As illustrated in FIG. 6, deliciousness that a person feels in a brain, that is, the "flavor", is mainly a combination of a taste obtained by a gustation of the person, an aroma obtained by an olfaction of the person, and a texture obtained by a tactile sense of the person.

The flavor also includes an apparent temperature and a color because how a person feels the deliciousness changes depending on the apparent temperature and the color of the ingredients.

Configuration elements of the flavor will be described.

(1) Taste

The taste includes five kinds of tastes (saltiness, sourness, bitterness, sweetness, and umami) that can be felt by gustatory receptor cells in a tongue and an oral cavity. The saltiness, sourness, bitterness, sweetness, and umami are called basic five flavors.

Furthermore, the taste includes pungency felt not only in the oral cavity but also in vanilloid receptors belonging to the transient receptor potential (TRP) channel family, which is a pain sensation in the whole body, in addition to the basic five tastes. Astringency is also a type of the taste although the astringency overlaps with the bitterness depending on the concentration.

Each taste will be described.

Saltiness

Substances that give the saltiness include minerals (Na, K, Fe, Mg, Ca, Cu, Mn, Al, Zn, and the like) that form salts by ionization bonds.

Sourness

Substances that give the sourness include acids such as a citric acid and an acetic acid. Generally, the sourness is felt depending on a decrease in pH (for example, about pH3).

Sweetness

Substances that give the sweetness include sugars such as sucrose and glucose, lipids, amino acids such as glycine, and artificial sweeteners.

Umami

Substances that give the umami include amino acids such as a glutamic acid and an aspartic acid, nucleic acid derivatives such as an inosinic acid, a guanylic acid, and a xanthylic acid, organic acids such as a succinic acid, and salts.

Bitterness

Substances that give the bitterness include alkaloids such as caffeine, humulones such as theobromine, nicotine, catechin, and terpenoids, limonine, cucurbitacin, flavanone glycoside naringin, bitter amino acids, bitter peptides, bile acids, and inorganic salts such as calcium salt and magnesium salt.

Astringency

Substances that give astringency include polyphenols, tannins, catechins, polyvalent ions (Al, Zn, and Cr), ethanol, and acetone. The astringency is recognized or measured as part of the bitterness.

Pungency

A substance that gives the pungency includes capsaicinoid. As biological functions, capsaicin, which is a component of hot peppers and various spices that a person feels hot, and menthol, which is a component of peppermint that a person feels cold, are recognized by warmth receptors of the TRP channel family as pain sensations rather than taste sensations.

(2) Aroma

The aroma is perceived by volatile low molecular weight organic compounds with a molecular weight of 300 or less that are recognized (bound) by olfactory receptors expressed in a nasal cavity and nasopharynx.

(3) Texture

The texture is an index called food texture, and is represented by hardness, stickiness, viscosity, cohesiveness, polymer content, water content (moisture), oil content (greasiness), and the like.

(4) Apparent Temperature

The apparent temperature is a temperature felt by human skin. The apparent temperature is not only the temperature of the food itself but also temperature sensations that a surface layer of the skin feels in response to food components, such as refreshing feeling of foods containing volatile substances such as mint, and the warmth feeling of foods containing pungent ingredients such as chili peppers.

(5) Color

The color of food reflects pigments contained in the food and the components of bitterness and astringency. For example, a plant-derived food includes pigments produced by photosynthesis and components related to the bitterness and astringency of polyphenols. The components included in the food can be estimated from the color of the food by an optical measurement method.

<Generation Example of Recipe Data>

Figure 7:
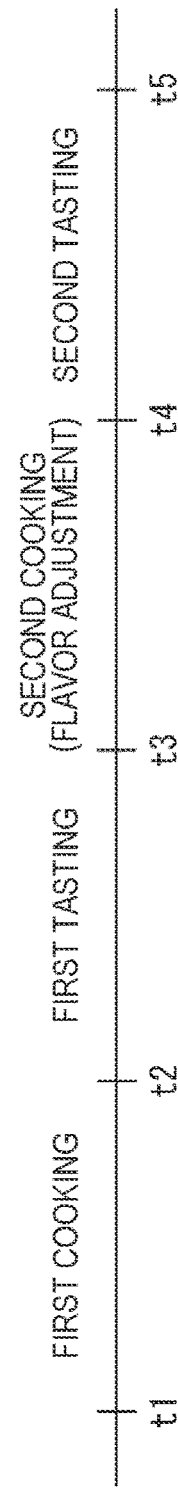
FIG. 7 is a diagram illustrating an example of a cooking process.

FIG. 7 is a diagram illustrating an example of a cooking process.

Cooking by the chef is usually carried out by repeating cooking using ingredients, tasting the cooked ingredients, and adjusting the flavor, for each cooking process.

The flavor is adjusted by adding a process of, for example, adding salt when the saltiness is insufficient, or squeezing lemon juice when the sourness is insufficient. The aroma is adjusted by adding a process of, for example, chopping and adding herbs, or heating the ingredients. The texture is adjusted by adding a process of, for example, beating the ingredients to become tender when the ingredients are hard, or increasing the time for simmering the ingredients.

In a cooking process #1 of FIG. 7, cooking using ingredients is performed as the first cooking between time t1 and time t2, and tasting of the cooked ingredients is performed as the first tasting between time t2 and time t3. Furthermore, adjustment of the flavor using ingredients such as seasonings is performed as the second cooking between time t3 and time t4, and tasting after adjustment of the flavor is performed as the second tasting between time t4 and time t5.

The adjustment of the flavor performed as the second cooking between time t3 and time t4 is a process performed on the basis of a result of the previous first tasting. The second tasting performed between time t4 and time t5 is a process performed to confirm the result of the previous flavor adjustment.

In the example of FIG. 7, one cooking process includes four chef's processes, but the number of chef's processes included in one cooking process is arbitrary. One chef's process can form one cooking process.

Furthermore, in the example of FIG. 7, one cooking process includes two tasting processes, but the number of tasting processes included in one cooking step may be one or the tasting process may not be included. The chef's tasting is recognized by, for example, analyzing the image captured by the camera. The chef's tasting may be recognized on the basis of the chef's biological reaction.

Figure 8:
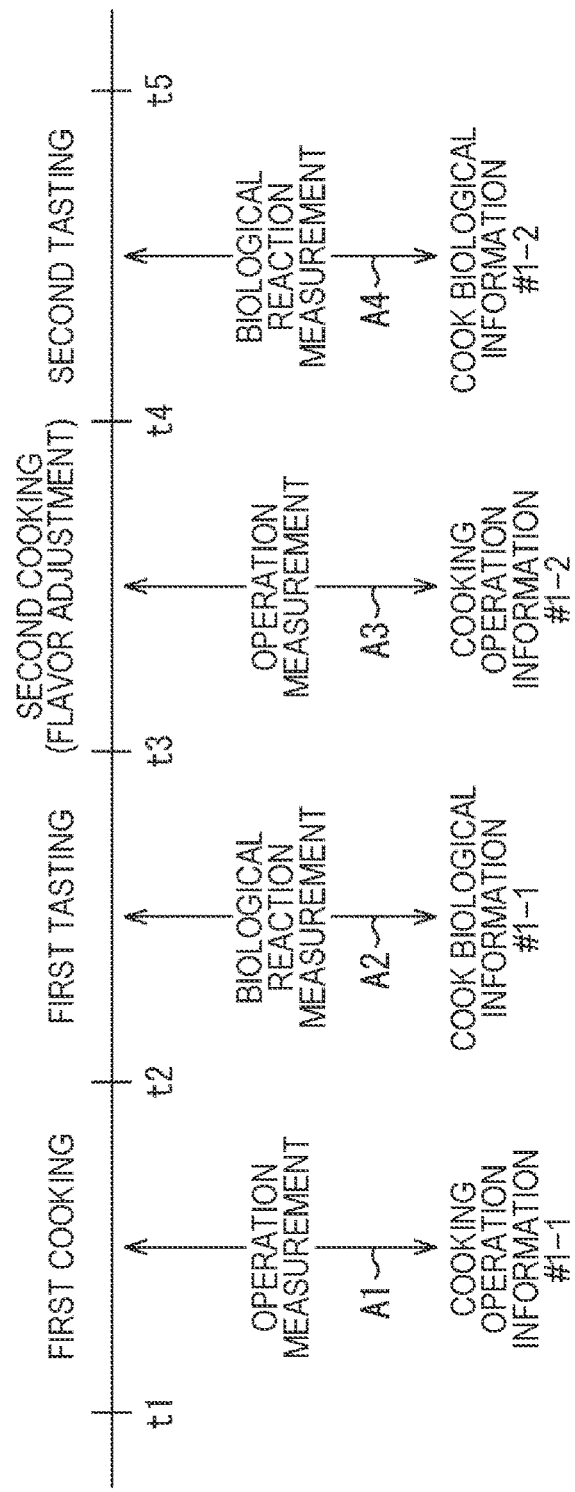
FIG. 8 is a diagram illustrating an example of generating information.

FIG. 8 is a diagram illustrating an example of generating information.

As illustrated in FIG. 8, the chef's operation is measured from time t1 to time t2 when the first cooking is performed, and the ingredients used by the chef and movement of the chef are recognized. Cooking operation information #1-1 is generated as illustrated at the tip of the arrow A1 on the basis of the recognition result between time t1 and time t2.

Furthermore, when start of tasting of the chef is recognized at time t2, measurement of the chef's biological reaction is started. The measurement of the biological reaction is continued until time t3 when end of the tasting of the chef is recognized, for example. Cook biological information #1-1 is generated as illustrated at the tip of the arrow A2 on the basis of the measurement result between time t2 and time t3.

Similarly, the chef's movement is measured from time t3 to time t4 when the second cooking is performed, and the ingredients used by the chef and the chef's movement are recognized. Cooking operation information #1-2 is generated as illustrated at the tip of the arrow A3 on the basis of the recognition result between time t3 and time t4.

In a case where start of tasting of the chef is recognized at time t4, measurement of the chef's biological reaction is started. The measurement of the biological reaction is continued until time t5 when end of the tasting of the chef is recognized, for example. Cook biological information #1-2 is generated as illustrated at the tip of the arrow A4 on the basis of the measurement result between time t4 and time t5.

For example, by combining the cooking operation information #1-1 and the cooking operation information #1-2, the cooking operation information configuring the cooking process data set of the cooking process #1 is generated.

Furthermore, by combining the cook biological information #1-1 and the cook biological information #1-2, the cook biological information configuring the cooking process data set of the cooking process #1 is generated. The cook biological information also includes information representing that the cook biological information has been generated on the basis of the chef's biological reaction in what timing of tasting. The cook biological information is linked to the tasting process.

Figure 9:
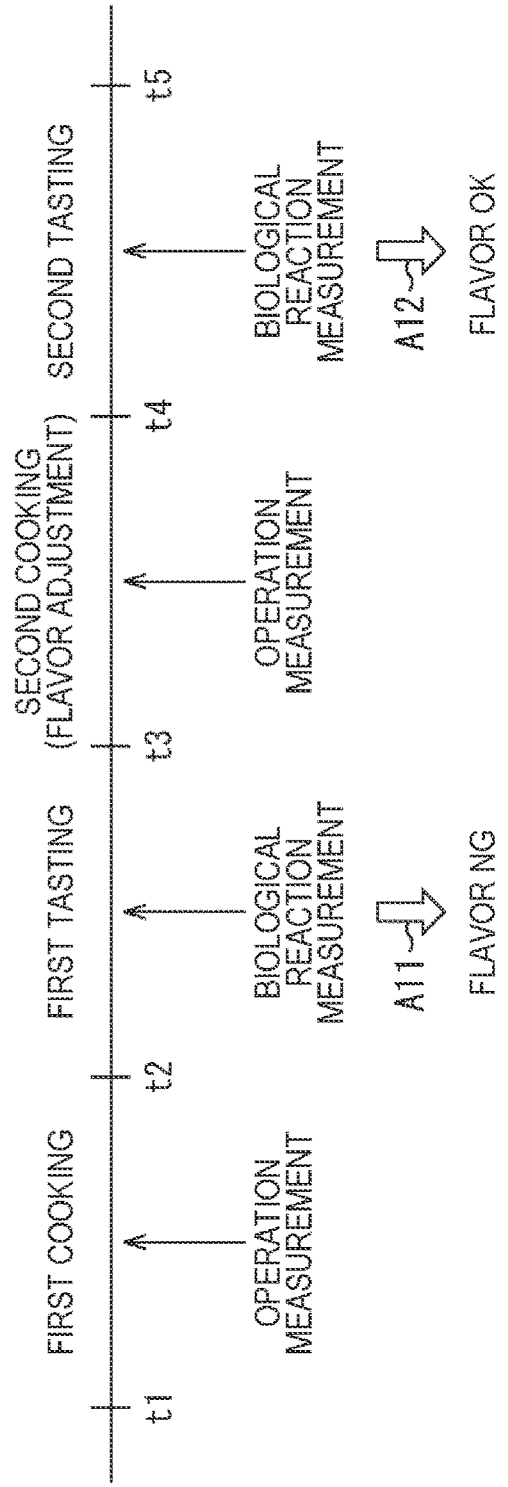
FIG. 9 is a diagram illustrating another example of generating information.

FIG. 9 is a diagram illustrating another example of generating information.

In the example of FIG. 9, the recipe data does not include the cook biological information representing all the measured biological reactions. For example, the recipe data includes only the cook biological information representing the biological reaction of when the tasting result is OK, that is, when the chef judges that the food is delicious.

Whether or not the chef judges that the eaten ingredients are delicious is directly input by the chef by pressing a button provided in the kitchen.

In addition, whether or not the chef judges that the eaten ingredients are delicious may be determined on the basis of the chef's biological reaction.

Figure 10:
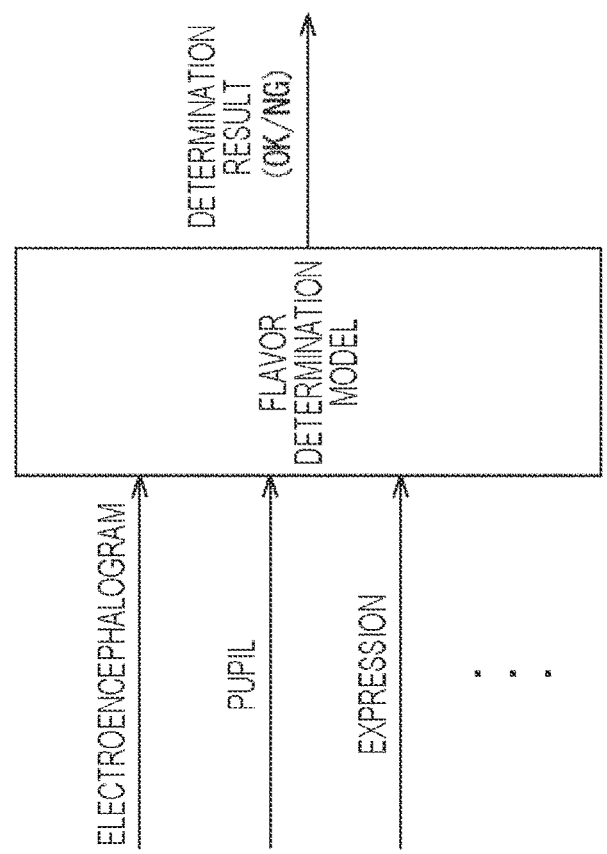
FIG. 10 is a diagram illustrating an example of a determination model used for determining a flavor.

FIG. 10 is a diagram illustrating an example of a determination model used for determining a flavor.

As illustrated in FIG. 10, whether or not the chef judges that the eaten ingredients are delicious is determined using a flavor determination model that is a model of a neural network generated by deep learning or the like. The flavor determination model is generated in advance by learning using, for example, the measurement result of the biological reaction when the chef eats a certain ingredient and information representing the way of feeling the flavor as to whether the ingredient is delicious or not delicious.

For example, in a case where the measurement result of the biological reaction when tasting a certain ingredient is input, a flavor determination result is output from the flavor determination model. The flavor determination result indicates whether the tasted ingredient is delicious (OK) or not delicious (NG).

In the example of FIG. 9, as illustrated at the tip of the arrow A11, it is determined that the result of the first tasting performed between time t2 and time t3 is not delicious. Meanwhile, as illustrated at the tip of the arrow A12, it is determined that the result of the second tasting performed between time t4 and time t5 is delicious.

In this case, the cook biological information #1-2 generated on the basis of the measurement result between time t4 and time t5 is included in the cooking process data set of the cooking process #1 together with the cooking operation information generated as described with reference to FIG. 8.

In this way, the recipe data may include only the cook biological information representing the biological reaction satisfying a predetermined condition, which is considered to be delicious by the chef.

In a case where all pieces of cook biological information are included in the recipe data as described with reference to FIG. 8, a flavor OK flag may be set to the cook biological information #1-2 representing the biological reaction of when the chef judges that the eaten ingredient is delicious. The flavor OK flag is a flag indicating that the chef judges that the eaten ingredient is delicious.

By referring to the flavor OK flag, the reproduction side can specify the timing of tasting when the chef has judged that the ingredient is delicious.

Note that, in the examples of FIGS. 8 and 9, the biological reaction is measured only while the chef is tasting, but the biological reaction may be measured on a steady basis while the chef is cooking. In this case, the recipe data includes time-series data of the biological reaction from the start to the end of cooking by the chef as the cook biological information.

As described above, the recipe data is configured by linking (associating) the cooking operation information that is the information regarding the cooking operation for realizing the cooking process to (with) the cook biological information that is information representing the biological reaction of the chef measured in conjunction with the progress of the cooking process.

Figure 11:
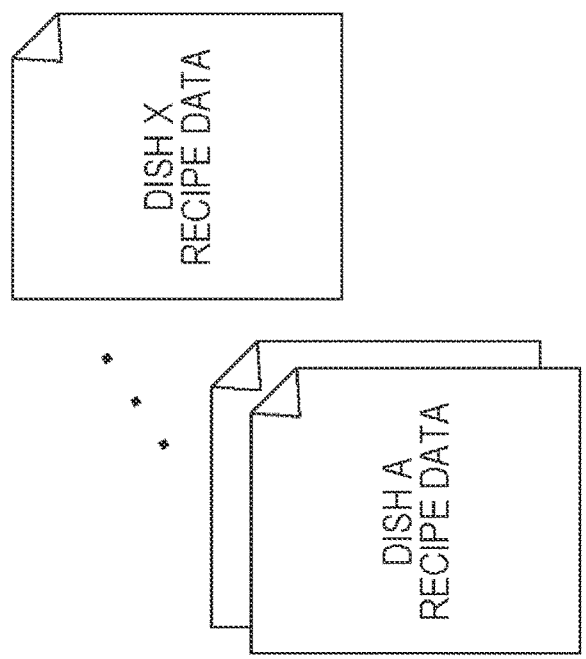
FIG. 11 is a diagram illustrating an example of recipe data.

The recipe data including each of the above information is prepared for each dish as illustrated in FIG. 11. Which recipe data is used to reproduce the dish is selected by, for example, the eater at a place where the cooking robot 1 is installed.

<Example of Flow of Generation of Recipe Data and Reproduction of Dish>

Figure 12:
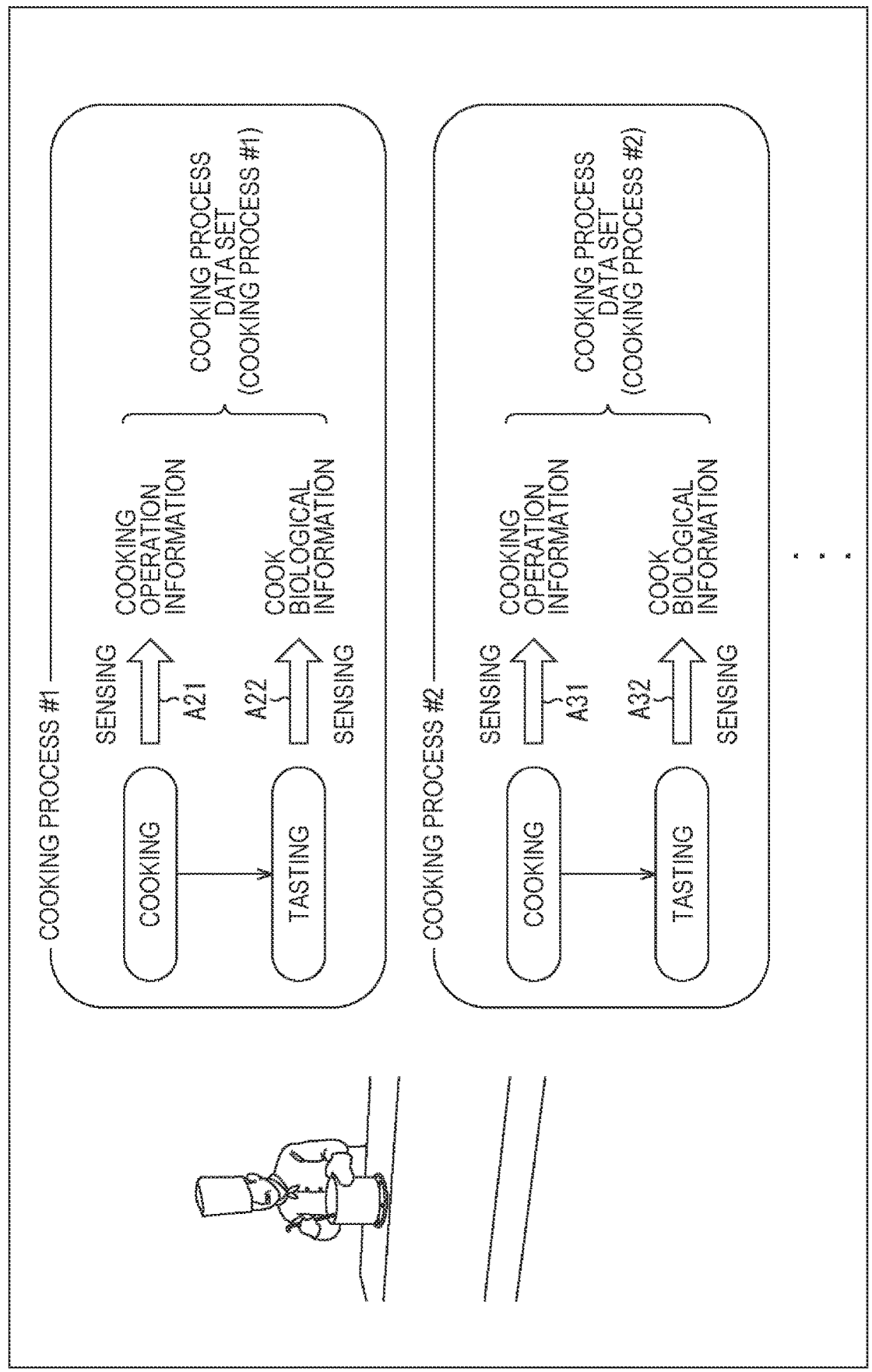
FIG. 12 is a diagram illustrating an example of a flow of generating the recipe data.

FIG. 12 is a diagram illustrating an example of a flow of generating the recipe data.

As described above, the cooking operation information configuring the cooking process data set is generated on the basis of sensing results by sensing (measuring) the operation of the chef who is cooking.

Furthermore, the cook biological information is generated on the basis of sensing results by sensing the biological reaction of the chef who is tasting.

In the example of FIG. 12, as illustrated by the arrows A21, the cooking operation information configuring the cooking process data set of the cooking process #1 is generated on the basis of the sensing results of the cooking operation performed by the chef as the cooking process #1.

Furthermore, as illustrated by the arrow A22, the cook biological information configuring the cooking process data set of the cooking process #1 is generated on the basis of the sensing results of the biological reaction of the chef who is testing the cooked ingredient.

After the cooking process #1 is completed, the cooking process #2, which is the next cooking process" is performed.

Similarly, as illustrated by the arrows A31, the cooking operation information configuring the cooking process data set of the cooking process #2 is generated on the basis of the sensing results of the cooking operation performed by the chef as the cooking process #2.

Furthermore, as illustrated by the arrow A32, the cook biological information configuring the cooking process data set of the cooking process #2 is generated on the basis of the sensing results of the biological reaction of the chef who is testing the cooked ingredient.

One dish is completed through such a plurality of cooking processes. Furthermore, as the dish is completed, the recipe data describing the cooking process data set of each cooking process is generated.

Figure 13:
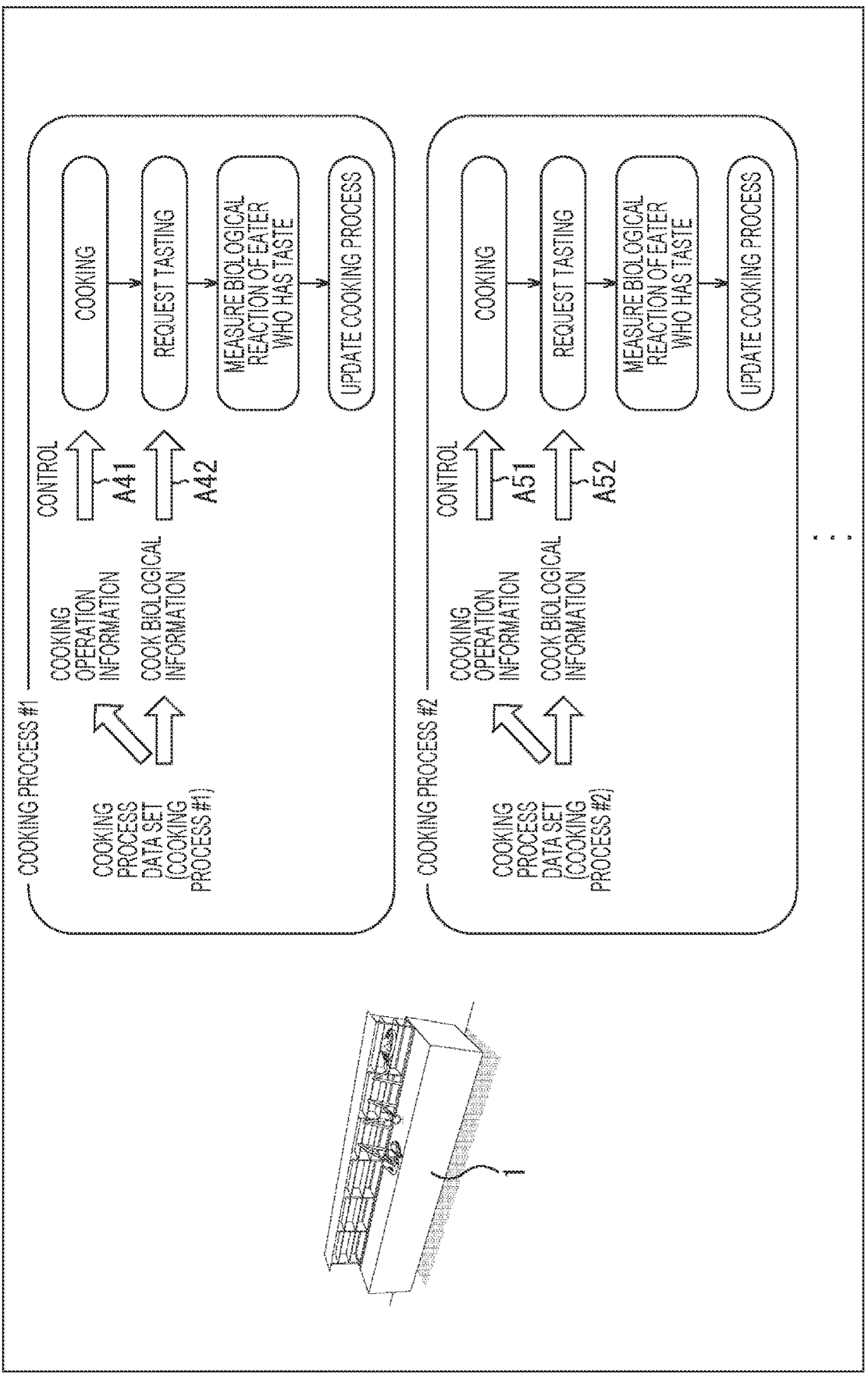
FIG. 13 is a diagram illustrating an example of a flow of reproducing a dish based on the recipe data.

FIG. 13 is a diagram illustrating an example of a flow of reproducing a dish based on the recipe data.

As illustrated in FIG. 13, the reproduction of a dish by the cooking robot 1 is performed by repeating, for each cooking process, cooking on the basis of the cooking operation information included in the cooking process data set described in the recipe data, and updating the cooking process according to the biological reaction of the eater who has tasted the cooked ingredient.

The tasting of the cooked ingredient is performed by the eater, for example, in response to a request from the cooking robot 1 to the eater to taste the cooked ingredient. The eater will be around the cooking robot 1 that is cooking on the basis of the recipe data so that the eater can have a taste in response to the request of the cooking robot 1.

The request for tasting is performed by, for example, outputting a synthetic voice from a speaker of the cooking robot 1 or by blinking a light emitting unit such as an LED provided in the cooking robot 1. The request for tasting may be performed by transmitting a message to a mobile terminal such as a smartphone of the eater.

The timing of requesting tasting is determined according to the timing of tasting when the chef judges that the food is delicious on the basis of the cook biological information included in the cooking process data set, for example.

In the example of FIG. 13, as illustrated by the arrow A41, the cooking operation of the cooking robot 1 is controlled on the basis of the cooking operation information configuring the cooking process data set of the cooking process #1, and an operation same as the operation of the cooking process #1 of the chef is performed by the cooking robot 1.

After an operation same as the operation of the chef's cooking process #1 is performed by the cooking robot 1, the eater is required to have a taste for the cooked ingredient, as illustrated by the arrow A42. This request for tasting is performed on the basis of the cook biological information representing the biological reaction of when the chef judges that the ingredient is delicious.

The biological reaction of the eater who is tasting is measured in response to the request by the cooking robot 1, and the cooking process is updated on the basis of the measurement result. Although details will be described below, the cooking process is updated so that the cooked ingredient becomes delicious in a case where the eater feels that the cooked ingredient is not delicious.

In a case where cooking according to the updated cooking process is performed by the cooking robot 1, the cooking process #1 is terminated. After the cooking process #1 is completed, the cooking process #2, which is the next cooking process" is performed.

Similarly, as illustrated by the arrow A51, the cooking operation of the cooking robot 1 is controlled on the basis of the cooking operation information configuring the cooking process data set of the cooking process #2, and an operation same as the operation of the cooking process #2 of the chef is performed by the cooking robot 1.

After an operation same as the operation of the chef's cooking process #2 is performed by the cooking robot 1, the eater is required to have a taste for the cooked ingredient, as illustrated by the arrow A52. This request for tasting is performed on the basis of the cook biological information representing the biological reaction of when the chef judges that the ingredient is delicious.

The biological reaction of the eater who is tasting is measured in response to the request by the cooking robot 1, and the cooking process is updated on the basis of the measurement result.

In a case where cooking according to the updated cooking process is performed by the cooking robot 1, the cooking process #2 is terminated.

Through such a plurality of cooking processes, the dish made by the chef is reproduced by the cooking robot 1.

Figure 14:
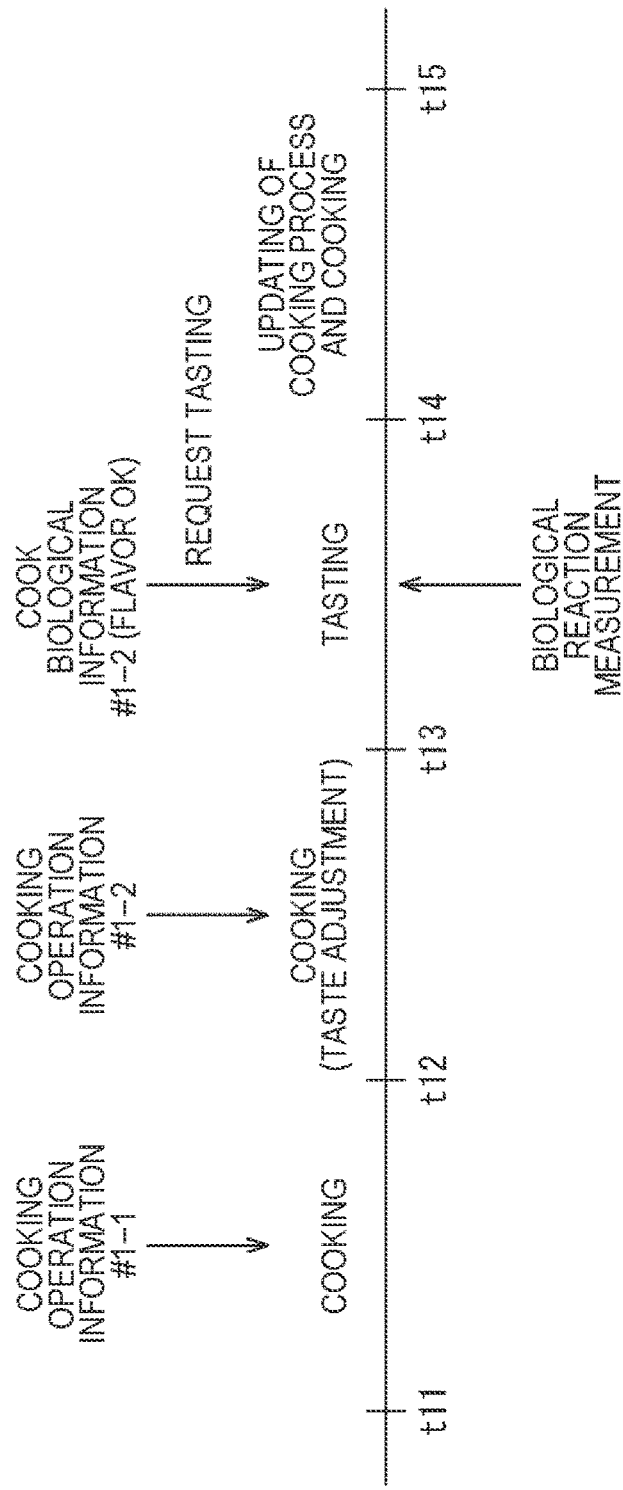
FIG. 14 is a diagram illustrating an example of a cooking process at the time of reproduction.

FIG. 14 is a diagram illustrating an example of a cooking process at the time of reproduction.

It is assumed that the cooking process #1 described with reference to FIG. 8 is performed by the chef and the cooking process data set described above is generated.

As illustrated in FIG. 14, cooking same as the first cooking performed by the chef during time t1 to time t2 (FIG. 8) is performed by the cooking robot 1 on the basis of the cooking operation information #1-1 included in the cooking process data set during time t1/ to time t12.

Furthermore, cooking same as the second cooking performed by the chef during time t3 to time t4 is performed by the cooking robot 1 on the basis of the cooking operation information #1-2 included in the cooking process data set during time t12 to time t13.

Thereby, two cookings having the same content as the two cookings performed by the chef have been performed by the cooking robot 1.

At time t13 when cooking based on the cooking operation information #1-2 is completed, the ingredient with flavor adjusted by the chef, that is, the ingredient with the same flavor as the ingredient obtained at time t4 in FIG. 8 are prepared on the cooking robot 1 side as the cooked ingredient.

Since the ingredient has been judged to be delicious in the second tasting performed after the second cooking on the chef side, the eater is required to have a taste at timing after the corresponding second cooking on the reproduction side. The chef having judged that the ingredient is delicious in the second tasting is determined on the basis of the cook biological information #1-2. As described above, the cook biological information #1-2 is information generated on the basis of the biological reaction at the time when the chef has judged that the ingredient is delicious.

In the example of FIG. 14, the eater is required to have a taste at time t13. The eater will taste the ingredient in response to the request from the cooking robot 1.

In a case where start of tasting of the eater is recognized, measurement of the eater's biological reaction is started. The biological reaction of the eater to be measured is similar to the biological reaction of the chef. The electroencephalogram, pupil, sweating, electromyogram of limbs, the temperature of the whole face, facial expression, motion of the whole body, heart rate, and voice of the eater are measured. The measurement of the biological reaction is continued until time t14 when end of the tasting of the eater is recognized, for example.

Whether or not the eater judges that the ingredient is delicious is determined on the basis of the measurement result between time t13 and time t14. That is, whether or not the eater also judges that the cooked ingredient is delicious is determined, which has been judged to be delicious by the chef.

Whether or not the eater judges that the eaten ingredient is delicious is directly input by the eater by pressing a button provided in the cooking robot 1.

Whether or not the eater judges that the eaten ingredient is delicious may be determined on the basis of the eater's biological reaction.

Whether or not the eater judges that the eaten ingredient is delicious is also determined using a flavor determination model as described with reference to FIG. 10. The flavor determination model prepared on the reproduction side is a model generated by learning using the measurement results of the biological reaction when the eater eats a certain ingredient.

In a case where the eater judges that the eaten ingredient is delicious, the cooking process #1 is terminated.

Meanwhile, in a case where the eater judges that the eaten ingredient is not delicious, the cooking process is updated between time t14 and time t15, and cooking according to the updated cooking process is performed by the cooking robot 1. The cooking process is updated on the basis of the biological reaction of the eater who has had a taste.

Figure 15:
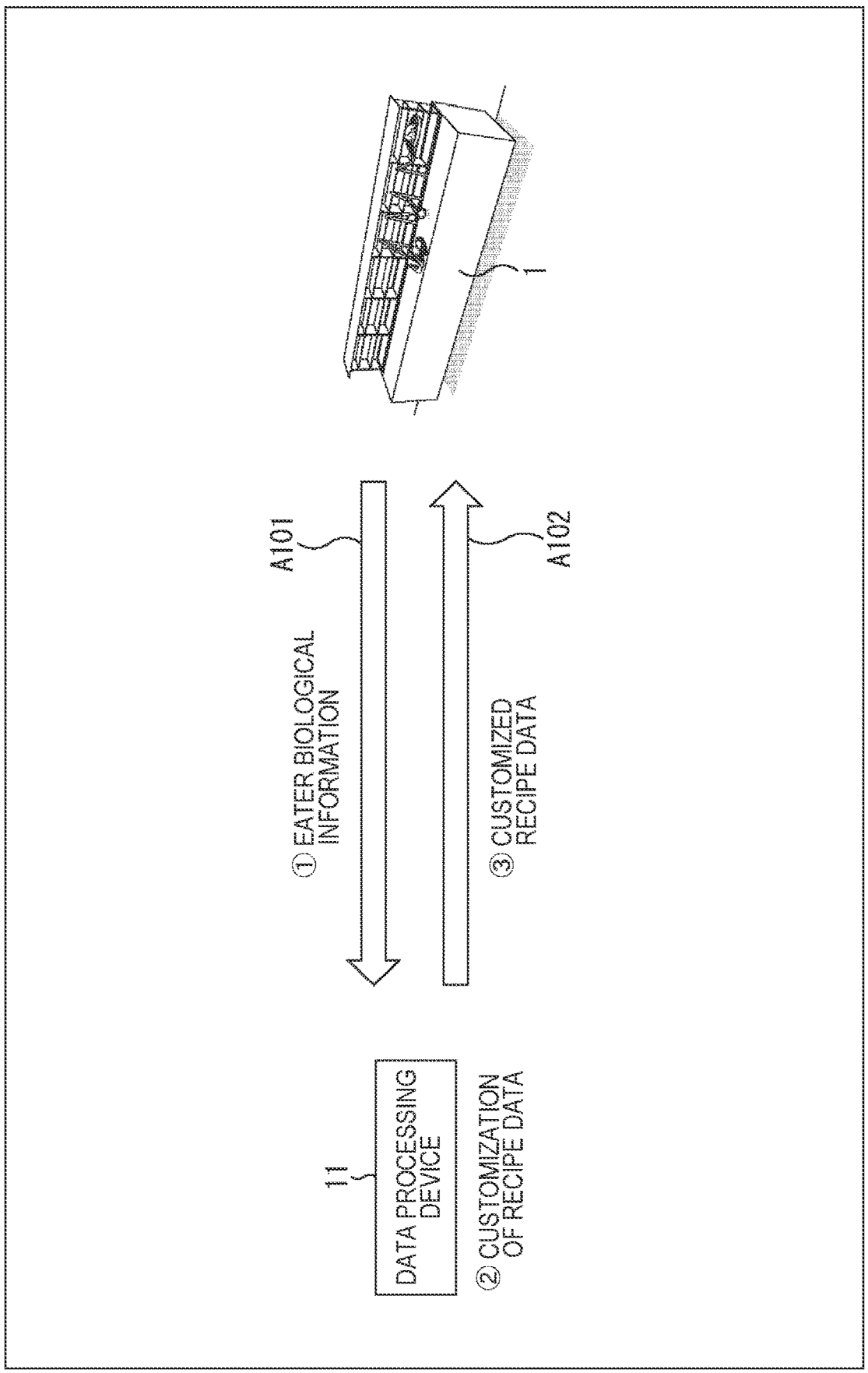
FIG. 15 is a diagram illustrating an example of a flow of customizing recipe data.

FIG. 15 is a diagram illustrating an example of a flow of customizing recipe data, including updating the cooking process.

The data processing device 11 illustrated in FIG. 15 is a device having a function to generate the recipe data and provide the recipe data to the reproduction side including the cooking robot 1, as will be described below in detail.

As illustrated by the arrow A101, the cooking robot 1 transmits the eater biological information representing the biological reaction of the eater who has had a taste to the data processing device 11.

In the data processing device 11, the recipe data is customized by updating the cooking process on the basis of the eater biological information. For example, how the eater feels the flavor of the ingredient to be tasted is analyzed on the basis of the eater biological information.

Figure 16:
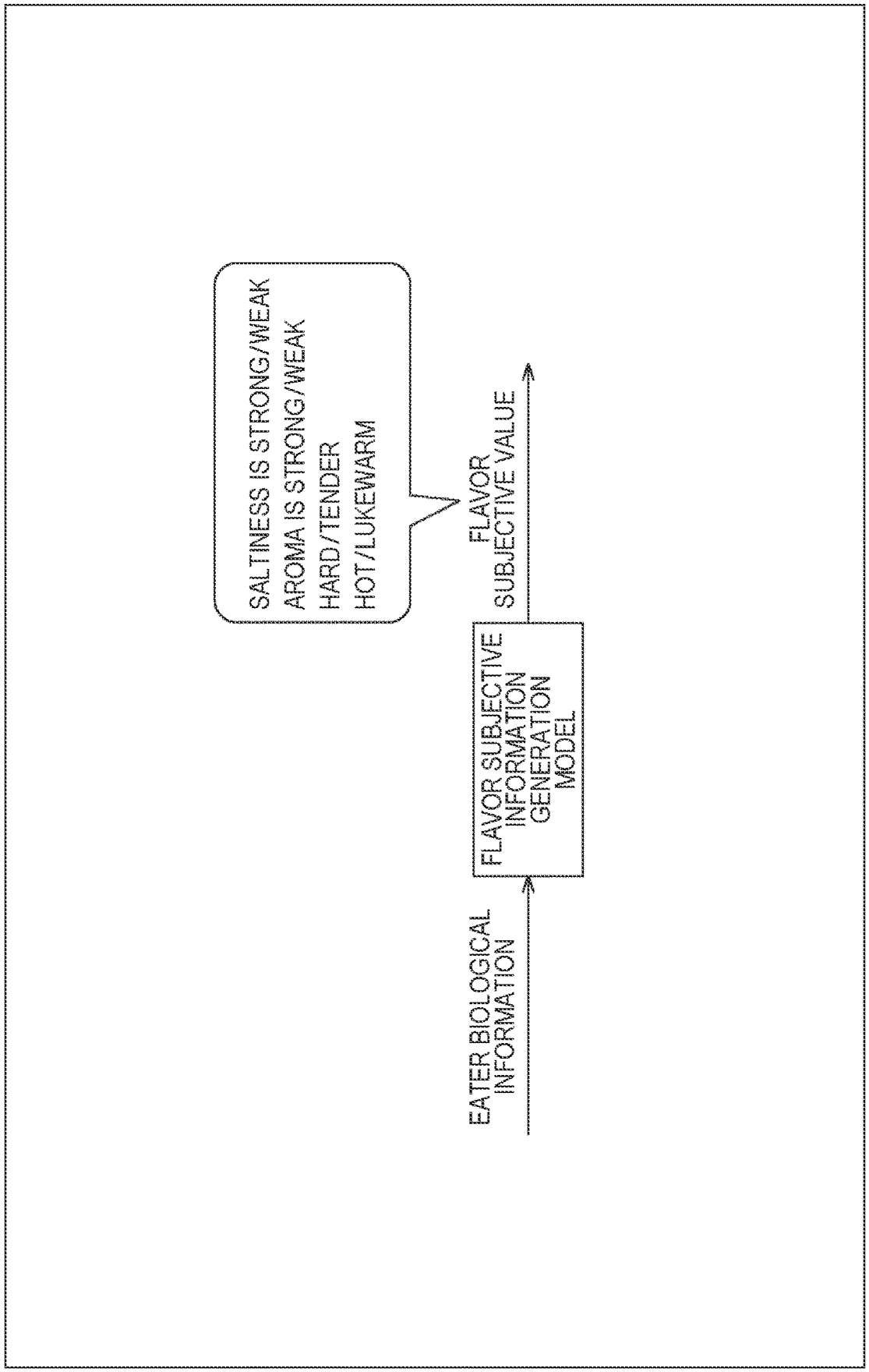
FIG. 16 is a diagram illustrating an example of an analysis of how an eater feels a flavor.

FIG. 16 is a diagram illustrating an example of an analysis of how an eater feels a flavor.

As illustrated in FIG. 16, the flavor subjective value, which is how the eater feels the flavor, is calculated by inputting the eater's biological information into the flavor subjective information generation model prepared in the data processing device 11. A flavor subjective information generation model is a model generated in advance by learning using the biological reaction of the eater and information representing how the eater feels the flavor.

According to flavor subjective values calculated on the basis of the eater biological information, for example, the subjective feeling of the eater regarding the flavor is expressed by delicious/not delicious, the saltiness is strong/weak, the sweetness is strong/weak, the aroma is strong/weak, hard/tender, hot/lukewarm, and the like.

In a case where the eater feels that the saltiness is weak, for example, the data processing device 11 updates the cooking process so as to add an action of sprinkling salt to the ingredient in order to strengthen the saltiness.

In a case where the eater feels that the ingredient is hard, the data processing device 11 updates the cooking process so as to add an operation of simmering the ingredient for a predetermined time to make the ingredient tender.

Furthermore, in a case where the eater feels that the ingredient is lukewarm, the data processing device 11 updates the cooking process so as to add an operation of heating the ingredient for a predetermined time to make the ingredient hot.

The customized recipe data, including the description of the updated cooking process, is provided to the cooking robot 1 as illustrated by the arrow A102 in FIG. 15. In the cooking robot 1, the ingredient is cooked according to the updated cooking process.

Such tasting request and cooking process update are repeated until the eater judges that the cooked ingredient is delicious, for example.

As described above, the reproduction side including the cooking robot 1 proceeds with cooking while checking, for each cooking process, whether or not the eater judges the cooked ingredient is delicious, the cooked ingredient having been obtained by performing the operation same as the operation of the chef.

Figure 17:
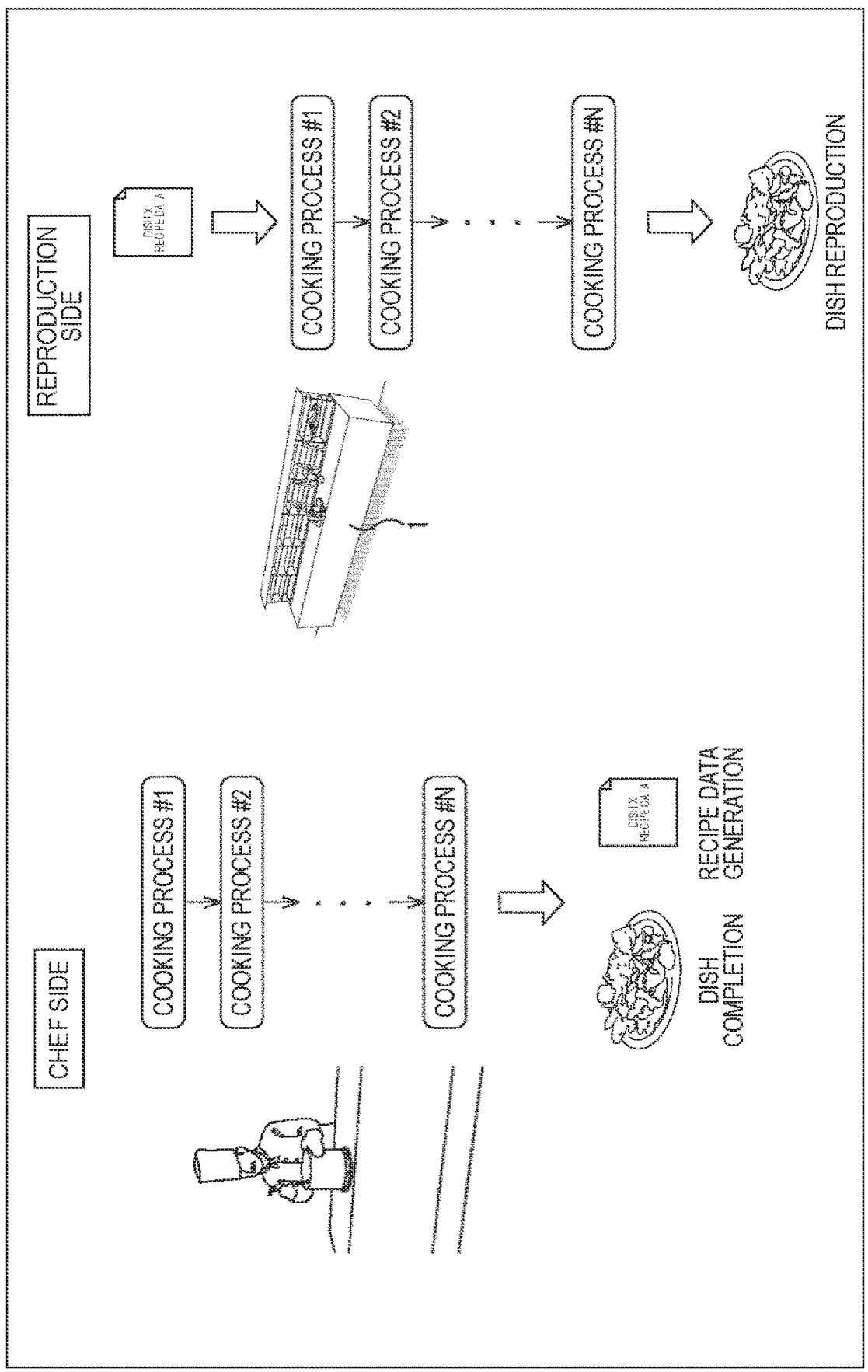
FIG. 17 is a diagram illustrating a flow on the chef side and a flow on the reproduction side together.

FIG. 17 is a diagram illustrating a flow on the chef side and a flow on the reproduction side together.

As illustrated on the left side of FIG. 17, one dish is completed through a plurality of cooking processes #1 to #N, and the recipe data describing the cooking process data set of each cooking process is generated.

Meanwhile, on the reproduction side, one dish is reproduced through a plurality of cooking processes #1 to #N that is the same as the cooking processes performed on the chef side on the basis of the recipe data generated by the cooking of the chef.

The cooking by the cooking robot 1 proceeds while checking, for each cooking process, whether or not the eater feels delicious similarly to the way the chef feels, and updating the cooking process so that the eater can feel delicious. Therefore, the final dish becomes a dish that the eater feels delicious.

Basically, the dish has been made through the same cooking as the cooking by the chef, the final dish becomes a dish with flavor customized according to the preference of the eater although the dish is reproduction of the dish made by the chef.

The chef can serve the dish same as the dish made by the chef to a person who cannot visit the chef's own restaurant. In addition, the chef can leave the dishes made by the chef in a reproducible form as the recipe data.

Meanwhile, the person who eats the dish reproduced by the cooking robot 1 can customize the dish same as the dish prepared by the chef according to its preference.

<Modification of Description of Recipe Data>

Figure 18:
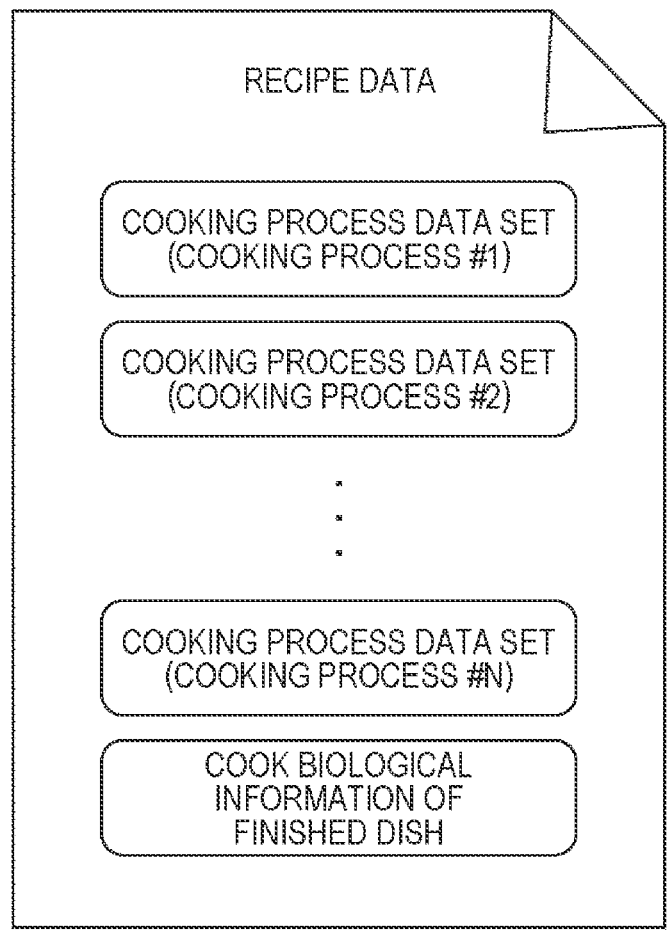
FIG. 18 is a diagram illustrating an example of another description content of the recipe data.

FIG. 18 is a diagram illustrating an example of another description content of the recipe data.

As illustrated in FIG. 18, the recipe data may include the cook biological information representing the biological reaction of the chef who has tasted the finished dish. In this case, the cook biological information is linked to the entire cooking operation information.

In this way, the associated relationship between the cooking operation information and the cook biological information does not have to be one-to-one.

For example, in the case where the recipe data includes the cook biological information representing the biological reaction of the chef who has tasted the finished dish, the customization of the recipe data is performed at timing after eating on the basis of the biological reaction of the eater who is eating the reproduced dish after the reproduction of the dish by the cooking robot 1 is completed. The recipe data customized on the basis of the biological reaction measured during eating will be used when the same dish is reproduced in the cooking robot 1 again.

Figure 19:
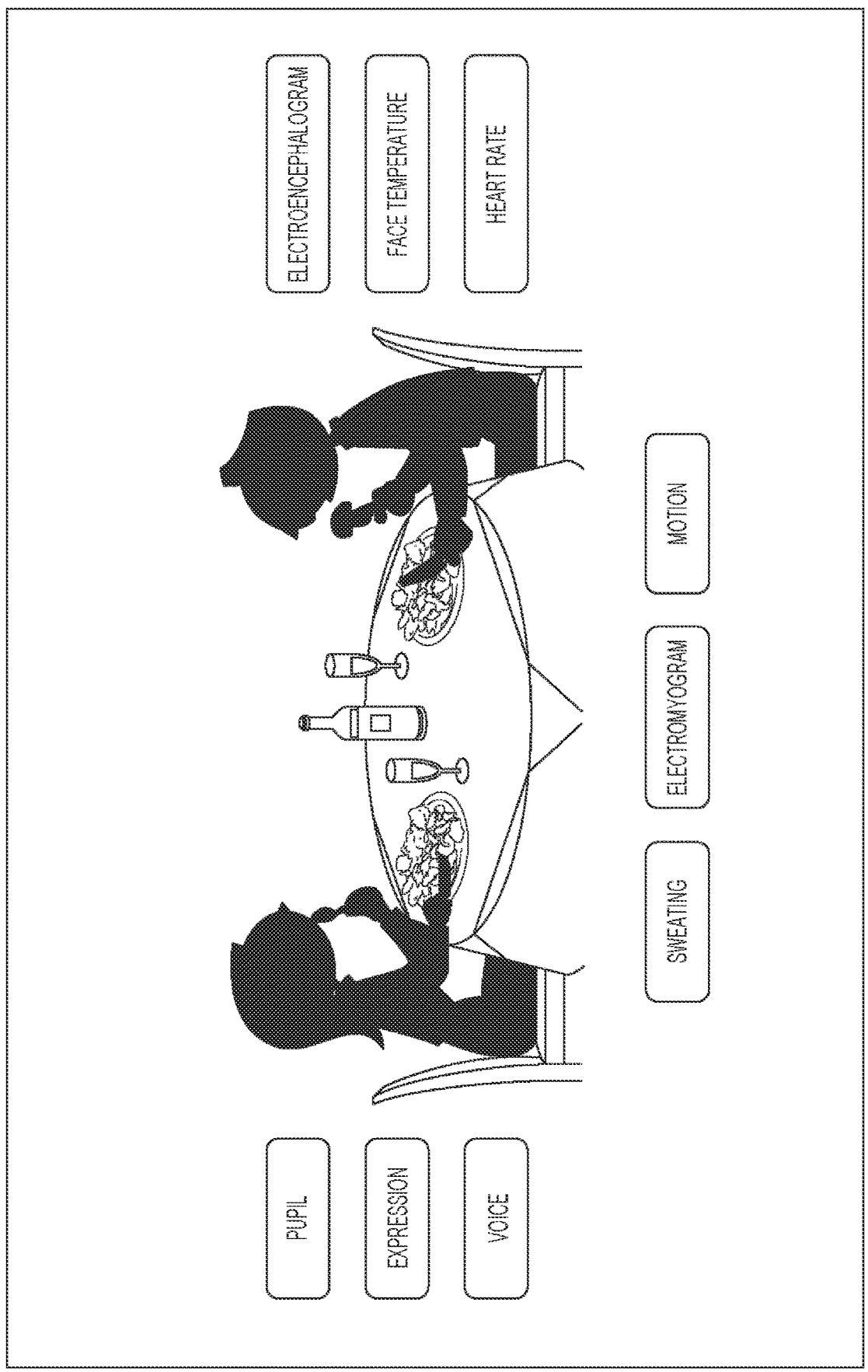
FIG. 19 is a diagram illustrating an example of a biological reaction to be measured.

FIG. 19 is a diagram illustrating an example of a biological reaction to be measured.

The two persons illustrated in FIG. 19 are eaters who are eating the dish reproduced by the cooking robot 1. As illustrated in FIG. 19, for example, the electroencephalogram, pupil, sweating, electromyogram of limbs, the temperature of the whole face, facial expression, motion of the whole body, heart rate, and voice of the eaters are measured, and the eater biological information is generated.

The eater biological information measured during eating is information representing how the eater feels the flavor of the dish reproduced by the cooking robot 1.

Figure 20:
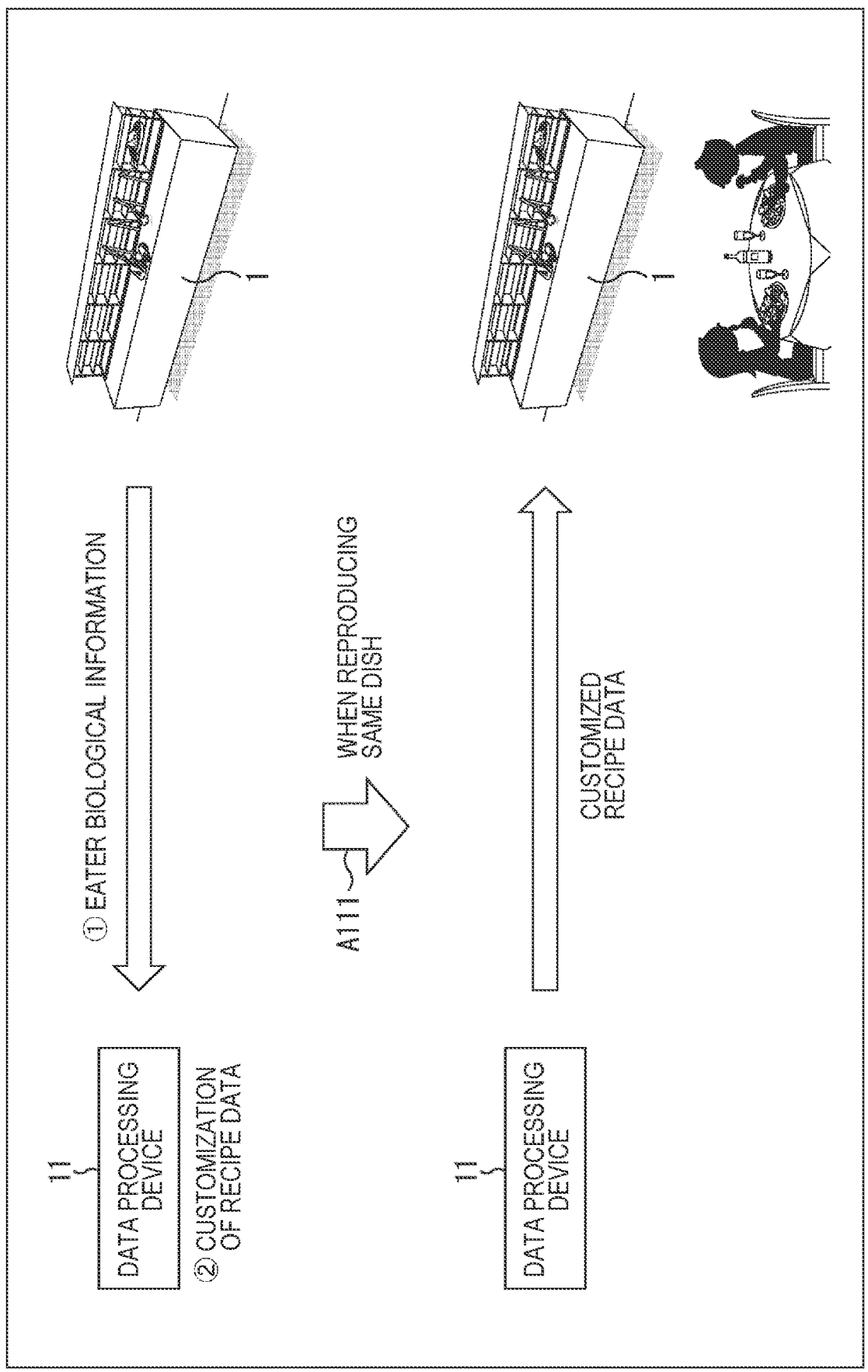
FIG. 20 is a diagram illustrating an example of a flow of customizing recipe data.

FIG. 20 is a diagram illustrating an example of a flow of customizing recipe data.

As illustrated in the upper part of FIG. 20, the cooking robot 1 transmits the eater biological information representing the biological reaction of the eater who is eating to the data processing device 11.

In the data processing device 11, the recipe data is customized by updating the cooking process on the basis of the eater biological information. As described above, the customization of the recipe data is performed on the basis of a flavor subjective value that indicates the way the eater feels the flavor by analyzing how the eater feels the flavor of the dish on the basis of the eater biological information.

In a case where the eater feels that the saltiness is weak, for example, the data processing device 11 updates the cooking process so as to add an action of sprinkling salt to the ingredient at predetermined timing in order to strengthen the saltiness.

In a case where the eater feels that the dish is hard, the data processing device 11 updates the cooking process so as to add an operation of simmering the ingredient at predetermined timing for a predetermined time to make the dish tender.

Furthermore, in a case where the eater feels that the dish is lukewarm, the data processing device 11 updates the cooking process so as to add an operation of heating the ingredient at predetermined timing for a predetermined time to heat the dish.

In a case where making the same dish is selected by the eater, as illustrated as the tip of the arrow A111, the customized recipe data, including the description of the updated cooking process, is provided to the cooking robot 1. The cooking robot 1 cooks according to the updated cooking process.

The flavor of the dish reproduced on the basis of the customized recipe data becomes the flavor according to the preference of the eater.

Figure 21:
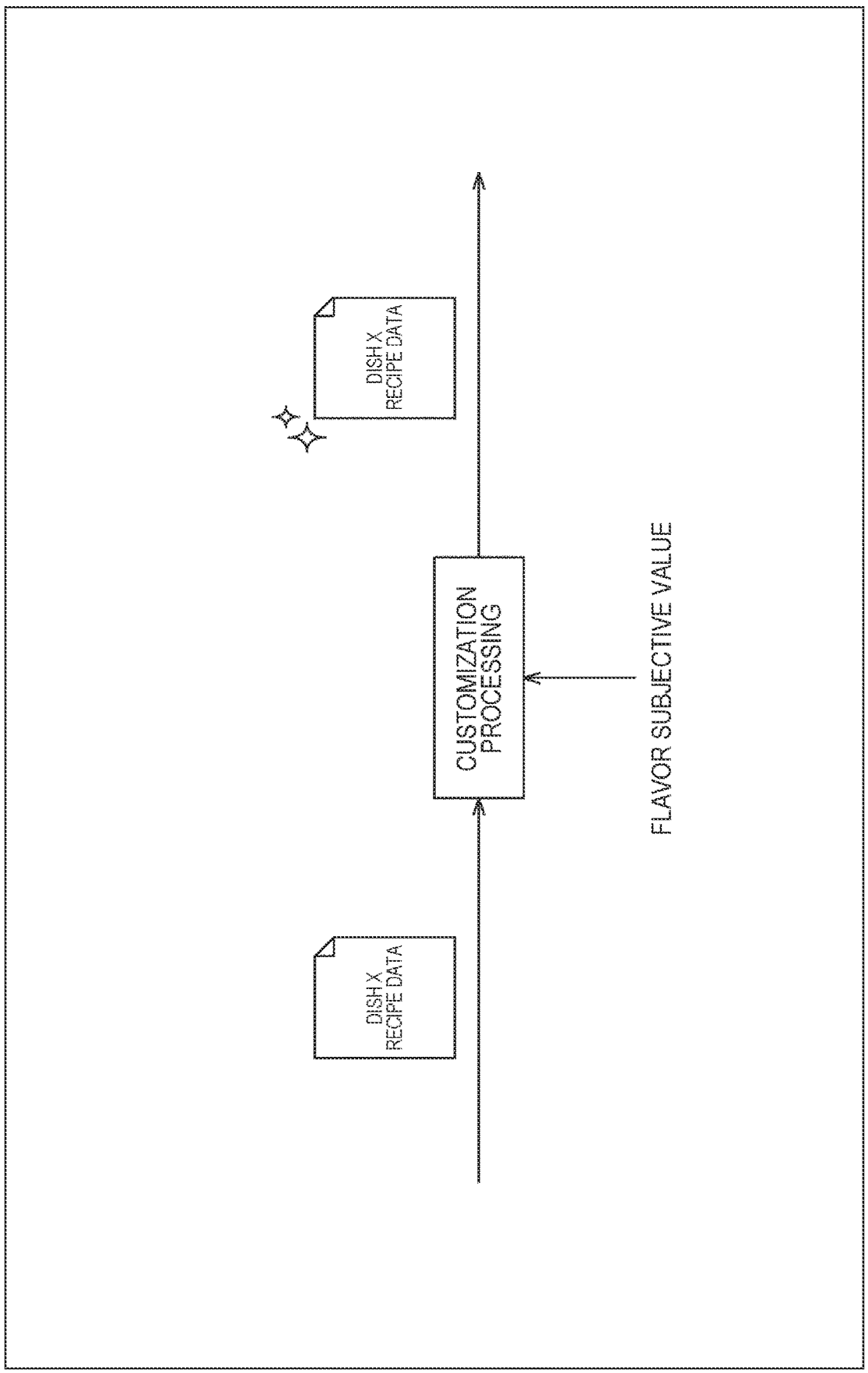
FIG. 21 is a diagram illustrating an example of customization.

As illustrated in FIG. 21, the cooking system illustrated in FIG. 20 is a system that customizes certain recipe data on the basis of the flavor subjective value indicating the way the eater feels the flavor, who has had the dish reproduced on the basis of the recipe data, and provides the customized recipe data.

Figure 22:
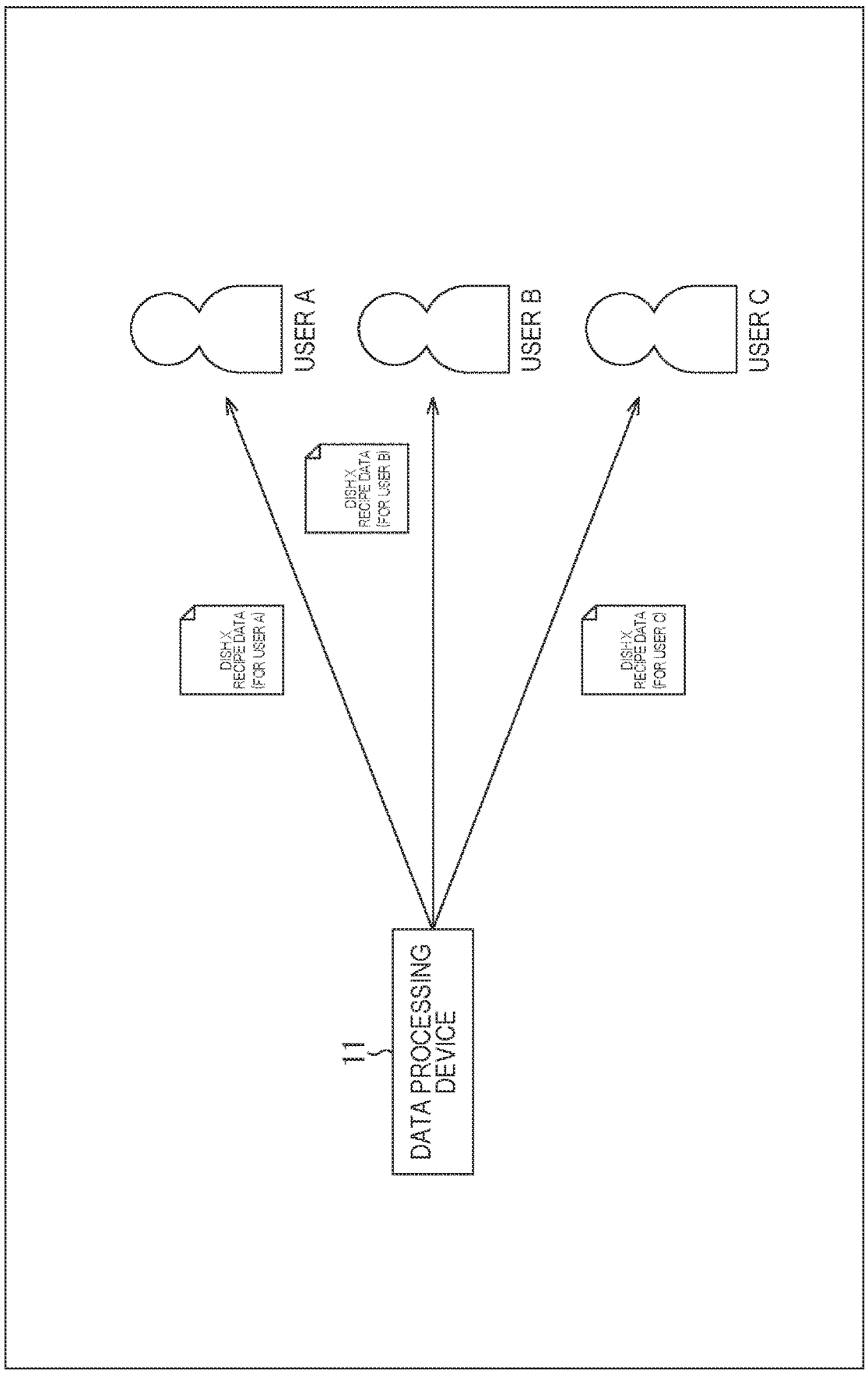
FIG. 22 is a diagram illustrating an application example of a cooking system.

FIG. 22 is a diagram illustrating an application example of a cooking system.

As illustrated in FIG. 22, the data processing device 11 can generate a plurality of recipe data by customizing the recipe data according to the preference of each of a plurality of eaters on the basis of one recipe data, and provide the recipe data to the respective eaters.

In the example of FIG. 22, certain recipe data is customized on the basis of the flavor subjective value indicating the way each of users A to C feels the flavor, who is a eater having had the dish reproduced on the basis of the certain recipe data.

The recipe data for user A customized according to the preference of the user A is provided to the user A, and the recipe data for user B customized according to the preference of the user B is provided to the user B. The recipe data for user C customized according to the preference of the user C is provided to the user C.

As described above, the above-described technique can be applied to the cooking system that provides recipe data customized for each eater.

Figure 23:
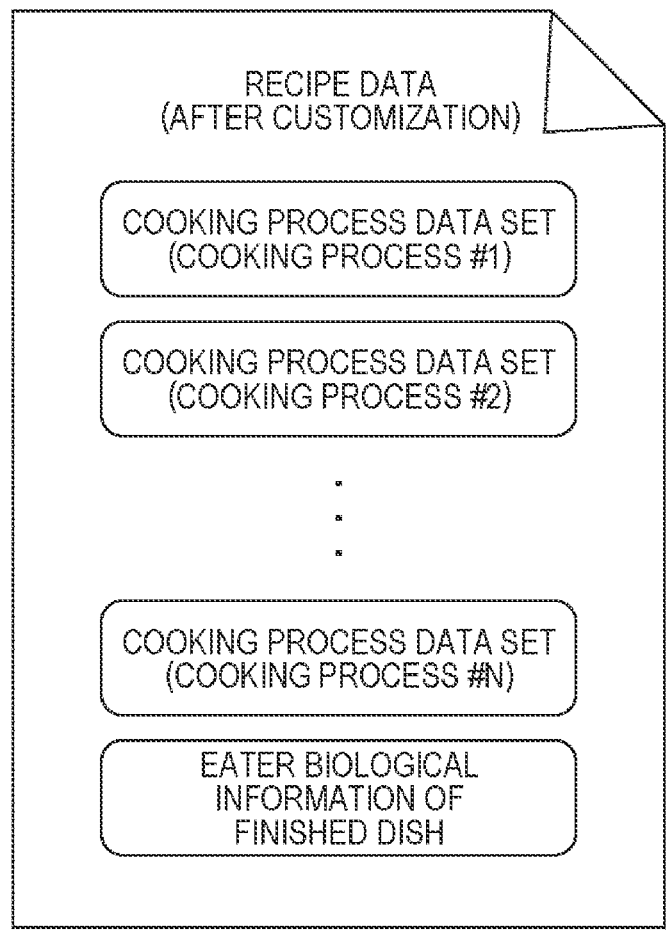
FIG. 23 is a diagram illustrating an example of another description content of the recipe data.

FIG. 23 is a diagram illustrating an example of another description content of the recipe data.

As illustrated in FIG. 23, the eater biological information may be included in the customized recipe data in place of the cook biological information. The eater biological information included in the recipe data is the information transmitted from the reproduction side as described above as information measured during eating.

In the case of reproducing the dish on the basis of the customized recipe data, the cooking proceeds using the eater biological information included in the recipe data, as appropriate.

The recipe data may include both the cook biological information and the eater biological information, instead of including the eater biological information in place of the cook biological information.

<Configuration Example of Cooking System>
(1) Overall Configuration

Figure 24:
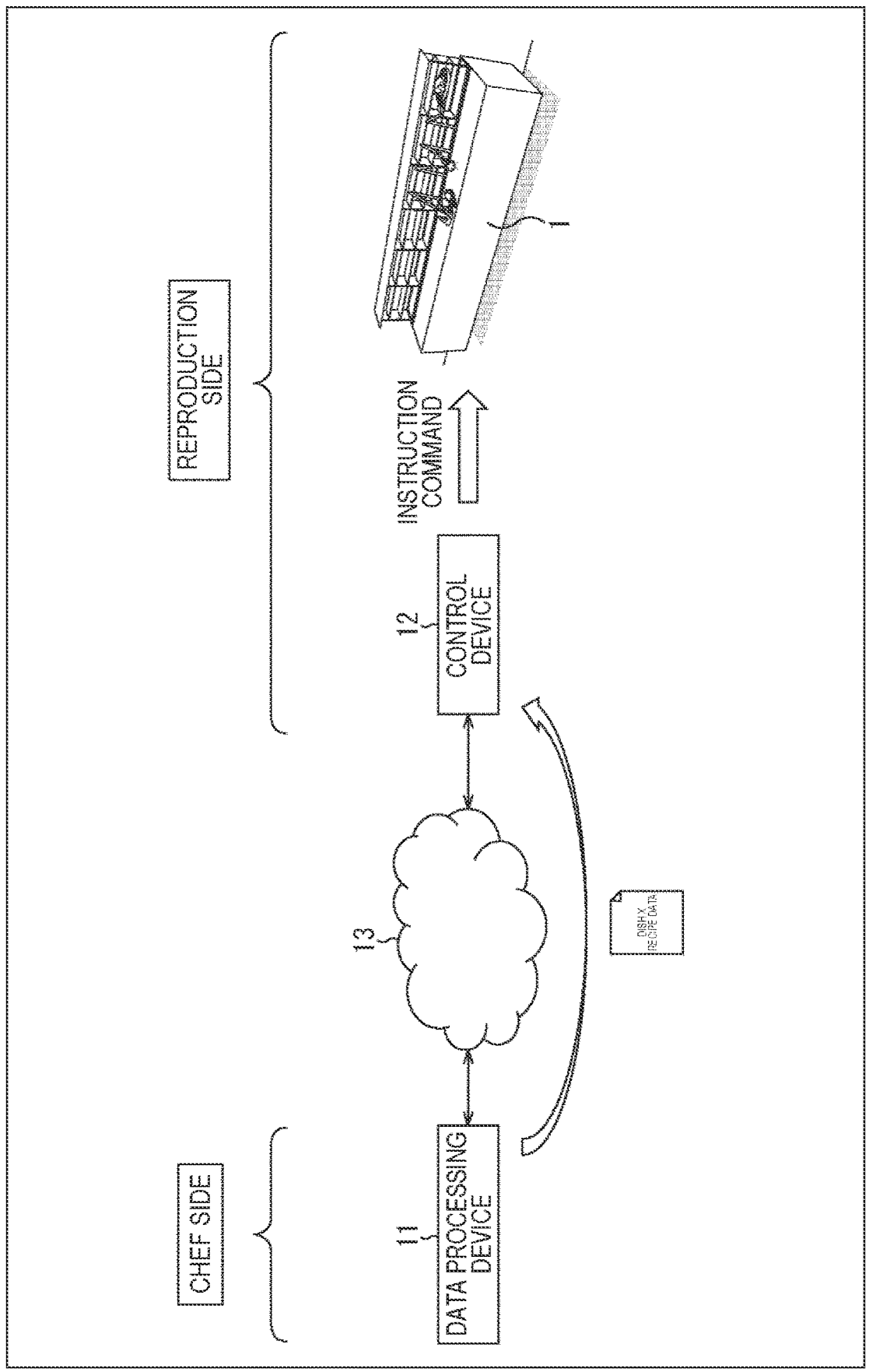
FIG. 24 is a diagram illustrating a configuration example of a cooking system according to an embodiment of the present technology.

FIG. 24 is a diagram illustrating a configuration example of a cooking system according to an embodiment of the present technology.

As illustrated in FIG. 24, the cooking system is configured by connecting a data processing device 11 provided as the chef-side configuration and a control device 12 provided as the reproduction-side configuration via a network 13 such as the Internet. As described above, the cooking system is provided with a plurality of such chef-side configurations and reproduction-side configurations.

The data processing device 11 is a device that generates the above-described recipe data. The data processing device 11 is configured by a computer or the like. The data processing device 11 transmits, for example, the recipe data of a dish selected by an eater who eats a reproduced dish to the control device 12 via the network 13.

The control device 12 is a device that controls the cooking robot 1. The control device 12 is also configured by a computer or the like. The control device 12 receives the recipe data provided by the data processing device 11 and outputs an instruction command on the basis of the description of the recipe data to control the cooking operation of the cooking robot 1.

The cooking robot 1 drives each part such as the cooking arm according to the instruction command supplied from the control device 12 to perform a cooking operation of each cooking process. The instruction command includes torque of a motor provided in the cooking arm, a driving direction, information for controlling a driving amount, and the like.

Until the cooking is completed, the control device 12 sequentially outputs the instruction commands to the cooking robot 1. The dish is finally completed as the cooking robot 1 performs operations according to the instruction commands.

Figure 25:
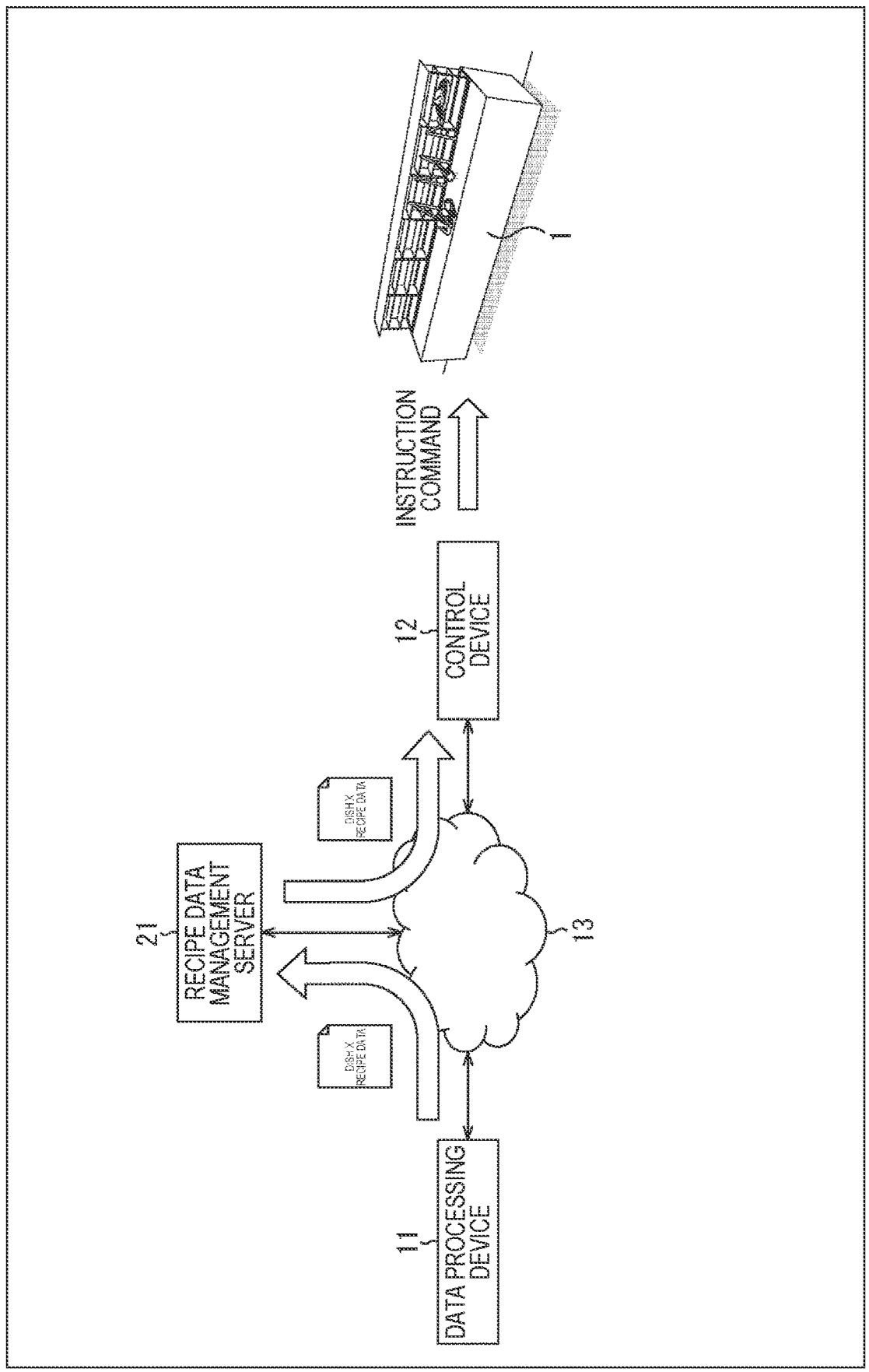
FIG. 25 is a diagram illustrating another configuration example of the cooking system.

FIG. 25 is a diagram illustrating another configuration example of the cooking system.

As illustrated in FIG. 25, the recipe data may be provided from the chef side to the reproduction side via a server on the network.

The recipe data management server 21 illustrated in FIG. 25 receives the recipe data transmitted from each data processing device 11 and manages the recipe data by causing a database to store the recipe data. The recipe data management server 21 transmits predetermined recipe data to the control device 12 in response to a request transmitted from the control device 12 via the network 13.

The recipe data management server 21 has a function to centrally manage the recipe data of dishes made by chefs of various restaurants and distribute the recipe data in response to a request from the reproduction side.

Figure 26:
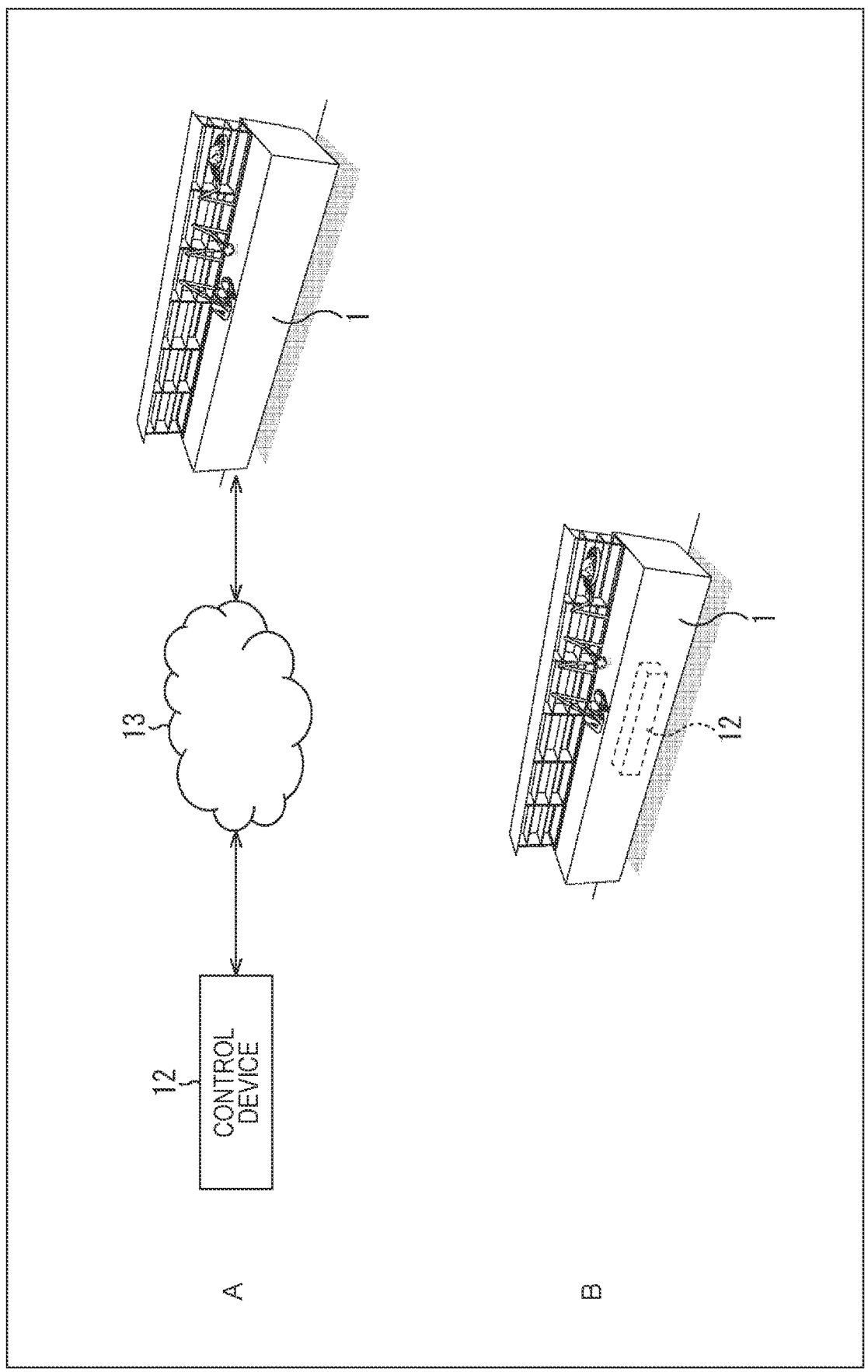
FIG. 26 is a diagram illustrating an arrangement example of a control device.

FIG. 26 is a diagram illustrating an arrangement example of the control device 12.

As illustrated in A in FIG. 26, the control device 12 is provided as, for example, a device outside the cooking robot 1. In the example of A in FIG. 26, the control device 12 and the cooking robot 1 are connected via the network 13.

The instruction command transmitted from the control device 12 is received by the cooking robot 1 via the network 13. An image captured by a camera of the cooking robot 1 and various data such as sensor data measured by the sensors provided in the cooking robot 1 are transmitted from the cooking robot 1 to the control device 12 via the network 13.

A plurality of cooking robots 1 may be connected to one control device 12, instead of one cooking robot 1 being connected to one control device 12.

As illustrated in B in FIG. 26, the control device 12 may be provided inside a housing of the cooking robot 1. In this case, the operation of each part of the cooking robot 1 is controlled in accordance with the instruction command generated by the control device 12.

Hereinafter, description will be given on the assumption that the control device 12 is provided as a device outside the cooking robot 1.

(2) Configuration on Chef Side

Figure 27:
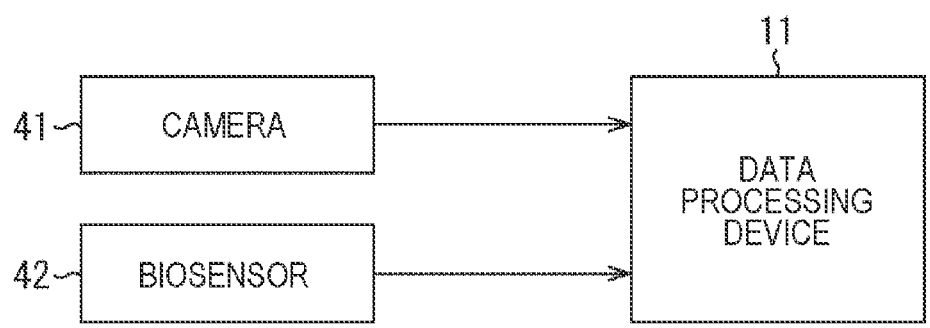
FIG. 27 is a block diagram illustrating a configuration example on the chef side.

FIG. 27 is a block diagram illustrating a configuration example on the chef side.

As illustrated in FIG. 27, the camera 41 and a biosensor 42 are connected to the data processing device 11. The same configuration as the above-described configuration is denoted by the same sign. Overlapping description will be omitted as appropriate.

The camera 41 captures the state of the chef cooking and the state on a top plate of the kitchen, and transmits images obtained by the capture to the data processing device 11.

The camera 41 includes a plurality of cameras. Some of the cameras configuring the camera 41 are, for example, attached to the chef's head. The camera attached to the chef's head captures the state of hands of the chef who is cooking, the state of the ingredients to be cooked, and the state on the top plate of the kitchen, and transmits an image obtained by the capture to the data processing device 11.

The biosensor 42 is a sensor that measures the biological reaction of the chef. The biosensor 42 includes an electro-encephalograph, a skin sensor, an electromyograph, an infra-red sensor, a motion sensor, a wearable activity meter, a microphone, and the like, which measure the above-described biological reactions. The image captured by the camera 41 is also appropriately used to measure the chef's biological reaction.

The biosensor 42 transmits data representing the measurement result of the chef's biological reaction to the data processing device 11.

Various sensors for recognizing the chef's operations, such as a gyro sensor attached to the chef's body and an infrared sensor for capturing the chef, are connected to the data processing device 11, in addition to the camera 41 and the biosensor 42.

Figure 28:
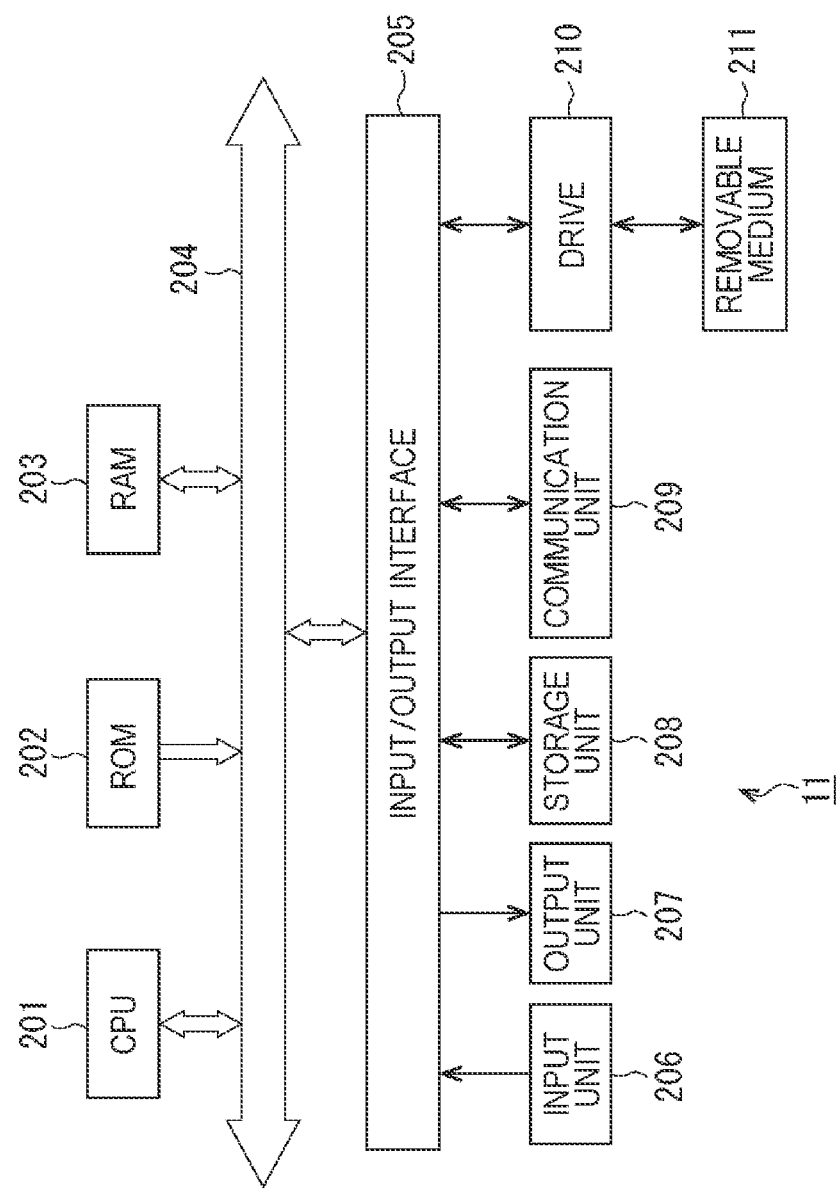
FIG. 28 is a block diagram illustrating a configuration example of hardware of a data processing device.

FIG. 28 is a block diagram illustrating a configuration example of hardware of the data processing device 11.

As illustrated in FIG. 28, the data processing device 11 is configured by a computer. A central processing unit (CPU) 201, a read only memory (ROM) 202, and a random access memory (RAM) 203 are mutually connected by a bus 204.

Moreover, an input/output interface 205 is connected to the bus 204. An input unit 206 including a keyboard, a mouse, and the like, and an output unit 207 including a display, a speaker, and the like are connected to the input/output interface 205.

Furthermore, a storage unit 208 including a hard disk, a nonvolatile memory, and the like, a communication unit 209 including a network interface and the like, and a drive 210 for driving a removable medium 211 are connected to the input/output interface 205.

In the computer configured as described above, the CPU 201 loads, for example, a program stored in the storage unit 208 into the RAM 203 via the input/output interface 205 and the bus 204 and executes the program, thereby performing series of processing.

Figure 29:
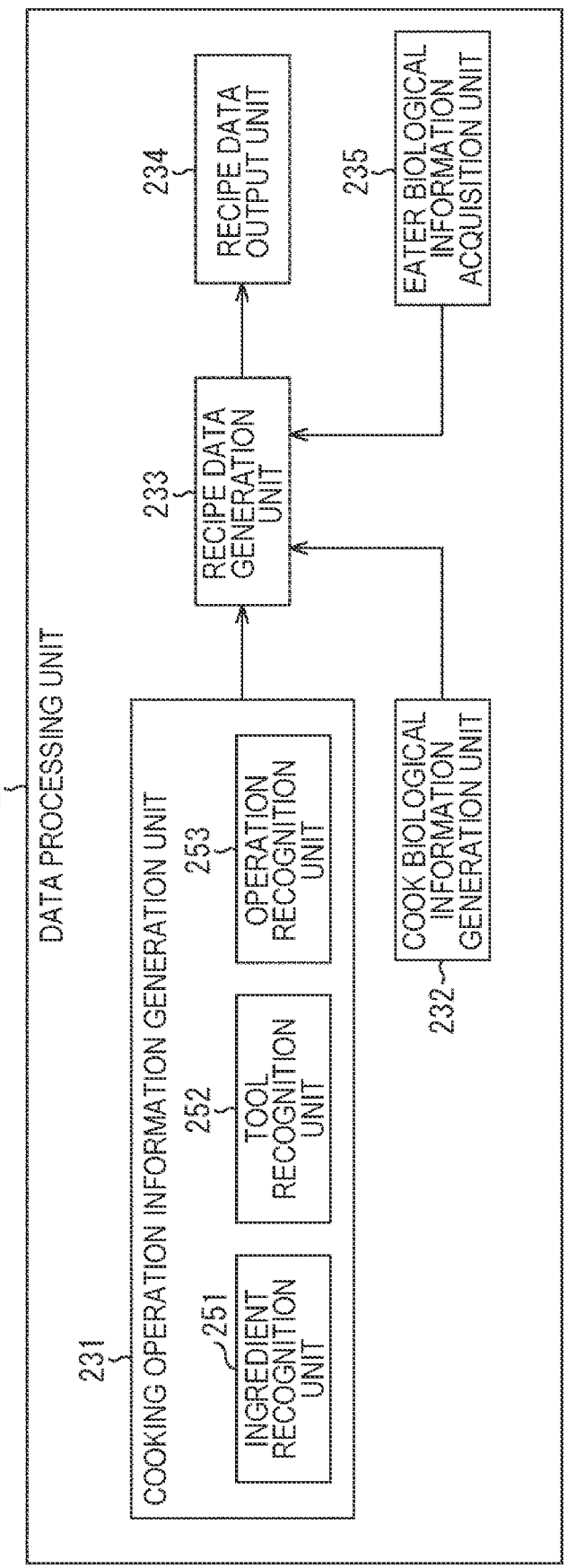
FIG. 29 is a block diagram illustrating a functional configuration example of the data processing device.

FIG. 29 is a block diagram illustrating a functional configuration example of the data processing device 11.

At least a part of functional units illustrated in FIG. 29 is implemented by the CPU 201 in FIG. 28 executing a predetermined program.

As illustrated in FIG. 29, a data processing unit 221 is implemented in the data processing device 11. The data processing unit 221 includes a cooking operation information generation unit 231, a cook biological information generation unit 232, a recipe data generation unit 233, a recipe data output unit 234, and an eater biological information acquisition unit 235.

The cooking operation information generation unit 231 includes an ingredient recognition unit 251, a tool recognition unit 252, and an operation recognition unit 253.

The ingredient recognition unit 251 analyzes the image captured by the camera 41 and recognizes the type of the ingredient used by the chef for cooking. The ingredient recognition unit 251 is provided with recognition information such as characteristic information for use in recognizing various types of ingredients.

The tool recognition unit 252 analyzes the image captured by the camera 41 and recognizes the type of the cooking tool used by the chef for cooking. The tool recognition unit 252 is provided with recognition information for use in recognizing various types of cooking tools.

The operation recognition unit 253 analyzes the image captured by the camera 41, the sensor data representing the measurement result of the sensor attached to the chef's body, and the like, and recognizes the operation of the chef who is cooking.

Information representing the recognition result by each unit of the cooking operation information generation unit 231 is supplied to the recipe data generation unit 233.

The cook biological information generation unit 232 measures the chef's biological reaction by controlling the biosensor 42. As described above, the biological reaction of the chef who is having a taste is measured. The cook biological information generation unit 232 acquires the sensor data representing the measurement result of the chef's biological reaction transmitted from the biosensor 42 and outputs the sensor data to the recipe data generation unit 233.

The recipe data generation unit 233 generates the cooking operation information on the basis of the information supplied from each unit of the cooking operation information generation unit 231. That is, the recipe data generation unit 233 generates ingredient information on the basis of the recognition result by the ingredient recognition unit 251 and generates the operation information on the basis of the recognition result by the tool recognition unit 252 and the operation recognition unit 253. The recipe data generation unit 233 generates the cooking operation information including the ingredient information and the operation information.

Furthermore, the recipe data generation unit 233 generates the cook biological information on the basis of the sensor data supplied from the cook biological information generation unit 232. The recipe data generation unit 233 appropriately identifies whether or not the chef judges that the ingredient is delicious on the basis of the flavor determination model or the like, and sets the flavor OK flag.

In a case where all pieces of cook biological information representing the biological reaction measured when the chef has had a taste are included in the recipe data, the flavor OK flag is set to the cook biological information representing the biological reaction in which the chef judges the ingredient is delicious among all the pieces of cook biological information.

In a case where not all pieces of cook biological information but only the cook biological information representing the biological reaction in which the chef judges that the ingredient is delicious is included in the recipe data, the flavor OK flag may be set to the cook biological information.

The recipe data generation unit 233 generates the cooking process data set by associating the cooking operation information and the cook biological information for each cooking process of the chef, for example. The recipe data generation unit 233 collects the cooking process data sets regarding the cooking processes from the first cooking process to the last cooking process of a certain dish, thereby to generate the recipe data describing the plurality of cooking process data sets.

The recipe data generation unit 233 outputs the recipe data generated in this way to the recipe data output unit 234.

In addition, the recipe data generation unit 233 updates the cooking process on the basis of the eater biological information to customize the recipe data in a case where the eater biological information representing the eater's biological reaction is supplied from the eater biological information acquisition unit 235. The eater biological information supplied from the eater biological information acquisition unit 235 includes information indicating which recipe data is used on the reproduction side.

The recipe data generation unit 233 outputs the customized recipe data to the recipe data output unit 234.

The recipe data output unit 234 controls the communication unit 209 (FIG. 28) and outputs the recipe data generated by the recipe data generation unit 233. The recipe data output from the recipe data output unit 234 is supplied to the control device 12 or the recipe data management server 21 via the network 13.

(3) Configuration on Reproduction Side
(3-1) Configuration of Cooking Robot 1
Appearance of Cooking Robot 1

Figure 30:
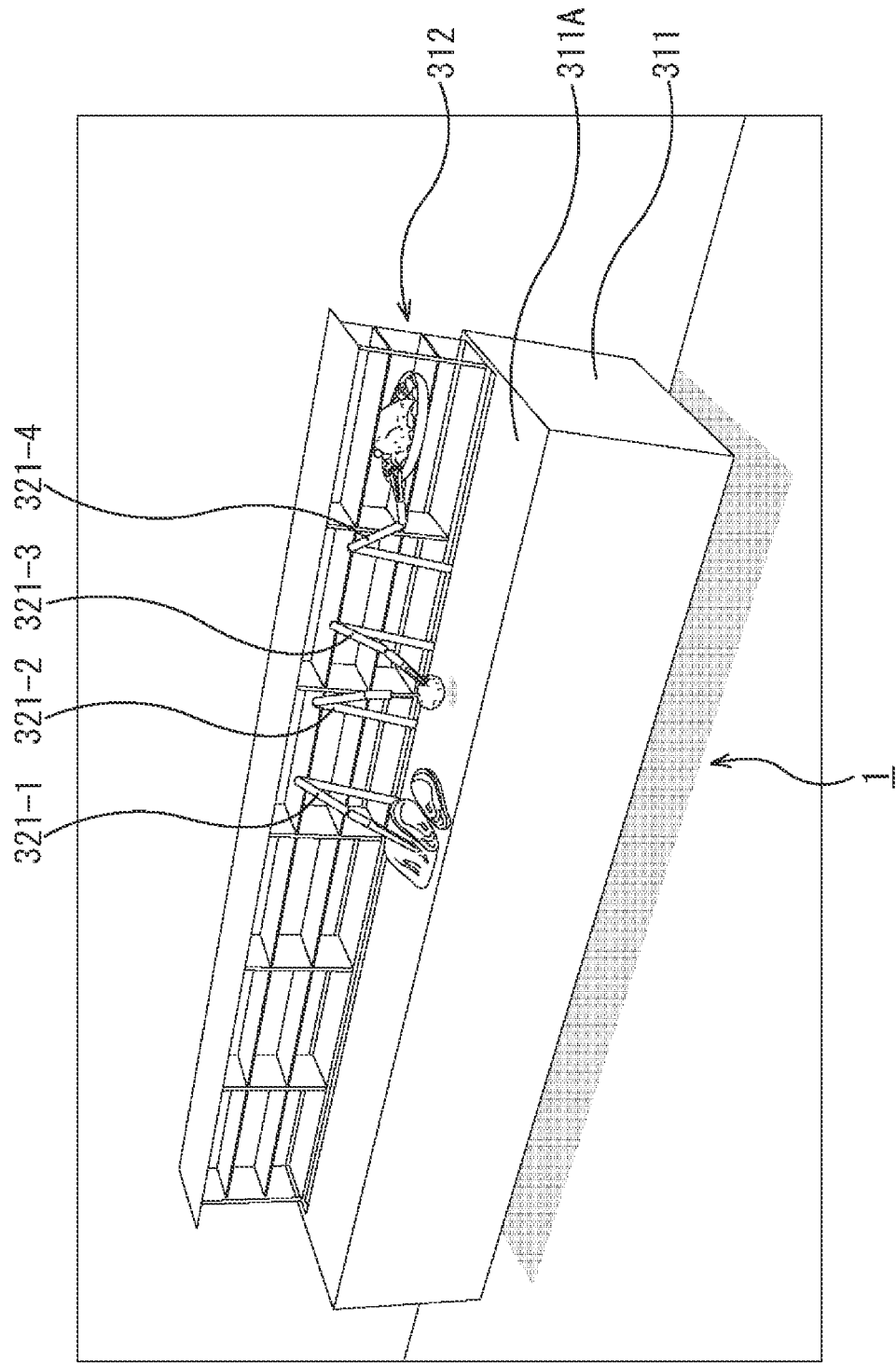
FIG. 30 is a perspective view illustrating an appearance of a cooking robot.

FIG. 30 is a perspective view illustrating an appearance of the cooking robot 1.

As illustrated in FIG. 30, the cooking robot 1 is a kitchen-type robot having an oblong rectangular parallelepiped housing 311. Various configurations are provided inside the housing 311 that is a main body of the cooking robot 1.

A cooking assistance system 312 is provided on a back side of the housing 311 so as to stand from an upper surface of the housing 311. Spaces formed in the cooking assistance system 312 by being divided by thin plate-like members have functions for assisting the cooking by cooking arms 321-1 to 321-4, such as a refrigerator, an oven range, and storage.

A rail is provided on a top plate 311A in a longitudinal direction, and the cooking arms 321-1 to 321-4 are provided on the rail. The cooking arms 321-1 to 321-4 can be changed in position along the rail as a moving mechanism.

The cooking arms 321-1 to 321-4 are robot arms configured by connecting cylindrical members with joint portions. Various operations related to cooking are performed by the cooking arms 321-1 to 321-4.

A space above the top plate 311A is a cooking space where the cooking arms 321-1 to 321-4 cook.

Although the four cooking arms are illustrated in FIG. 30, the number of cooking arms is not limited to four. Hereinafter, the cooking arms 321-1 to 321-4 will be collectively referred to as cooking arms 321 in a case where there is no need to distinguish the cooking arms 321-1 to 321-4.

Figure 31:
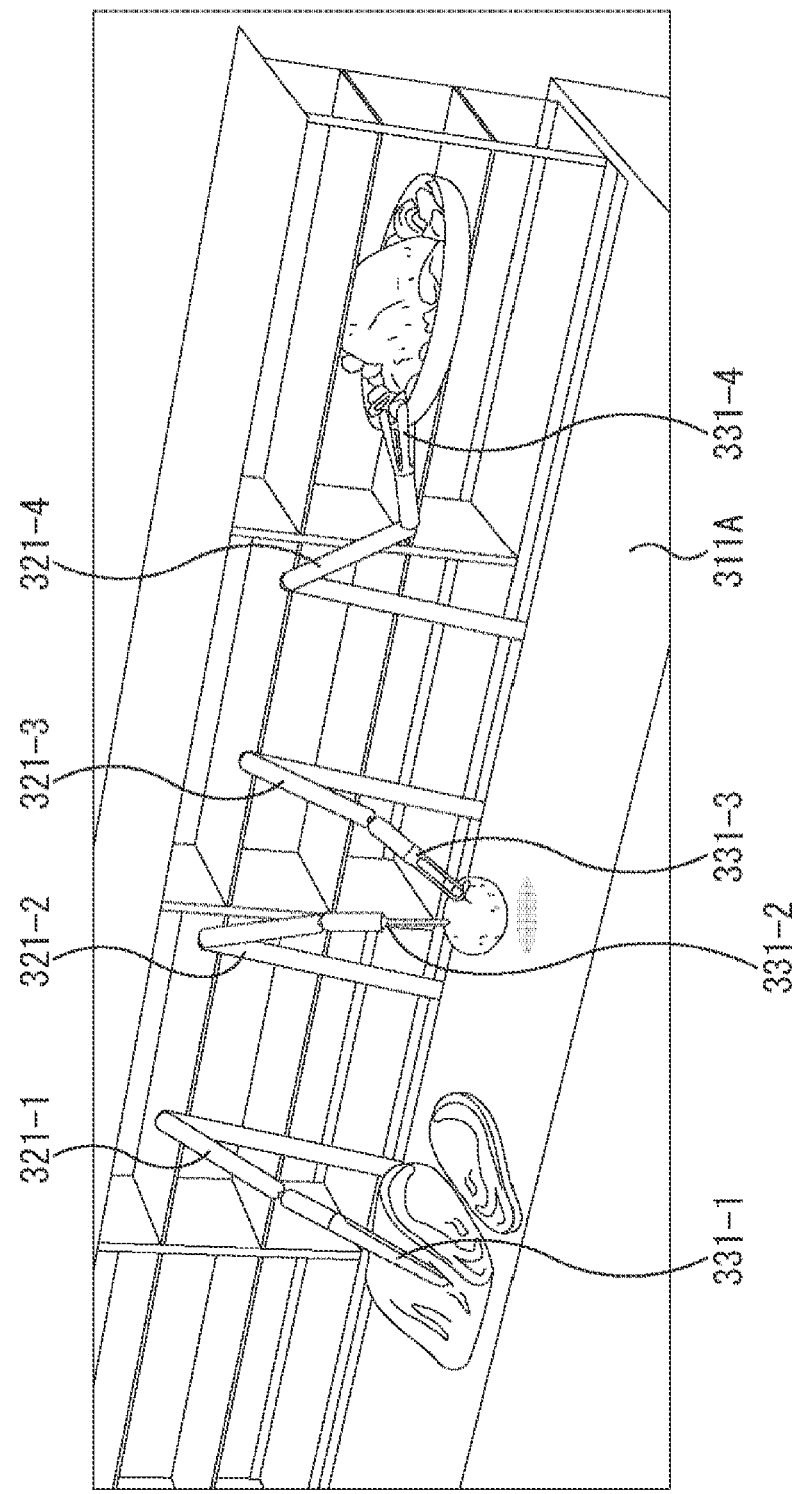
FIG. 31 is an enlarged view illustrating a situation of cooking arms.

FIG. 31 is a view illustrating an enlarged situation of cooking arms 321.

As illustrated in FIG. 31, attachments having various cooking functions are attached to distal ends of the cooking arms 321. As the attachments for the cooking arms 321, various attachments such as an attachment having a manipulator function (hand function) for gripping an ingredient, tableware, or the like, and an attachment having a knife function for cutting an ingredient are prepared.

In the example in FIG. 31, a knife attachment 331-1 that is an attachment having the knife function is attached to the cooking arm 321-1. A lump of meat placed on the top plate 311A is cut using the knife attachment 331-1.

A spindle attachment 331-2, which is an attachment used to fix an ingredient or rotate an ingredient, is attached to the cooking arm 321-2.

A peeler attachment 331-3, which is an attachment having a peeler function to peel off an ingredient, is attached to the cooking arm 321-3.

A potato lifted by the cooking arm 321-2 using the spindle attachment 331-2 is peeled off by the cooking arm 321-3 using the peeler attachment 331-3. As described above, the plurality of cooking arms 321 can perform one work in cooperation with one another.

A manipulator attachment 331-4, which is an attachment having a manipulator function, is attached to the cooking arm 321-4. A frying pan with chicken is carried using the manipulator attachment 331-4 to the space of the cooking assistance system 312 having an oven function.

Cooking by such cooking arms 321 proceeds by appropriately replacing the attachments according to the content of the work. The replacement of the attachment is automatically performed by the cooking robot 1, for example.

It is also possible to attach the same attachment to a plurality of cooking arms 321, such as attaching the manipulator attachment 331-4 to each of the four cooking arms 321.

The cooking by the cooking robot 1 is not only performed using the above attachments prepared as tools for the cooking arms but also appropriately performed using the same tool as a tool used by a person for cooking. For example, a knife used by a person is gripped by the manipulator attachment 331-4, and cooking such as cutting of an ingredient is performed using the knife.

Configuration of Cooking Arm

Figure 32:
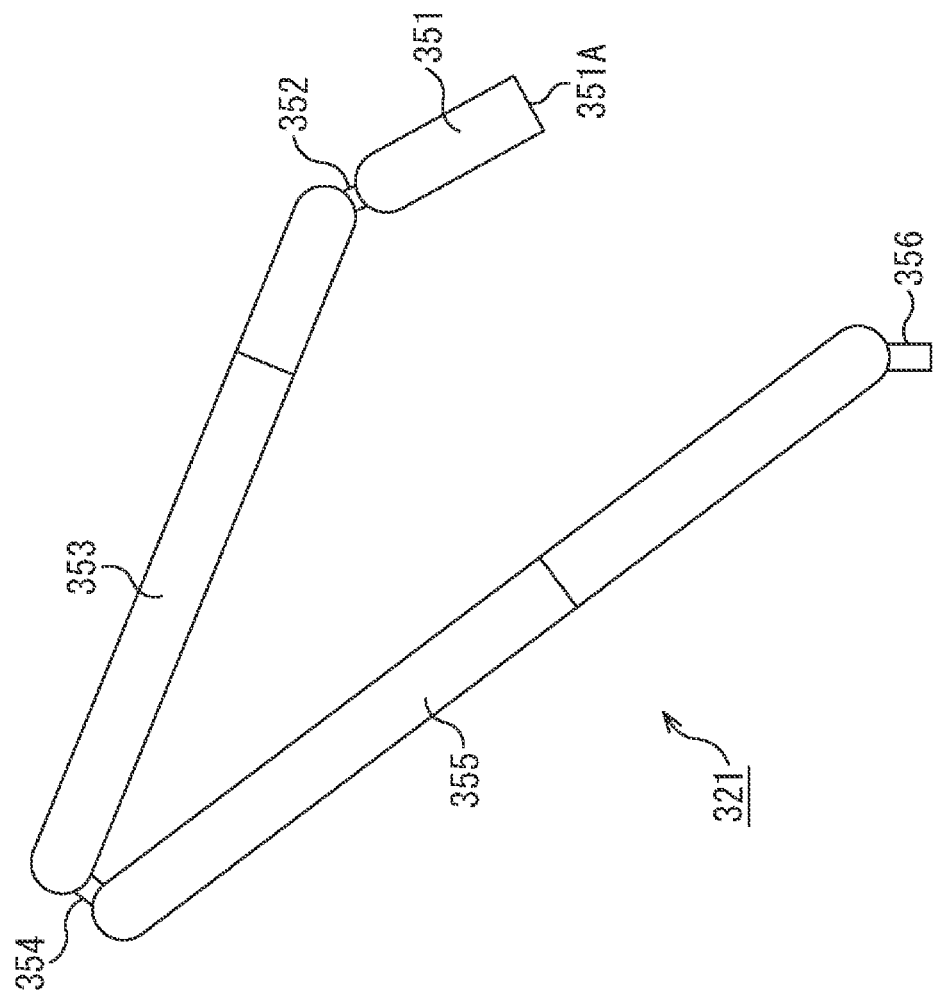
FIG. 32 is a view illustrating an appearance of the cooking arm.

FIG. 32 is a view illustrating an appearance of the cooking arm 321.

As illustrated in FIG. 32, the cooking arm 321 is generally configured by connecting thin cylindrical members with hinge portions serving as the joint portions. Each hinge portion is provided with a motor or the like that generates a force for driving each member.

As the cylindrical members, an attachment/detachment member 351, a relay member 353, and a base member 355 are provided in order from the distal end. The attachment/detachment member 351 is a member having a length of about ⅕ of the length of the relay member 353. The combined length of the length of the attachment/detachment member 351 and the length of the relay member 353 is substantially the same as the length of the base member 355.

The attachment/detachment member 351 and the relay member 353 are connected with a hinge portion 352, and the relay member 353 and the base member 355 are connected with a hinge portion 354. The hinge portion 352 and the hinge portion 354 are provided at both ends of the relay member 353.

In this example, the cooking arm 321 is configured by the three cylindrical members. However, the cooking arm 321 may be configured by four or more cylindrical members. In this case, a plurality of the relay members 353 is provided.

An attachment/detachment portion 351A where an attachment is attached or detached is provided at a distal end of the attachment/detachment member 351. The attachment/detachment member 351 includes the attachment/detachment portion 351A where various attachments are attached or detached, and functions as a cooking function arm unit that cooks by operating the attachment.

An attachment/detachment portion 356 to be mounted to the rail is provided at a rear end of the base member 355. The base member 355 functions as a moving function arm unit that implements movement of the cooking arm 321.

Figure 33:
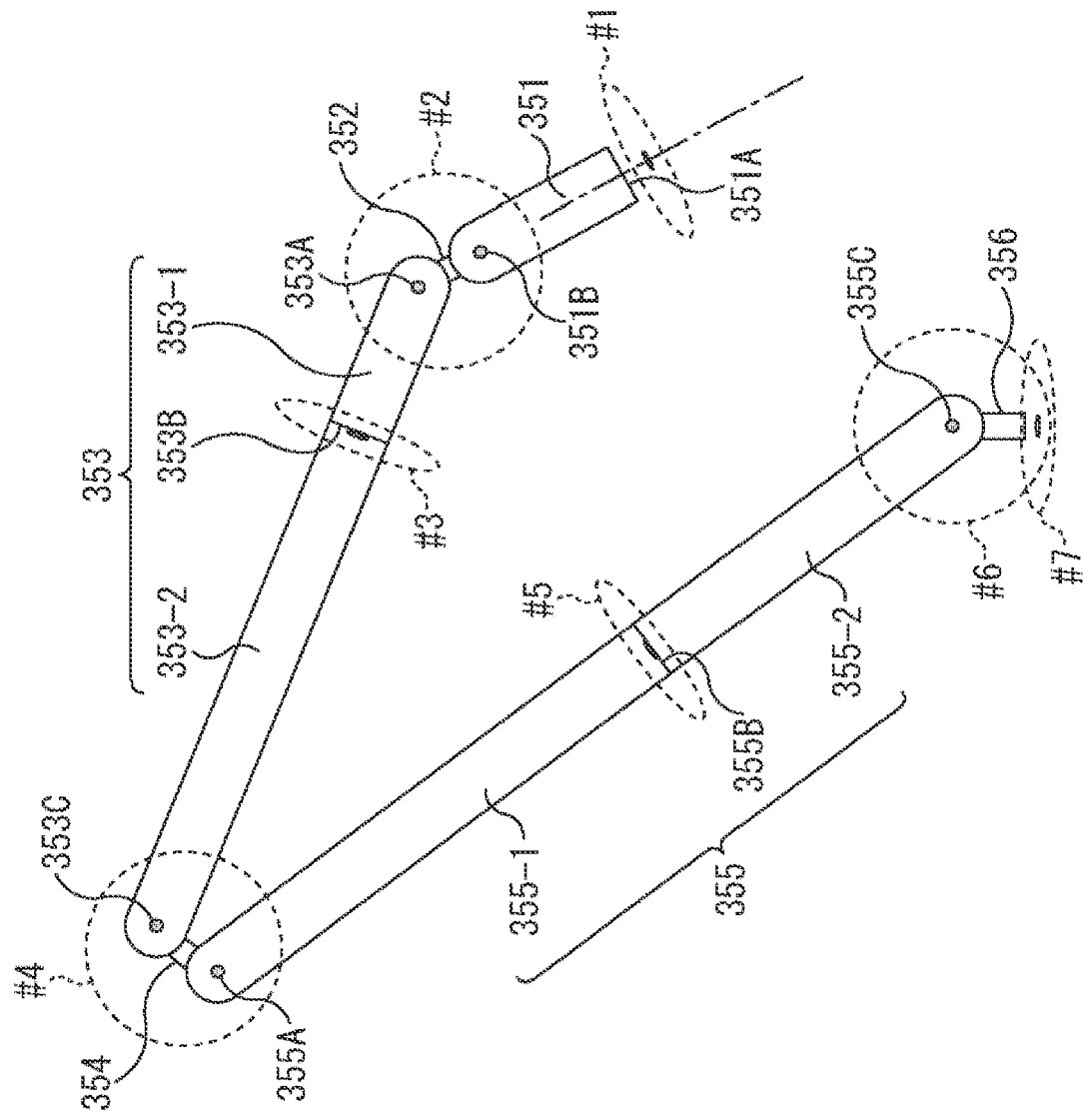
FIG. 33 is a view illustrating an example of movable ranges of respective parts of the cooking arm.

FIG. 33 is a view illustrating an example of movable ranges of respective parts of the cooking arm 321.

As illustrated by an ellipse #1, the attachment/detachment member 351 is rotatable about a central axis of a circular cross section. A flat small circle illustrated in the center of the ellipse #1 represents a direction of a rotation axis of an alternate long and short dash line.

As illustrated by a circle #2, the attachment/detachment member 351 is rotatable about an axis passing through a fitting portion 351B with the hinge portion 352. Furthermore, the relay member 353 is rotatable about an axis passing through a fitting portion 353A with the hinge portion 352.

Two small circles illustrated inside the circle #2 represent directions of respective rotation axes (in a direction perpendicular to the sheet surface). A movable range of the attachment/detachment member 351 centered on the axis passing through the fitting portion 351B and a movable range of the relay member 353 centered on the axis passing through the fitting portion 353A are, for example, a range of 90 degrees.

The relay member 353 is configured to be separated by a member 353-1 on a distal end side and a member 353-2 on a rear end side. As illustrated by an ellipse #3, the relay member 353 is rotatable about a central axis of a circular cross section at a connecting portion 353B between the member 353-1 and the member 353-2.

Other movable portions basically have a similar movable range.

In other words, as illustrated by a circle #4, the relay member 353 is rotatable about an axis passing through a fitting portion 353C with the hinge portion 354. Furthermore, the base member 355 is rotatable about an axis passing through a fitting portion 355A with the hinge portion 354.

The base member 355 is configured to be separated by a member 355-1 on a distal end side and a member 355-2 on a rear end side. As illustrated by an ellipse #5, the base member 355 is rotatable about a central axis of a circular cross section at a connecting portion 355B between the member 355-1 and the member 355-2.

As illustrated by a circle #6, the base member 355 is rotatable about an axis passing through a fitting portion 355C with the attachment/detachment portion 356.

As illustrated by an ellipse #7, the attachment/detachment portion 356 is mounted to the rail to become rotatable about a central axis of a circular cross section.

Thus, the attachment/detachment member 351 having the attachment/detachment portion 351A at the distal end, the relay member 353 connecting the attachment/detachment member 351 and the base member 355, and the base member 355, to the rear end of which the attachment/detachment portion 356 is connected, are respectively connected to be rotatable with the hinge portions. The movement of each movable portion is controlled by a controller in the cooking robot 1 according to the instruction command.

Figure 34:
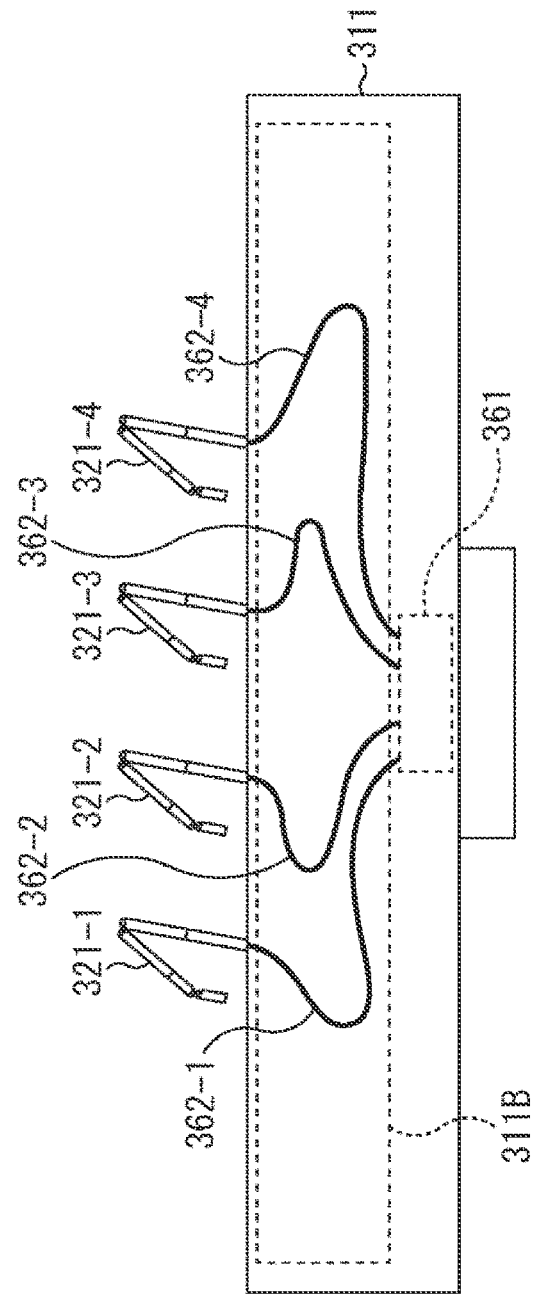
FIG. 34 is a view illustrating an example of connection between the cooking arms and a controller.

FIG. 34 is a view illustrating an example of connection between the cooking arms and the controller.

As illustrated in FIG. 34, the cooking arms 321 and a controller 361 are connected via a wire in a space 311B formed inside the housing 311. In the example in FIG. 34, the cooking arms 321-1 to 321-4 and the controller 361 are respectively connected via wires 362-1 to 362-4. The wires 362-1 to 362-4 having flexibility are appropriately bent depending on the positions of the cooking arms 321-1 to 321-4.

As described above, the cooking robot 1 is a robot capable of performing various works related to cooking by driving the cooking arms 321.

Configuration Around Cooking Robot 1

Figure 35:
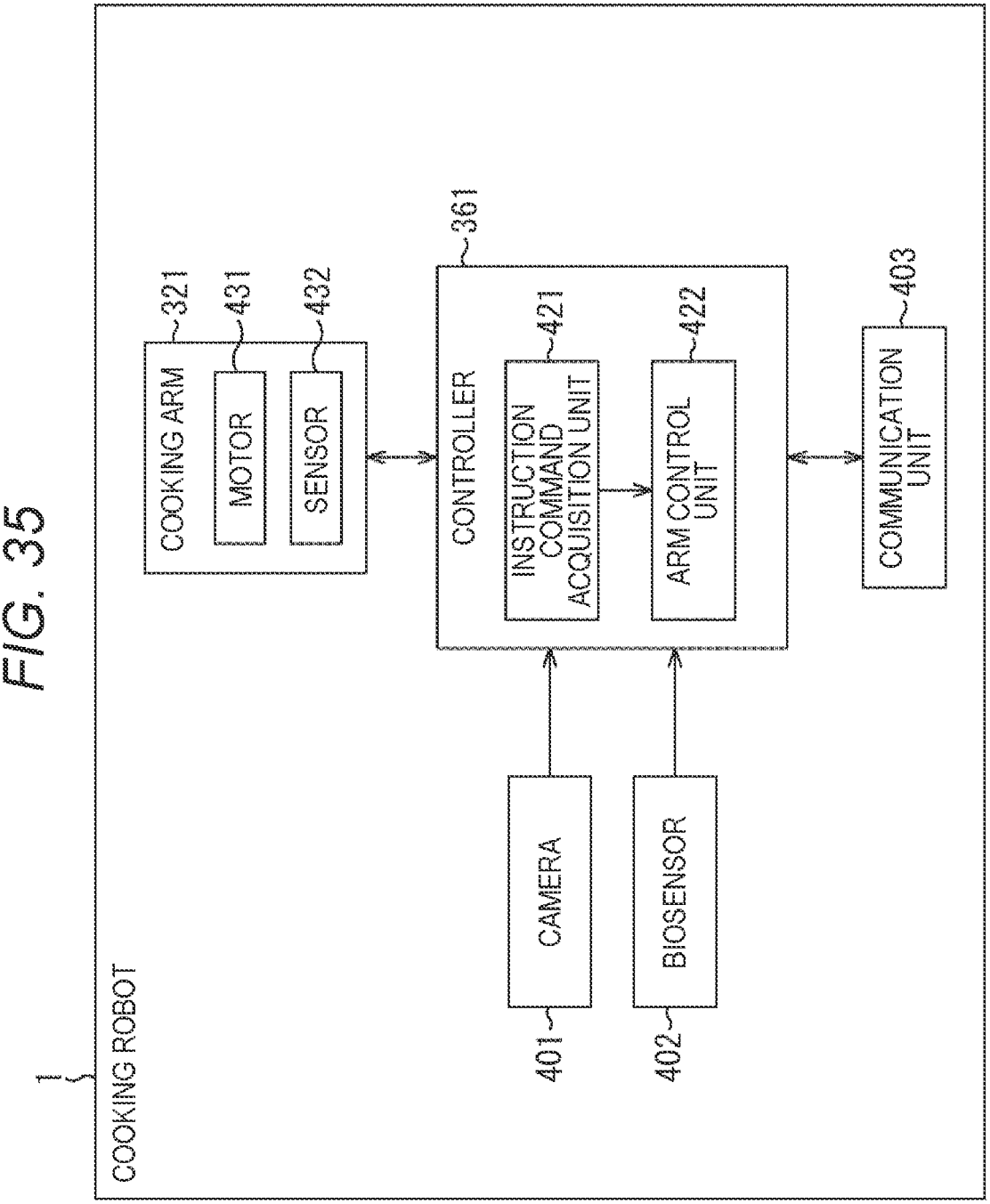
FIG. 35 is a block diagram illustrating an example of a configuration of the cooking robot and its surroundings.

FIG. 35 is a block diagram illustrating an example of a configuration of the cooking robot 1 and its surroundings.

The cooking robot 1 is configured by connecting each part to the controller 361. The same configuration, of the configuration illustrated in FIG. 35, as the above-described configuration is denoted by the same sign. Overlapping description will be omitted as appropriate.

A camera 401, a biosensor 402, and a communication unit 403 are connected, in addition to the cooking arms 321, to the controller 361.

Although not illustrated in FIG. 30 and the like, the sensors same as the sensors provided on the chef side are provided at predetermined positions of the cooking robot 1 itself or around the cooking robot 1. The camera 401 and the biosensor 402 have similar functions to the camera 41 and the biosensor 42 on the chef side, respectively.

The controller 361 is configured by a computer having a CPU, a ROM, a RAM, a flash memory, and the like. The controller 361 functions as a control unit that executes a predetermined program by the CPU to control an overall operation of the cooking robot 1.

In the controller 361, a predetermined program is executed to implement an instruction command acquisition unit 421 and an arm control unit 422.

The instruction command acquisition unit 421 acquires an instruction command transmitted from the control device 12 and received by the communication unit 403. The instruction command acquired by the instruction command acquisition unit 421 is supplied to the arm control unit 422.

The arm control unit 422 controls the operation of the cooking arms 321 in accordance with the instruction command acquired by the instruction command acquisition unit 421.

The camera 401 captures a state of the cooking arm 321 performing the cooking operation, a state of the ingredients to be cooked, and a state on the top plate 311A of the cooking robot 1, and outputs the images obtained by the capture to the controller 361. The camera 401 is provided at various positions such as a front of the cooking assistance system 312 and a distal end of the cooking arm 321.

In addition, the camera 401 captures the state of the eater tasting the food and the state of the eater eating the dish, and outputs an image obtained by the capture to the controller 361.

The biosensor 402 is a sensor that measures the biological reaction of the eater. The biological sensor 402 includes an electroencephalograph, a skin sensor, an electromyograph, an infrared sensor, a motion sensor, a wearable activity meter, a microphone, and the like, which measure the above-described biological reactions.

The biosensor 42 transmits data representing the measurement result of the eater's biological reaction to the controller 361.

The communication unit 403 is a wireless communication module such as a wireless LAN module or a portable communication module compatible with long term evolution (LTE). The communication unit 403 communicates with the control device 12 or an external device such as a recipe data management server 21 on the Internet.

Furthermore, the communication unit 403 communicates with a portable terminal such as a smartphone or a tablet terminal used by the user. The user is a person who eats the food reproduced by the cooking robot 1. A user's operation on the cooking robot 1 such as selection of a dish may be input by an operation on the portable terminal.

As illustrated in FIG. 35, the cooking arm 321 is provided with a motor 431 and a sensor 432.

The motor 431 is provided at each joint portion of the cooking arm 321. The motor 431 performs a rotation operation around the axis under the control of the arm control unit 422. An encoder for measuring the amount of rotation of the motor 431, a driver for adaptively controlling the rotation of the motor 431 on the basis of the measurement result by the encoder, and the like are also provided at each joint portion.

The sensor 432 is configured by, for example, a gyro sensor, an acceleration sensor, a touch sensor, or the like. The sensor 432 measures angular velocity, acceleration, and the like of each joint portion during the operation of the cooking arm 321 and outputs information indicating the measurement result to the controller 361. The sensor data indicating the measurement result of the sensor 432 is also transmitted from the cooking robot 1 to the control device 12 as appropriate.

Information regarding the specification of the cooking robot 1 such as the number of cooking arms 321 is provided from the cooking robot 1 to the control device 12 at predetermined timing. In the control device 12, the operation is planned according to specifications of the cooking robot 1. The instruction commands generated in the control device 12 correspond to the specifications of the cooking robot 1.

(3-2) Configuration of Control Device 12

The control device 12 that controls the operation of the cooking robot 1 is configured by a computer as illustrated in FIG. 28, similarly to the data processing device 11. Hereinafter, description will be given citing the configuration of the data processing device 11 illustrated in FIG. 28 as the configuration of the control device 12 as appropriate.

Figure 36:
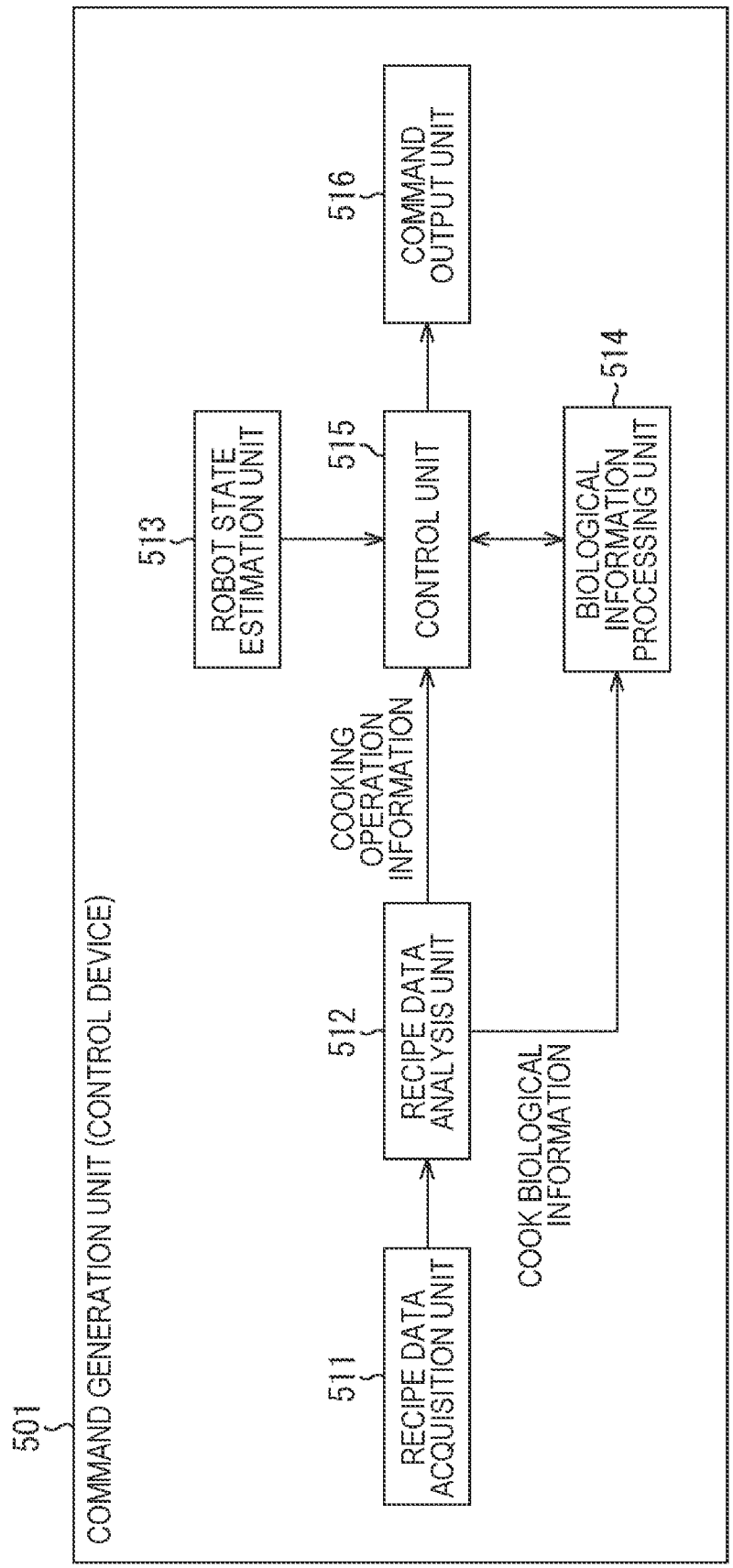
FIG. 36 is a block diagram illustrating a functional configuration example of the control device.

FIG. 36 is a block diagram illustrating a functional configuration example of the control device 12.

At least a part of functional units illustrated in FIG. 36 is implemented by the CPU 201 (FIG. 28) of the control device 12 executing a predetermined program.

As illustrated in FIG. 36, in the control device 12, a command generation unit 501 is implemented. The command generation unit 501 includes a recipe data acquisition unit 511, a recipe data analysis unit 512, a robot state estimation unit 513, a biological information processing unit 514, a control unit 515, and a command output unit 516.

The recipe data acquisition unit 511 controls the communication unit 209 and acquires the recipe data by receiving the recipe data transmitted from the data processing device 11 or by communicating with the recipe data management server 21. The recipe data acquired by the recipe data acquisition unit 511 is, for example, recipe data of a dish selected by the eater.

Similarly, in a case where the customized recipe data is transmitted from the data processing device 11, the customized recipe data is acquired by the recipe data acquisition unit 511.

A database of the recipe data may be provided in the storage unit 208. In this case, the recipe data is acquired from the database provided in the storage unit 208. The recipe data acquired by the recipe data acquisition unit 511 is supplied to the recipe data analysis unit 512.

The recipe data analysis unit 512 analyzes the recipe data acquired by the recipe data acquisition unit 511. In a case where it is time to perform a certain cooking process, the recipe data analysis unit 512 analyzes the cooking process data set related to the cooking process and extracts the cooking operation information and the adjuster biological information. The cooking operation information extracted from the cooking process data set is supplied to the control unit 515, and the adjuster biological information is supplied to the biological information processing unit 514.

The robot state estimation unit 513 controls the communication unit 209 to receive the image and the sensor data transmitted from the cooking robot 1. From the cooking robot 1, the image captured by the camera of the cooking robot 1 and the sensor data measured by a sensor provided at a predetermined position of the cooking robot 1 are transmitted at a predetermined cycle. A situation around the cooking robot 1 is captured in the image captured by the camera of the cooking robot 1.

The robot state estimation unit 513 estimates the state around the cooking robot 1 such as the state of the cooking arms 321 and the state of the ingredients by analyzing the image and the sensor data transmitted from the cooking robot 1. Information indicating the state around the cooking robot 1 estimated by the robot state estimation unit 513 is supplied to the control unit 515.

The biological information processing unit 514 controls, in cooperation with the control unit 515, the operation of the cooking robot 1 on the basis of the cook biological information supplied from the recipe data analysis unit 512.

For example, in a case where there is the cook biological information to which the flavor OK flag is set, the biological information processing unit 514 requests the eater to have a taste at corresponding timing of the chef's tasting timing. As described above, in the case where the chef has tasted the ingredient after performing certain cooking, and the biological reaction of the chef at the tasting determines that the ingredient is delicious, the eater is required to have a taste at timing after the same cooking has been performed by the cooking robot 1.

In a case where the sensor data representing the biological reaction of when the eater is having a taste is transmitted from the cooking robot 1 and received by the communication unit 209, the biological information processing unit 514 acquires the sensor data. The biological information processing unit 514 generates the eater biological information on the basis of the acquired sensor data and transmits the eater biological information to the data processing device 11.

The control unit 515 controls the operation of the cooking robot 1 by generating an instruction command and transmitting the instruction command from the command output unit 516. The operation of the cooking robot 1 is controlled by the control unit 515 on the basis of the cooking operation information supplied from the recipe data analysis unit 512.

For example, the control unit 515 identifies the ingredients to be used in the cooking process to be executed on the basis of the ingredient information included in the cooking operation information. Furthermore, the control unit 515 identifies the cooking tool used in the cooking process and the operation to be executed by the cooking arms 321 on the basis of the operation information included in the cooking operation information.

The control unit 515 sets a state where preparation of the ingredients is ready as a goal state, and sets an operation sequence from the current state, which is the current state of the cooking robot 1, to the goal state. The control unit 515 generates an instruction command for performing each operation configuring the operation sequence, and outputs the instruction command to the command output unit 516.

In the cooking robot 1, the cooking arms 321 are controlled according to the instruction command generated by the control unit 515, and the ingredients are prepared. Information representing the state of the cooking robot 1 at each timing, including the state of the cooking arms 321 is transmitted from the cooking robot 1 to the control device 12.

Furthermore, in a case where the ingredients are ready, the control unit 515 sets a state in which cooking using the prepared ingredients (cooking in one cooking process to be executed) is completed as the goal state, and sets the operation sequence from the current state to the goal state. The control unit 515 generates an instruction command for performing each operation configuring the operation sequence, and outputs the instruction command to the command output unit 516.

In the cooking robot 1, the cooking arms 321 are controlled according to the instruction command generated by the control unit 515, and cooking using the ingredients is performed.

The operation of the cooking robot 1 is controlled by the control unit 515 by using, for example, the above instruction commands. The control unit 515 has a function as a generation unit for generating the instruction commands.

Note that the instruction command generated by the control unit 515 may be a command for giving an instruction of execution of an entire action for causing a certain state transition or may be a command for giving an instruction of execution of a part of an action. In other words, one action may be executed according to one instruction command or may be executed according to a plurality of instruction commands.

The command output unit 516 controls the communication unit 209 and transmits the instruction command generated by the control unit 515 to the cooking robot 1.

<Operation of Cooking System>

Here, the operations of the cooking system having the above configuration will be described. In the recipe data, the cook biological information representing the biological reaction of the chef is associated for each cooking process.

(1) Operation on Chef Side

First, recipe data generation processing of the data processing device 11 will be described with reference to the flowchart of FIG. 37.

Figure 37:
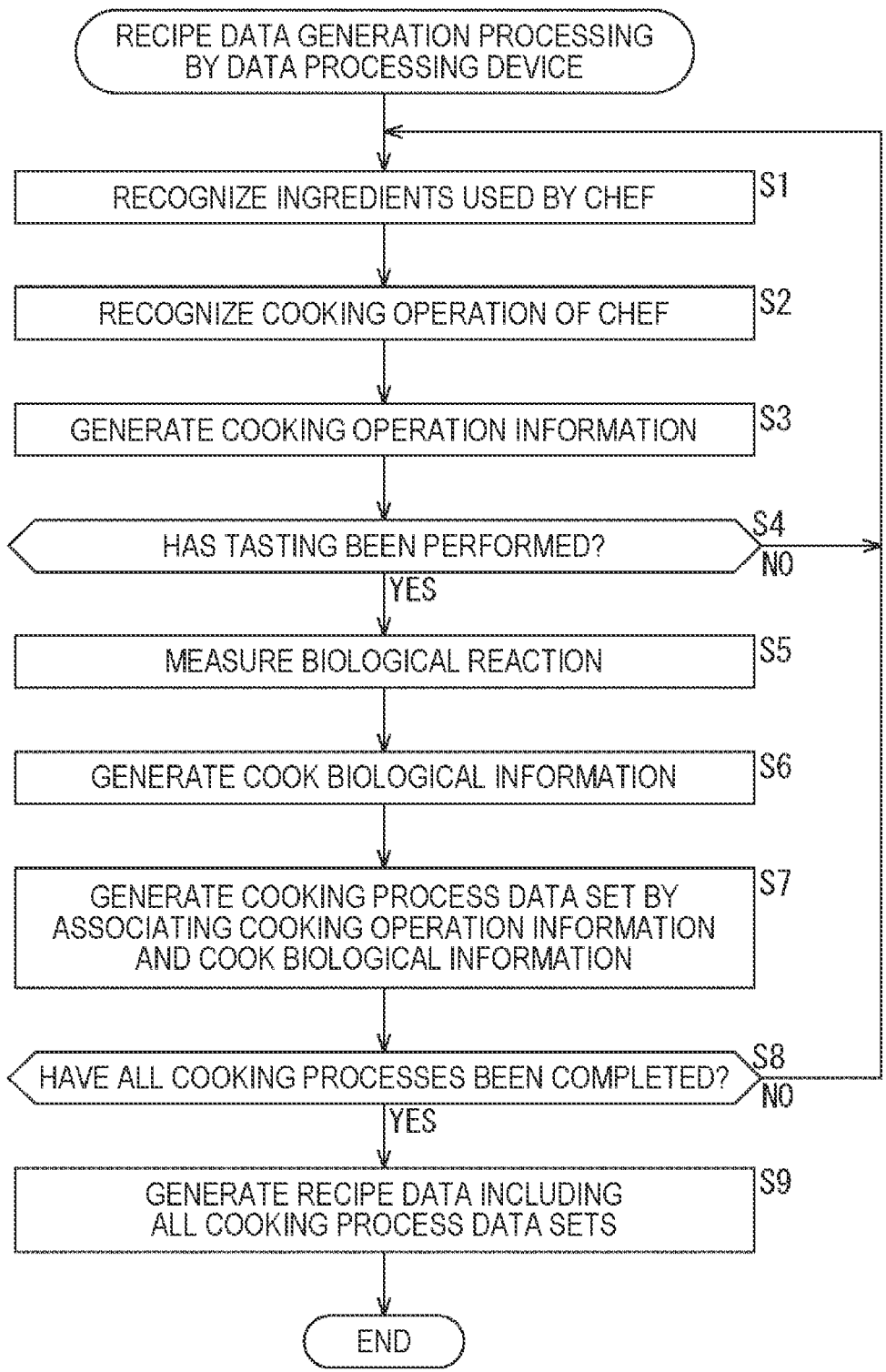
FIG. 37 is a flowchart for describing recipe data generation processing of the data processing device.

The processing in FIG. 37 is started when the ingredients and cooking tools are ready and the chef starts cooking. Capture by the camera 41, sensing by the sensors attached to the chef's body, and the like are also started.

In step S1, the ingredient recognition unit 251 of FIG. 29 analyzes the image captured by the camera 41 and recognizes the ingredients to be used by the chef.

In step S2, the operation recognition unit 253 analyzes the image captured by the camera 41, the sensor data representing the measurement result of the sensor attached to the chef's body, and the like, and recognizes the cooking operation of the chef.

In step S3, the recipe data generation unit 233 generates the cooking operation information on the basis of the ingredient information generated on the basis of the recognition result by the ingredient recognition unit 251 and the operation information generated on the basis of the recognition result by the operation recognition unit 253.

In step S4, the recipe data generation unit 233 determines whether or not tasting has been performed, and returns to step S1 and repeats the above-described processing in a case where it is determined that tasting has not been performed.

In a case where it is determined in step S4 that tasting has been completed, the processing proceeds to step S5.

In step S5, the cook biological information generation unit 232 measures the chef's biological reaction by controlling the biosensor 42. The sensor data representing the measurement result of the chef's biological reaction is acquired by the cook biological information generation unit 232 and supplied to the recipe data generation unit 233.

In step S6, the recipe data generation unit 233 generates the cook biological information on the basis of the sensor data supplied from the cook biological information generation unit 232.

In step S7, the recipe data generation unit 233 generates the cooking process data set by associating the cooking operation information with the cook biological information.

In step S8, the recipe data generation unit 233 determines whether or not all the cooking processes have been completed, and in a case where it is determined that all the cooking processes have not been completed, the processing returns to step S1 and the above-described processing is repeated. Similar processing is repeated for the next cooking process.

In a case where it is determined in step S8 that all the cooking processes have been completed, the processing proceeds to step S9.

In step S9, the recipe data generation unit 233 generates the recipe data including all the cooking process data sets.

Next, processing of customizing the recipe data by the data processing device 11 will be described with reference to the flowchart of FIG. 38.

Figure 38:
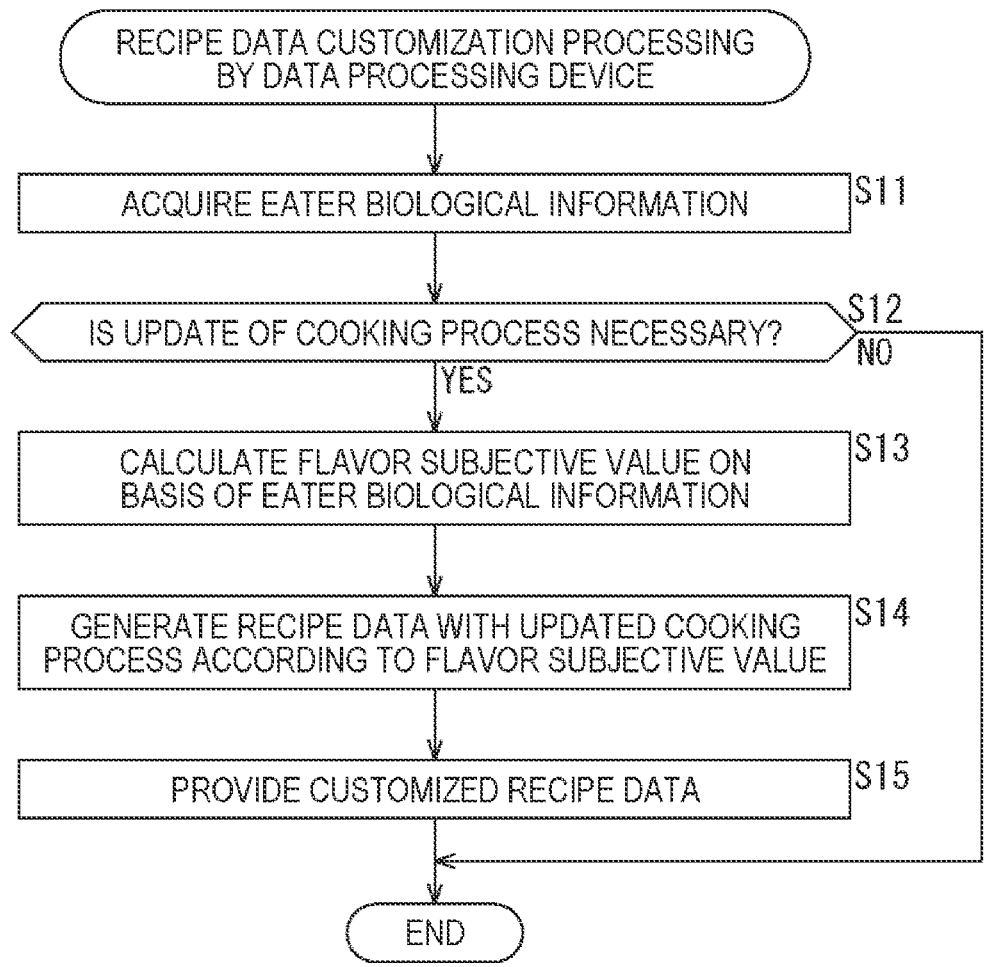
FIG. 38 is a flowchart illustrating recipe data customization processing of the data processing device.

The processing of FIG. 38 is started when the cooking process proceeds on the reproduction side and the tasting is performed at predetermined timing, so that the eater biological information is transmitted from the control device 12.

In step S11, the eater biological information acquisition unit 235 acquires the eater biological information transmitted from the control device 12.

In step S12, the eater biological information acquisition unit 235 determines whether or not the cooking process needs to be updated on the basis of the eater biological information.

Since the cook has determined that the cooked ingredient is delicious, the processing is terminated in a case where it is determined in step S12 that update of the cooking process is not necessary. In this case, the recipe data is not customized.

Meanwhile, since the cook has determined that the cooked ingredient is not delicious, the processing proceeds to step S13 in a case where it is determined in step S12 that update of the cooking process is necessary.

In step S13, the recipe data generation unit 233 inputs the eater biological information acquired by the eater biological information acquisition unit 235 into the flavor subjective information generation model, and calculates a flavor subjective value.

In step S14, the recipe data generation unit 233 generates the recipe data in which the cooking process has been updated according to how the eater feels the flavor represented by the flavor subjective value.

In step S15, the recipe data generation unit 233 outputs the customized recipe data to the recipe data output unit 234 by updating the cooking process, and provides the recipe data to the control device 12. In the control device 12, cooking is performed on the basis of the customized recipe data.

(2) Operation on Reproduction Side

Figure 39:
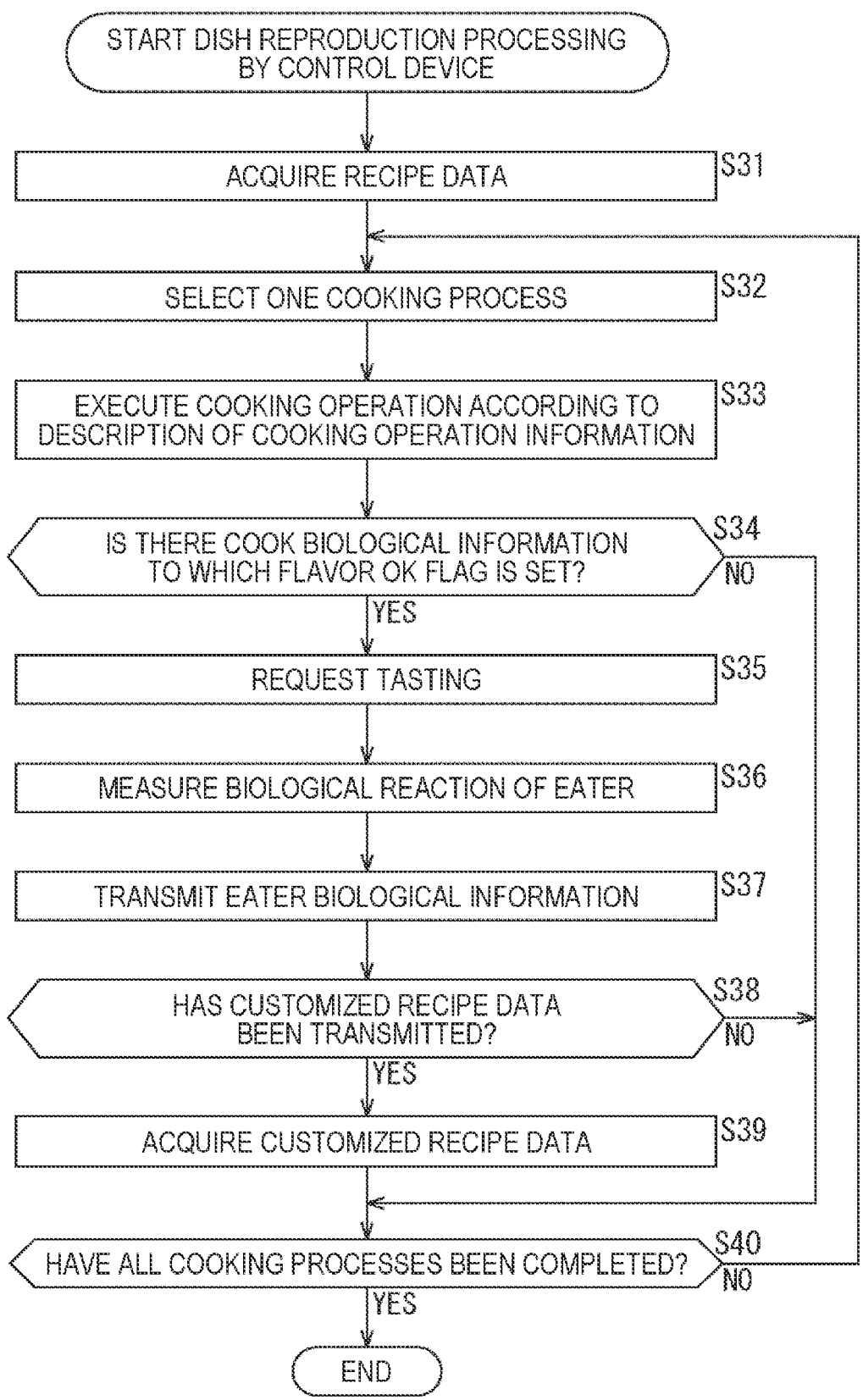
FIG. 39 is a flowchart for describing dish reproduction processing of the control device.

Dish reproduction processing of the control device 12 will be described with reference to the flowchart of FIG. 39.

In step S31, the recipe data acquisition unit 511 of FIG. 36 acquires the recipe data transmitted from the data processing device 11. The recipe data acquired by the recipe data acquisition unit 511 is analyzed by the recipe data analysis unit 512, and the cooking operation information and the cook biological information are extracted. The cooking operation information is supplied to the control unit 515, and the cook biological information is supplied to the biological information processing unit 514.

In step S32, the control unit 515 selects one cooking process as a cooking process to be executed. The cooking processes are selected in order from the cooking process data set related to the first cooking process.

In step S33, the control unit 515 generates the instruction command on the basis of the description of the cooking operation information and transmits the instruction command to the cooking robot 1 to cause the cooking arms 321 to execute the cooking operation.

In step S34, the biological information processing unit 514 determines whether or not there is cook biological information to which the flavor OK flag is set.

In a case where it is determined in step S34 that there is the cook biological information to which the flavor OK flag is set, the biological information processing unit 514 requests the eater to have a taste in step S35.

In step S36, the control unit 515 transmits the instruction command to cause the cooking robot 1 to measure the biological reaction of when the eater is having a taste.

In step S37, the biological information processing unit 514 generates the eater biological information on the basis of the sensor data transmitted from the cooking robot 1 and transmits the eater biological information to the data processing device 11.

In the data processing device 11, the processing described with reference to FIG. 38 is performed, and the recipe data is customized as necessary. When the recipe data is customized, the customized recipe data is transmitted from the data processing device 11.

In step S38, the recipe data acquisition unit 511 determines whether or not the customized recipe data has been transmitted from the data processing device 11.

In a case where it is determined in step S38 that the customized recipe data has been transmitted, in step S39, the recipe data acquisition unit 511 acquires the customized recipe data transmitted from the data processing device 11. In a case where the recipe data is customized, the subsequent processing is performed on the basis of the customized recipe data.

Meanwhile, in step S34, in a case where it is determined that there is no cook biological information to which the flavor OK flag is set, the processing of steps S35 to S39 is skipped. Furthermore, in step S38, in a case where it is determined that the customized recipe data has not been transmitted, processing of step S39 is skipped.

In step S40, the control unit 515 determines whether or not all the cooking processes have been completed, and in a case where it is determined that all the cooking processes have not been completed yet, the processing returns to step S32 and the above-described processing is repeated. Similar processing is repeated for the next cooking process.

On the other hand, when it is determined in step S40 that all the cooking steps have been completed, the dish is completed and the dish reproduction processing is terminated.

Through the above series of processing, a dish that is the same as the dish made by the chef with flavor customized according to the taste of the eater is reproduced.

The eater can customize the dish that is the same as the dish made by the chef according to its preference.

Furthermore, the chef can customize the dish made by the chef according to the preference of each person and provides the customized dish to various people.

<Recipe Data Including Flavor Information>

Figure 40:
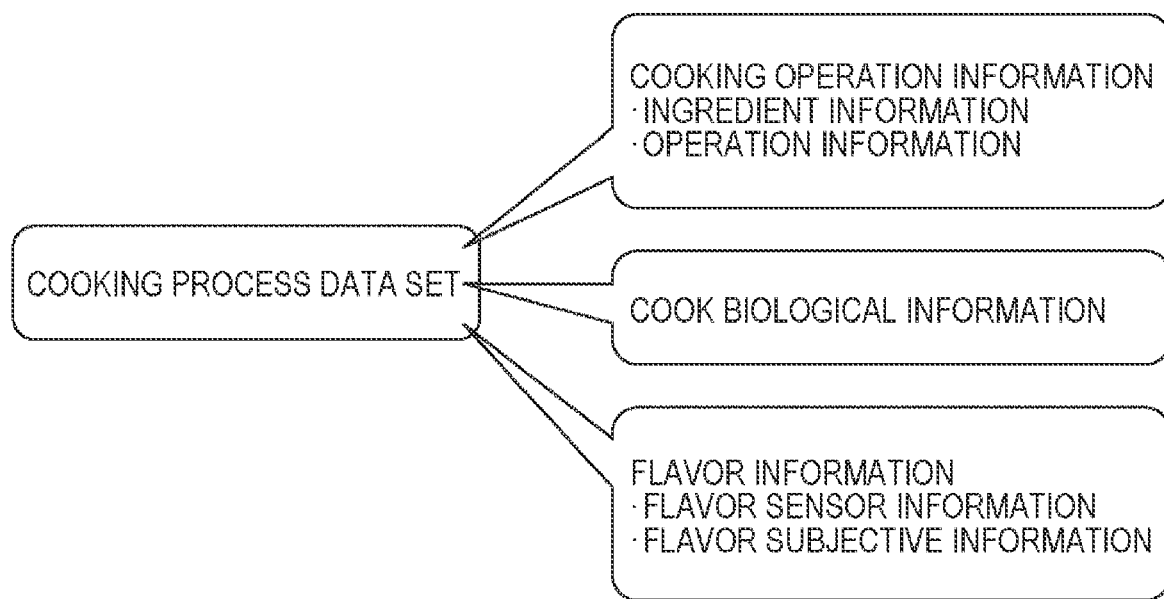
FIG. 40 is a diagram illustrating an example of information contained in a cooking process data set.

FIG. 40 is a diagram illustrating an example of information contained in a cooking process data set.

As illustrated in the balloons of FIG. 40, the flavor information that is information regarding the flavor of the ingredient may be included in the cooking process data set, in addition to the above-described cooking operation information and the cook biological information. Overlapping description will be omitted as appropriate.

The flavor information is sensation data obtained by digitizing the flavor obtained by the chef as a sensation when cooking. Hereinafter, the flavor information will be described below.

As illustrated in FIG. 40, the flavor information includes flavor sensor information and flavor subjective information.

(1) Flavor Sensor Information

The flavor sensor information configuring the flavor information is sensor data obtained by measuring the flavor of an ingredient with a sensor. The sensor data obtained by measuring the flavor of the ingredient that has not been cooked by the sensor may be included in the flavor information as the flavor sensor information.

Since the flavor is configured by the taste, aroma, texture, apparent temperature, and color, the flavor sensor information includes sensor data related to the taste, sensor data related to the aroma, sensor data related to the texture, sensor data related to the apparent temperature, and sensor data related to the color. All the sensor data may be included in the flavor sensor information or any sensor data may not be included in the flavor sensor information.

Respective sensor data configuring the flavor sensor information are referred to as gustatory sensor data, olfaction sensor data, texture sensor data, apparent temperature sensor data, and color sensor data.

The gustatory sensor data is sensor data measured by the gustatory sensor. The gustatory sensor data is configured by at least one parameter of a saltiness sensor value, a sourness sensor value, a bitterness sensor value, a sweetness sensor value, an umami sensor value, a pungent sensor value, and an astringency sensor value.

The gustatory sensor includes, for example, an artificial lipid membrane-type gustatory sensor using an artificial lipid membrane in a sensor unit. The artificial lipid membrane-type gustatory sensor is a sensor that detects a change in a membrane potential caused by electrostatic and hydrophobic interactions of the lipid membrane with respect to a gustatory substance that is a substance causing the taste to be felt, and outputs the change as a sensor value.

A device capable of converting the respective elements of the saltiness, sourness, bitterness, sweetness, umami, pungency, and astringency configuring the taste of a food into data and outputting the data can use various devices such as a gustatory sensor using a polymer film as the gustatory sensor, instead of the artificial lipid membrane-type gustatory sensor.

The olfaction sensor data is sensor data measured by an olfactory sensor. The olfaction sensor data is configured by a value for each element expressing the aroma, such as spicy aroma, fruity aroma, grassy smell, musty smell (cheesy), citrus aroma, and rose aroma.

The olfactory sensor includes, for example, a sensor provided with innumerable sensors such as a crystal oscillator. A crystal oscillator is used instead of human nasal receptors. The olfactory sensor using the crystal oscillator detects a change in an oscillation frequency of the crystal oscillator of when an aroma component hits the crystal oscillator, and outputs a value expressing the above-described aroma on the basis of a pattern of the change in the oscillation frequency.

A device capable of outputting a value expressing the aroma can use various devices using a sensor formed using various materials such as carbon instead of the human nasal receptors as the olfactory sensor, instead of the sensor using the crystal oscillator.

The texture sensor data is sensor data specified by analyzing an image taken by a camera and sensor data measured by various sensors. The texture sensor data is configured by at least one parameter of information representing hardness, stickiness, viscosity (stress), cohesiveness, polymer content, water content, oil content, and the like.

The hardness, stickiness, viscosity, and cohesiveness are recognized by, for example, analyzing an image of the ingredient cooked by the chef captured by the camera. For example, by analyzing an image of a soup stirred by the chef, values of the hardness, stickiness, viscosity, and cohesiveness can be recognized. These values may be recognized by measuring the stress of when the chef cuts the ingredient with a kitchen knife.

The polymer content, water content, and oil content are measured by, for example, a sensor that irradiates the ingredient with light having a predetermined wavelength and analyzes reflected light to measure the values.

A database in which each ingredient and each parameter of the texture are associated with each other is prepared, and the texture sensor data of each ingredient may be recognized by referring to the database.

The apparent temperature sensor data is sensor data obtained by measuring the temperature of the ingredient with a temperature sensor.

The color sensor data is data specified by analyzing the color of the ingredient from an image captured by a camera.

(2) Flavor Subjective Information

The flavor subjective information is information representing how a person such as the chef who is cooking feels a subjective flavor. The flavor subjective information is calculated on the basis of the flavor sensor information.

Since the flavor is configured by the taste, aroma, texture, apparent temperature, and color, the flavor subjective information includes subjective information related to the taste, subjective information related to the aroma, subjective information related to the texture, subjective information related to the apparent temperature, and subjective information related to the color. All the subjective information related to the taste, subjective information related to the aroma, subjective information related to the texture, subjective information related to the apparent temperature, and subjective information related to the color may be included in the flavor subjective information or some subjective information may not be included in the flavor subjective information.

Respective pieces of subjective information configuring the flavor subjective information are referred to as gustatory subjective information, olfactory subjective information, texture subjective information, apparent temperature subjective information, and color subjective information.

Figure 41:
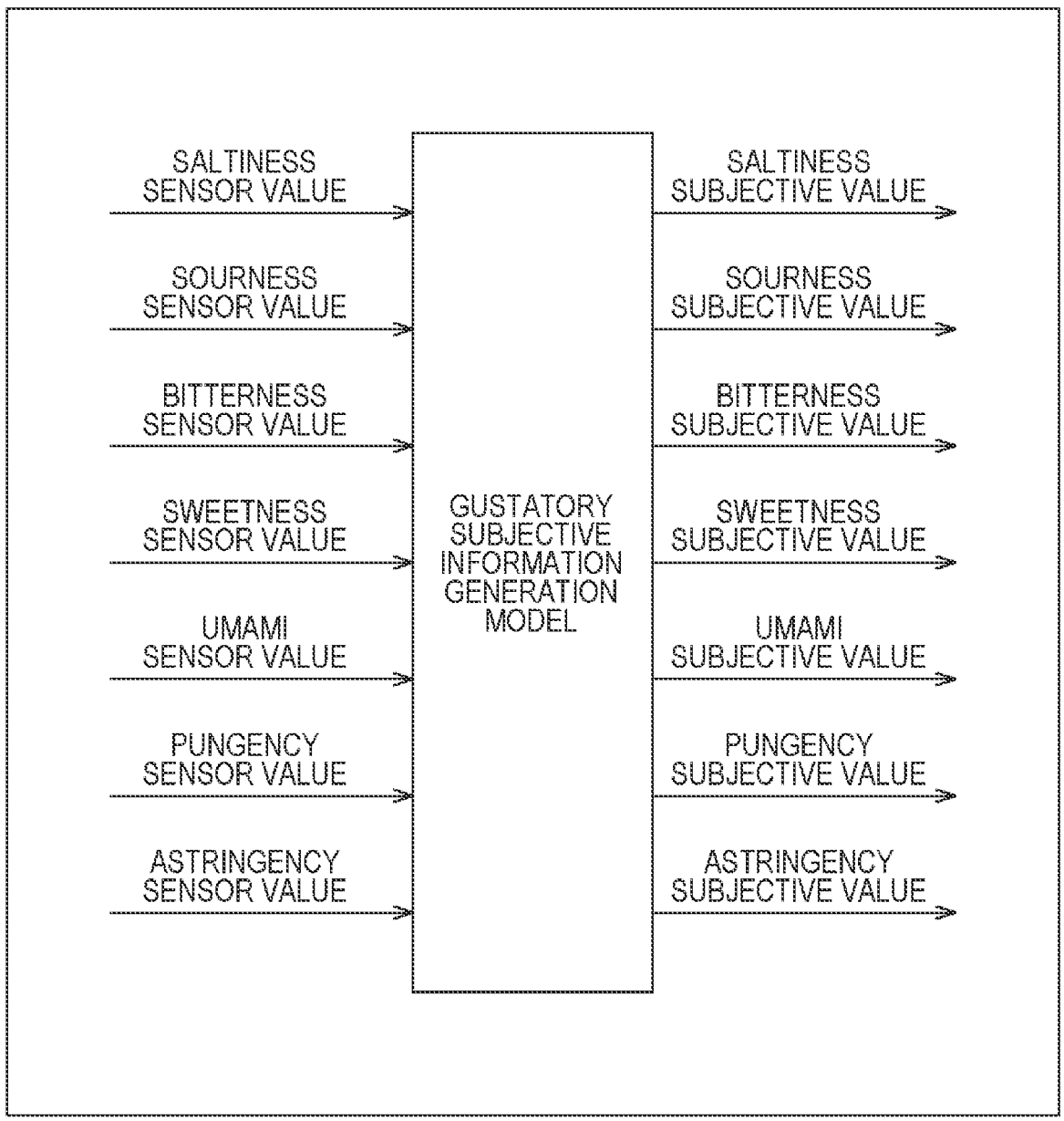
FIG. 41 is a diagram illustrating a calculation example of gustatory subjective information.

FIG. 41 is a diagram illustrating a calculation example of gustatory subjective information.

As illustrated in FIG. 41, the gustatory subjective information is calculated using the gustatory subjective information generation model that is a model of a neural network generated by deep learning or the like. The gustatory subjective information generation model is generated in advance by performing learning using the gustatory sensor data of a certain ingredient and information (numerical values) representing how the chef who has eaten the ingredient feels the taste, for example.

For example, as illustrated in FIG. 41, in a case of inputting the saltiness sensor value, the sourness sensor value, the bitterness sensor value, the sweetness sensor value, the umami sensor value, the pungent sensor value, and the astringency sensor value that are the gustatory sensor data of a certain ingredient, a saltiness subjective value, a sourness subjective value, a bitterness subjective value, a sweetness subjective value, an umami subjective value, a pungency subjective value, and an astringency subjective value are output from the gustatory subjective information generation model.

The saltiness subjective value is a value representing how the chef feels the saltiness. The sourness subjective value is a value representing how the chef feels the sourness. Similarly, the bitterness subjective value, the sweetness subjective value, the umami subjective value, the pungency subjective value, and the astringency subjective value are values respectively representing how the chef feels the bitterness, sweetness, umami, pungency, and astringency.

Similarly, the other pieces of subjective information configuring the flavor subjective information are calculated using respective models for generating subjective information.

That is, the olfactory subjective information is calculated by inputting the olfaction sensor data into the olfactory subjective information generation model, and the texture subjective information is calculated by inputting the texture sensor data into the texture subjective information generation model. The apparent temperature subjective information is calculated by inputting the apparent temperature subjective sensor data into the apparent temperature subjective information model, and the color subjective information is calculated by inputting the color sensor data into the color subjective information generation model.

The gustatory subjective information may be calculated on the basis of table information in which the gustatory sensor data of a certain ingredient is associated with the information representing how the chef who has eaten the ingredient feels the taste, instead of using the neural network model. Various methods can be adopted for calculating the flavor subjective information using the flavor sensor information.

As described above, the recipe data is configured by linking (associating) the cooking operation information that is the information regarding the cooking operation for realizing the cooking process, the cook biological information representing the biological reaction of the cook, and the flavor information that is the information regarding the flavor of the ingredient or the dish measured in conjunction with the progress of the cooking process.

Example of Flow of Generation of Recipe Data and Reproduction of Dish

Figure 42:
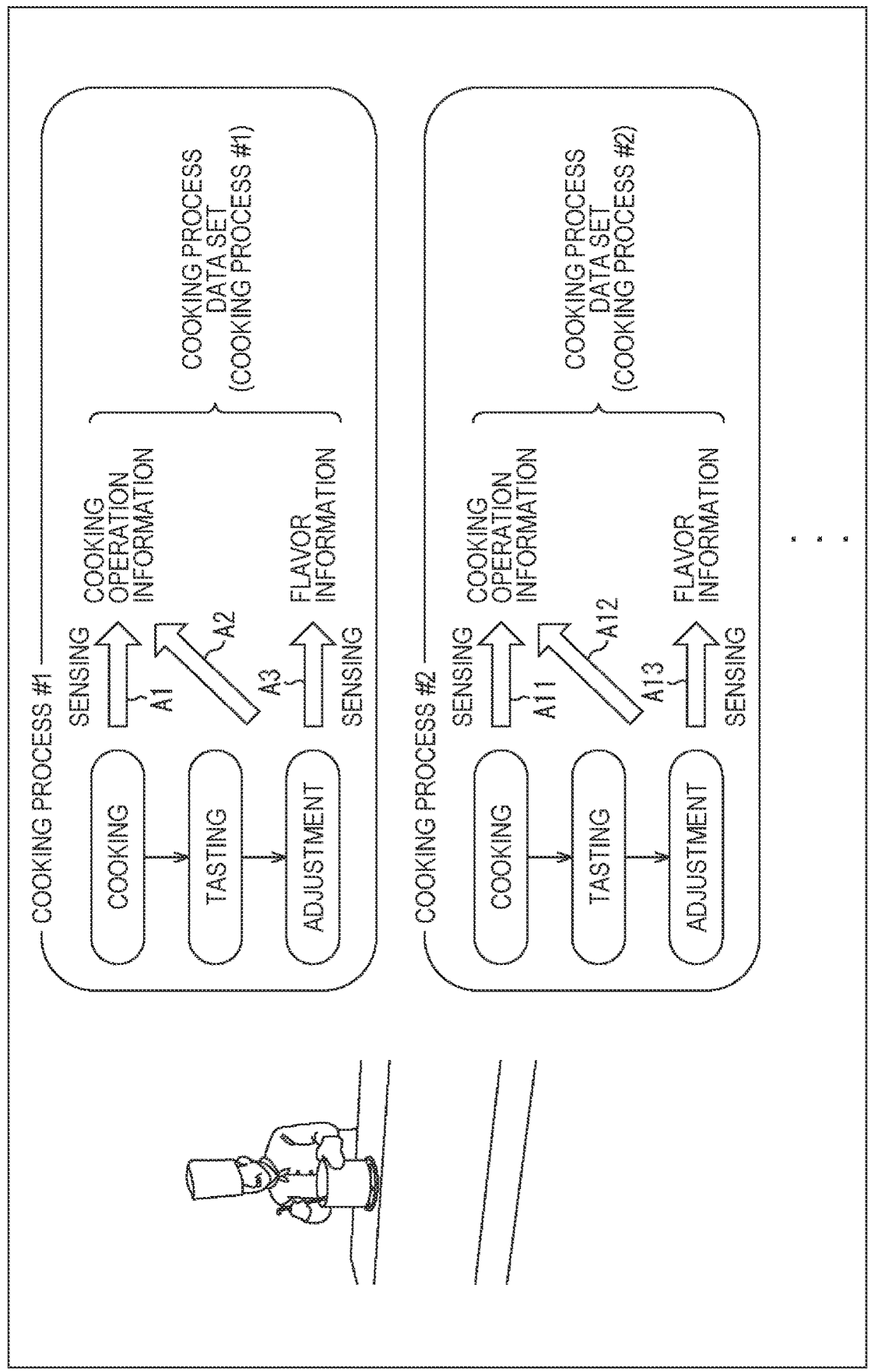
FIG. 42 is a diagram illustrating an example of a flow of generating the recipe data.

FIG. 42 is a diagram illustrating an example of a flow of generating the recipe data.

Note that FIG. 42 omits illustration of processing regarding the biological information. The same similarly applies to FIG. 43.

As illustrated in FIG. 42, the cooking operation information configuring the cooking process data set is generated on the basis of sensing results by sensing the operation of the chef who cooks using ingredients and the operation of the chef who adjusts the flavor.

Furthermore, the flavor information is generated on the basis of a sensing result by sensing the flavor of the cooked ingredients. The above-described various sensors for measuring the flavor of the ingredient are prepared on the chef side.

In the example of FIG. 42, as illustrated by the arrows A1 and A2, the cooking operation information configuring the cooking process data set of the cooking process #1 is generated on the basis of the sensing results of the cooking operation performed by the chef as the cooking process #1 and the operation of the chef for adjusting the flavor.

Furthermore, as illustrated by the arrow A3, the flavor information configuring the cooking process data set of the cooking process #1 is generated on the basis of the sensing result of the flavor of the cooked ingredients by the cooking process #1.

After the cooking process #1 is completed, the cooking process #2, which is the next cooking process" is performed.

Similarly, as illustrated by the arrows A11 and A12, the cooking operation information configuring the cooking process data set of the cooking process #2 is generated on the basis of the sensing results of the cooking operation performed by the chef as the cooking process #2 and the operation of the chef for adjusting the flavor.

Furthermore, as illustrated by the arrow A13, the flavor information configuring the cooking process data set of the cooking process #2 is generated on the basis of the sensing result of the flavor of the cooked ingredients by the cooking process #2.

One dish is completed through such a plurality of cooking processes. Furthermore, as the dish is completed, the recipe data describing the cooking process data set of each cooking process is generated.

The unit of the cooking operation included in one cooking process can be arbitrarily set. One cooking process may be configured by cooking operations not involving tasting or post-tasting flavor adjustment or may be configured by the flavor adjustment. In this case as well, the flavor information obtained on the basis of the sensing result by sensing the flavor for each cooking process is included in the cooking process data set.

Timing for sensing the flavor can also be arbitrarily set rather than sensing the flavor each time one cooking process is completed. For example, flavor sensing may be repeated during one cooking process. In this case, the cooking process data set includes time series data of the flavor information.

The flavor information may be included in the cooking process data set together with the information of the cooking operation performed at the timing each time the flavor is measured at arbitrary timing, rather than the flavor information being included in all the cooking process data sets.

Figure 43:
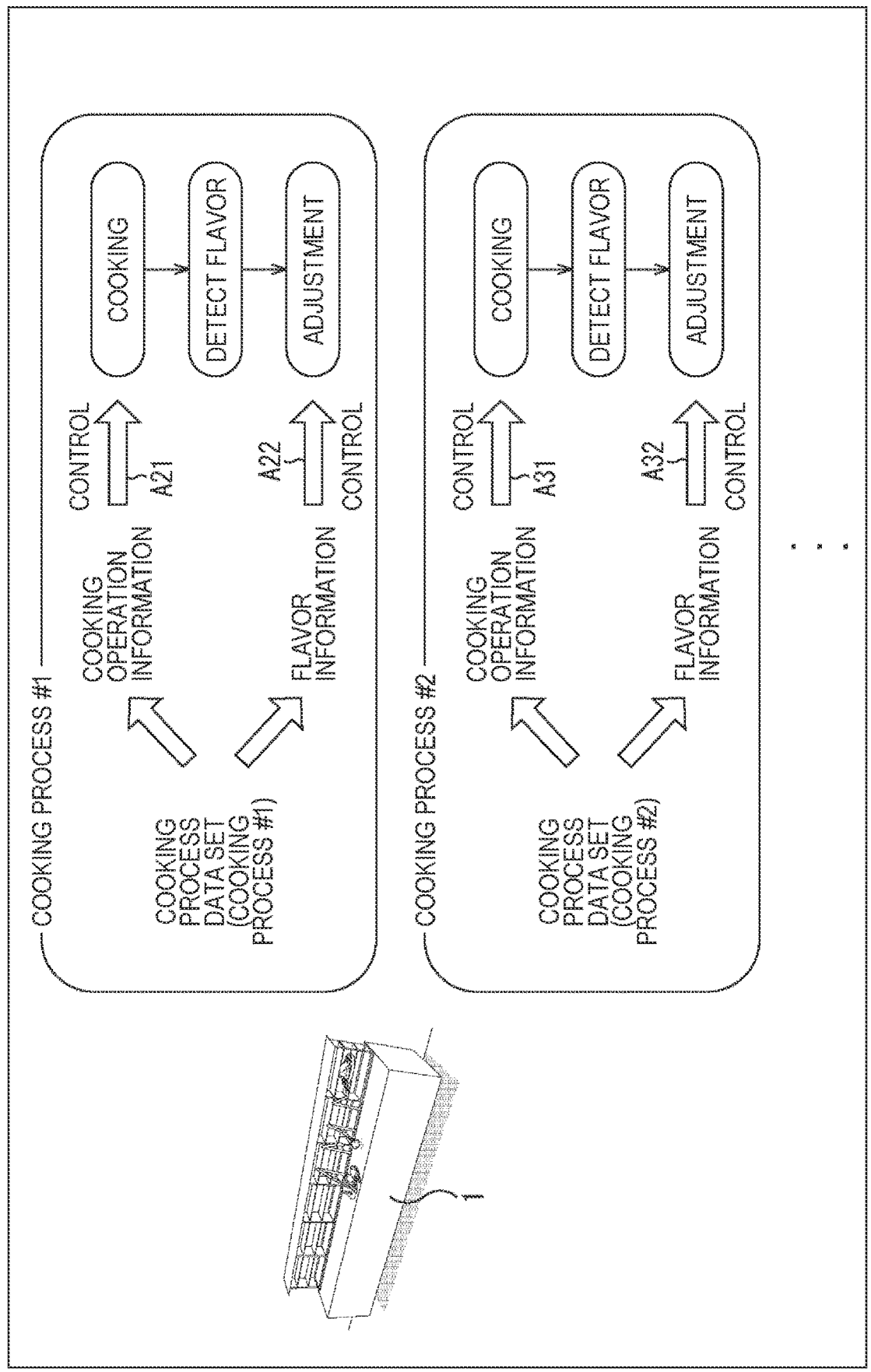
FIG. 43 is a diagram illustrating an example of a flow of reproducing a dish based on the recipe data.

FIG. 43 is a diagram illustrating an example of a flow of reproducing a dish based on the recipe data.

As illustrated in FIG. 43, the reproduction of a dish by the cooking robot 1 is performed by repeating, for each cooking process, cooking on the basis of the cooking operation information included in the cooking process data set described in the recipe data, measuring the flavor of the cooked ingredients, and adjusting the flavor. Various sensors for measuring the flavor of the ingredient are also prepared on the cooking robot 1 side.

The flavor is adjusted by adding work so that the flavor measured by the sensor prepared on the cooking robot 1 side approaches the flavor represented by the flavor information, for example.

The flavor measurement and adjustment may be repeated, for example, a plurality of times in a cooking process. That is, each time the adjustment is performed, the flavor is measured for the adjusted ingredients, and the flavor is adjusted on the basis of the measurement result.

In the example of FIG. 43, as illustrated by the arrow A21, the cooking operation of the cooking robot 1 is controlled on the basis of the cooking operation information configuring the cooking process data set of the cooking process #1, and an operation same as the operation of the cooking process #1 of the chef is performed by the cooking robot 1.

After the operation same as the operation of the cooking process #1 of the chef is performed by the cooking robot 1, the flavor of the cooked ingredients is measured, and as illustrated by the arrow A22, adjustment of the flavor of the cooking robot 1 is controlled on the basis of the flavor information configuring the cooking process data set of the cooking process #1.

In a case where the flavor measured by the sensor prepared on the cooking robot 1 side matches the flavor represented by the flavor information, the flavor adjustment is completed and the cooking process #1 is also completed. For example, the flavor measured by the sensor prepared on the cooking robot 1 side and the flavor represented by the flavor information are determined to match when not only the flavors are exactly the same but also when the flavors are similar by a threshold value or more.

After the cooking process #1 is completed, the cooking process #2, which is the next cooking process" is performed.

Similarly, as illustrated by the arrow A31, the cooking operation of the cooking robot 1 is controlled on the basis of the cooking operation information configuring the cooking process data set of the cooking process #2, and an operation same as the operation of the cooking process #2 of the chef is performed by the cooking robot 1.

After the operation same as the operation of the cooking process #2 of the chef is performed by the cooking robot 1, the flavor of the cooked ingredients is measured, and as illustrated by the arrow A32, adjustment of the flavor of the cooking robot 1 is controlled on the basis of the flavor information configuring the cooking process data set of the cooking process #2.

In a case where the flavor measured by the sensor prepared on the cooking robot 1 side matches the flavor represented by the flavor information, the flavor adjustment is completed and the cooking process #2 is also completed.

Through such a plurality of cooking processes, the dish made by the chef is reproduced by the cooking robot 1.

Since the cooking by the cooking robot 1 is performed by adjusting the flavor for each cooking process, the final dish will be a dish with the same or similar flavor to the dish made by the chef. In this way, the dish with the same flavor as the dish made by the chef is reproduced on the basis of the recipe data.

The chef can serve the dish with the same flavor as the dish made by the chef to a person who cannot visit the chef's own restaurant, for example. In addition, the chef can leave the dishes made by the chef in a reproducible form as the recipe data.

Meanwhile, a person who eats the dish reproduced by the cooking robot 1 can eat the dish with the same flavor as the dish prepared by the chef.

Figure 44:
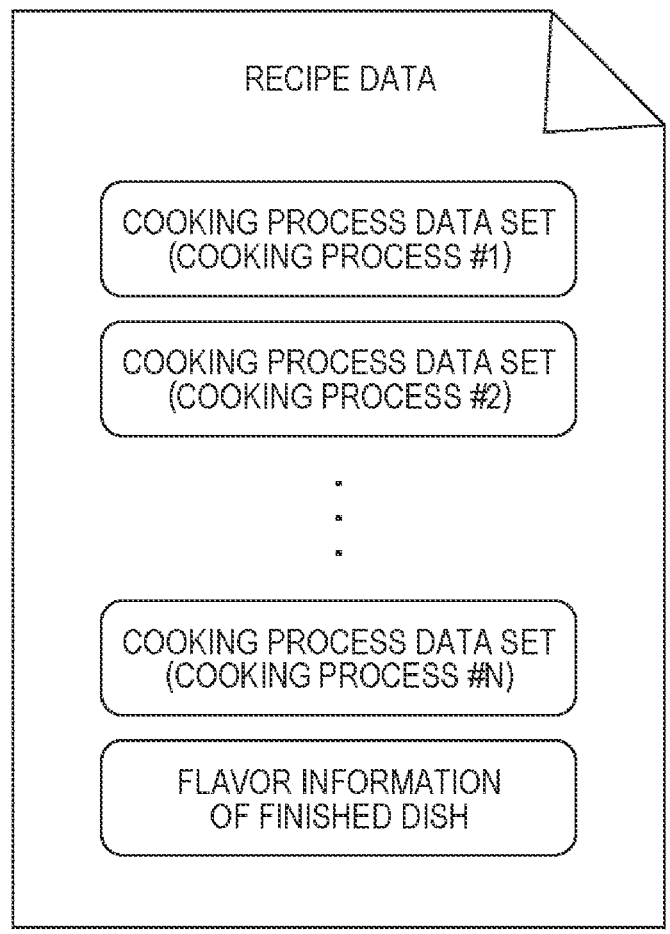
FIG. 44 is a diagram illustrating an example of description content of recipe data.

FIG. 44 is a diagram illustrating an example of another description content of the recipe data.

As illustrated in FIG. 44, the recipe data may include flavor information regarding the flavor of the finished dish. In this case, the flavor information regarding the flavor of the finished dish is linked to the overall cooking operation information.

In this way, the associated relationship between the cooking operation information and the flavor information does not have to be one-to-one.

<Modifications>

Although the recipe data is customized on the basis of the biological reaction of the eater, the customization may be performed on the basis of other information related to the eater.

For example, the recipe data can be customized on the basis of attributes of the eater, such as age, gender, nationality, and living area. In a case where the recipe data is customized on the basis of nationality, recipe data for each nationality is generated, such as recipe data for Japanese nationals, recipe data for American nationals, and recipe data for French nationals.

Sound information related to cooking on the chef's side may be included in the recipe data as environment information. Sound related to cooking includes sound of cutting ingredients with a knife and sound of boiling ingredients in a pot.

Modification of Configuration

The cooking robot that reproduces a dish on the basis of the recipe data has been assumed to be the cooking robot 1 installed in a home, but cooking may be reproduced by cooking robots installed in various places. For example, the above-described technique can be applied even in a case where cooking is reproduced by a cooking robot installed in a factory or a cooking robot installed in a restaurant.

Furthermore, the cooking robot that reproduces a dish on the basis of the recipe data has been the cooking robot 1 that operates the cooking arms to cook, but the dishes may be reproduced by various cooking robots capable of cooking ingredients by a configuration other than the cooking arms.

In the above description, the cooking robot 1 has been controlled by the control device 12, but the cooking robot 1 may be directly controlled by the data processing device 11 that generates the recipe data. In this case, the data processing device 11 is provided with each configuration of the command generation unit 501 described with reference to FIG. 36.

Furthermore, each configuration of the command generation unit 501 may be provided in the recipe data management server 21.

The server function of the recipe data management server 21 that manages the recipe data and provides the recipe data to other devices may be provided in the data processing device 11 that generates the recipe data.

Figure 45:
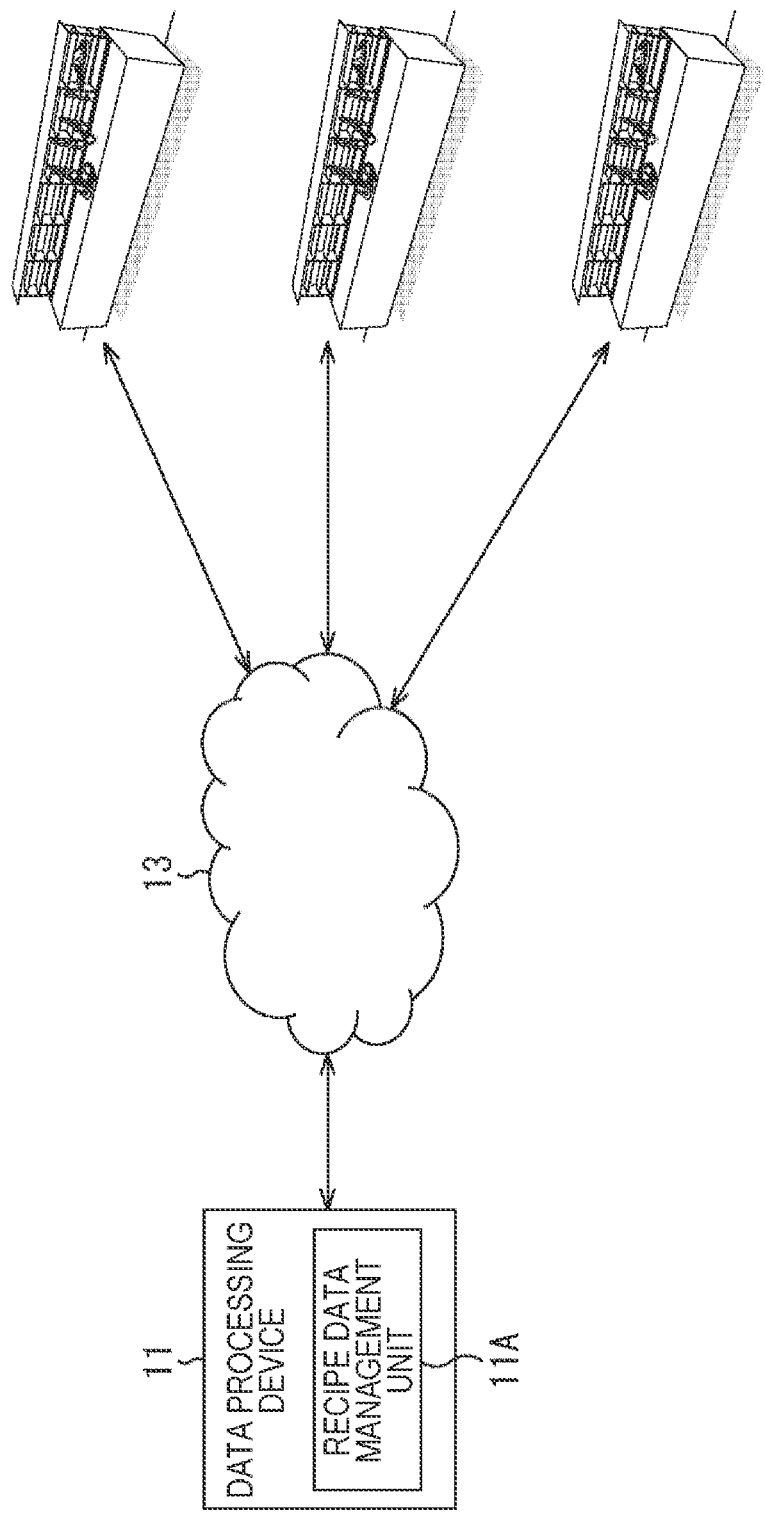
FIG. 45 is a diagram illustrating another configuration example of the cooking system.

FIG. 45 is a diagram illustrating another configuration example of the cooking system.

A recipe data management unit 11A included in the data processing device 11 has a server function to manage the recipe data and provide the recipe data to other devices. The recipe data managed by the recipe data management unit 11A is provided to a plurality of cooking robots and a control device for controlling the cooking robots.

Data Management

Since the above-described recipe data, cooking process data sets (cooking operation information and flavor information), and the like can be said to be products that creatively express thoughts and feelings about the cooking processes, they can be considered as literary works.

For example, the chef who cooks (for example, the chef who runs a famous restaurant) completes a delicious dish with creativity by repeating trials of selection of ingredients and tasting in the cooking processes. In this case, the recipe data and the cooking process data set (cooking operation information and flavor information) have value as data, and a situation where compensation is required when used by others can be assumed.

Therefore, an application of managing copyright of the recipe data, cooking process data sets (cooking operation information and flavor information), and the like in a similar manner to music or the like can be considered.

That is, in the present disclosure, it is also possible to protect individual recipe data and cooking process data sets by using copyright protection techniques such as copy protection and encryption, which provide protection functions for individual data.

In this case, for example, the recipe data management server 21 of FIG. 25 (the data processing device 11 of FIG. 45) manages the copyright in a state where the chef and the recipe data (or cooking process data sets) are associated with each other.

Next, in a case where the user wants the cooking robot 1 to cook using the recipe data, the user pays a use fee for the recipe data, thereby using the recipe data downloaded to the control device 12 for the cooking by the cooking robot 1, for example. Note that the use fee is gone back to the chef who is the creator of the recipe data, a data manager who manages the recipe data, and the like.

Furthermore, in the present disclosure, it is also possible to protect individual recipe data and cooking process data sets by using blockchain technology for managing a transaction history of data as a ledger on a server in a distributed manner.

In this case, for example, the recipe data management server 21 of FIG. 25 (the data processing device 11 of FIG. 45) manages the chef and the recipe data (or cooking process data sets) in association with each other, using the blockchain technology for managing a transaction history of data as a ledger on a server (cloud server or edge server) in a distributed manner.

Next, in a case where the user wants the cooking robot 1 to cook using the recipe data, the user pays a use fee for the recipe data, thereby using the recipe data downloaded to the control device 12 for the cooking by the cooking robot 1, for example. Note that the use fee is gone back to the chef who is the creator of the recipe data, a data manager who manages the recipe data, and the like.

In this way, the recipe data (or cooking process data sets) can be efficiently managed as a creatively expressed work in consideration of the relationship among the chef, the user, and the use fee.

Program

The series of processing described above can be executed by hardware or software. In a case where the series of processing is executed by software, a program constituting the software is installed in a computer incorporated in dedicated hardware, a general-purpose personal computer, or the like.

The program to be installed is recorded on and provided with the removable medium 211 illustrated in FIG. 28, which includes an optical disk (a compact disc-read only memory (CD-ROM), a digital versatile disc (DVD), or the like), a semiconductor memory, or the like. Further, the program may be provided via a wired or wireless transmission medium such as a local area network, the Internet, or digital broadcast. The program can be installed in the ROM 202 or the storage unit 208 in advance.

The program executed by the computer may be a program processed in chronological order according to the order described in the present specification or may be a program executed in parallel or at necessary timing such as when a call is made.

Note that, in this specification, the term "system" means a group of a plurality of configuration elements (devices, modules (parts), and the like), and whether or not all the configuration elements are in the same housing is irrelevant. Therefore, a plurality of devices housed in separate housings and connected via a network, and one device that houses a plurality of modules in one housing are both systems.

The effects described in this specification are merely examples and are not limited, and other effects may be exhibited.

Embodiments of the present technology are not limited to the above-described embodiments, and various modifications can be made without departing from the gist of the present technology.

For example, in the present technology, a configuration of cloud computing in which one function is shared and processed in cooperation by a plurality of devices via a network can be adopted.

Furthermore, the steps described in the above-described flowcharts can be executed by one device or can be shared and executed by a plurality of devices.

Moreover, in a case where a plurality of processes is included in one step, the plurality of processes included in the one step can be executed by one device or can be shared and executed by a plurality of devices.

REFERENCE SIGNS LIST

1 Cooking robot
11 Data processing device
12 Control device
21 Recipe data management server
41 Camera
42 Biosensor
221 Data processing unit
231 Cooking operation information generation unit
232 Cook biological information generation unit
233 Recipe data generation unit
234 Recipe data output unit
235 Eater biological information acquisition unit
321 Cooking arm
361 Controller
401 Camera
402 Biosensor
403 Communication unit
501 Command generation unit
511 Recipe data acquisition unit
512 Recipe data analysis unit
513 Robot state estimation unit
514 Biological information processing unit
515 Control unit
516 Command output unit

The invention claimed is:

1. A cooking robot comprising:
a cooking arm configured to perform a cooking operation for making a dish; and
a control unit configured to control the cooking operation performed by the cooking arm using recipe data including a data set in which cooking operation data and cook biological data are linked,
wherein the cooking operation data describes information regarding an ingredient of the dish and information regarding each operation of a cook in a cooking process using the ingredient,
wherein the cook biological data indicates a biological reaction of the cook measured in conjunction with a progress of the cooking process,
wherein the cooking operation data and the cook biological data are linked for each respective tasting process in which the cook tries a taste of the ingredient and measured content of the cook biological data during the respective tasting process satisfies a predetermined condition, and
wherein the control unit is implemented via at least one processor.

2. The cooking robot according to claim 1, wherein
the cook biological data is linked to sensation data indicating a sensation of the cook measured in conjunction with the progress of the cooking process.

3. The cooking robot according to claim 1, wherein
the cook biological data includes brain wave data indicating a state of a brain wave of the cook.

4. The cooking robot according to claim 1, wherein
the cook biological data includes face state data indicating a state of a face of the cook.

5. The cooking robot according to claim 1, wherein
the cook biological data includes heartbeat data indicating a state of heartbeat of the cook.

6. The cooking robot according to claim 1, wherein
the cook biological data includes pupil data indicating a state of a pupil of the cook.

7. The cooking robot according to claim 1, wherein
the cook biological data is data indicating a reaction of when the cook has a taste.

8. The cooking robot according to claim 1, wherein
the recipe data is updated according to eater biological data indicating a biological reaction of the eater who eats the cooked ingredient obtained by cooking by the cooking robot or the dish cooked by the cooking robot, and
the control unit controls the cooking operation performed by the cooking arm, using the updated recipe data.

9. The cooking robot according to claim 8, wherein
the recipe data is updated for the each eater by updating the cooking process, and
the control unit controls the cooking operation performed by the cooking arm, using the recipe data updated for the each eater.

10. The cooking robot according to claim 8, wherein
the recipe data is updated for each attribute of the eater by updating the cooking process, and
the control unit controls the cooking operation performed by the cooking arm, using the recipe data updated for the each attribute of the eater.

11. The cooking robot according to claim 8, wherein
the eater biological data is data indicating a reaction of when the eater eats.

12. The cooking robot according to claim 8, wherein
the eater biological data is data indicating a state of a voice of when the eater eats.

13. The cooking robot according to claim 8, wherein
the eater biological data is data indicating a state of electromyogram of a body of when the eater eats.

14. The cooking robot according to claim 1, wherein
the control unit controls the cooking arm according to an instruction command generated on a basis of the recipe data and which gives an instruction on the cooking operation.

15. The cooking robot according to claim 14, wherein
a plurality of the cooking arms is provided.

16. The cooking robot according to claim 15, wherein
the control unit causes a plurality of the cooking arms to perform the cooking operation in cooperation according to the instruction command.

17. A cooking robot control device comprising:
a control unit configured to control a cooking operation performed by a cooking arm included in a cooking robot, using recipe data including a data set in which cooking operation data and cook biological data are linked,
wherein the cooking operation data describes information regarding an ingredient of a dish and information regarding each operation of a cook in a cooking process using the ingredient,
wherein the cook biological data indicates a biological reaction of the cook measured in conjunction with a progress of the cooking process,
wherein the cooking operation data and the cook biological data are linked for each respective tasting process in which the cook tries a taste of the ingredient and measured content of the cook biological data during the respective tasting process satisfies a predetermined condition, and
wherein the control unit is implemented via at least one processor.

18. A cooking robot comprising:
a cooking arm configured to perform a cooking operation for making a dish; and
a control unit configured to control the cooking operation performed by the cooking arm using recipe data including a data set in which cooking operation data and eater biological data are linked,
wherein the cooking operation data describes information regarding an ingredient of the dish and information regarding each operation of a cook in a cooking process using the ingredient,
wherein the eater biological data indicates a biological reaction of an eater who eats the dish cooked by the cooking robot,
wherein the cooking operation data and the eater biological data are linked for each respective tasting process in which the eater tries a taste of the ingredient and measured content of the cook biological data during the respective tasting process satisfies a predetermined condition
wherein the control unit is implemented via at least one processor.

* * * * *